(12) United States Patent
Fossati

(10) Patent No.: US 10,780,094 B2
(45) Date of Patent: Sep. 22, 2020

(54) USE OF CARBONIC ANHYDRASE INHIBITORS FOR TREATMENT OF NEUROLOGICAL AND PSYCHIATRIC DISORDERS

(71) Applicant: New York University, New York, NY (US)

(72) Inventor: Silvia Fossati, Long Island City, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 15/657,022

(22) Filed: Jul. 21, 2017

(65) Prior Publication Data

US 2018/0161339 A1    Jun. 14, 2018

Related U.S. Application Data

(60) Provisional application No. 62/365,823, filed on Jul. 22, 2016.

(51) Int. Cl.
| | | |
|---|---|---|
| A61K 31/549 | (2006.01) | |
| A61K 31/542 | (2006.01) | |
| A61K 31/433 | (2006.01) | |
| A61K 31/18 | (2006.01) | |
| A61K 31/382 | (2006.01) | |
| A61K 31/404 | (2006.01) | |
| A61P 25/16 | (2006.01) | |
| A61K 31/423 | (2006.01) | |
| A61K 31/415 | (2006.01) | |
| A61K 31/428 | (2006.01) | |
| A61K 45/06 | (2006.01) | |
| A61P 25/28 | (2006.01) | |
| A61K 31/357 | (2006.01) | |

(52) U.S. Cl.
CPC ............ *A61K 31/549* (2013.01); *A61K 31/18* (2013.01); *A61K 31/357* (2013.01); *A61K 31/382* (2013.01); *A61K 31/404* (2013.01); *A61K 31/415* (2013.01); *A61K 31/423* (2013.01); *A61K 31/428* (2013.01); *A61K 31/433* (2013.01); *A61K 31/542* (2013.01); *A61K 45/06* (2013.01); *A61P 25/16* (2018.01); *A61P 25/28* (2018.01)

(58) Field of Classification Search
USPC ........................................................ 514/232
See application file for complete search history.

(56) References Cited

U.S. PATENT DOCUMENTS 5,755,237 A    5/1998   Rodriguez

FOREIGN PATENT DOCUMENTS

| WO | 2007/112288 A2 | 10/2007 |
| WO | 2007/114948 A2 | 10/2007 |

OTHER PUBLICATIONS

Oishi (Regional differences in cerebrovascular reactivity to acetazolamide in Alzheimer's disease, Journal Clin Neuroscience, 1999, 6(5), pp. 380-381).*
Cunha (Acetazolamide, Common Side Effects of Acetazolamide Tablets, https://www.rxlist.com/acetazolamide-sied-effects-drug-center.htm, Feb. 15, 2018, pp. 1-4).*
Daughton (Lower-dose prescribing: Minimizing "side effects" of pharmaceuticals on society and the environment, Science of the Total Environment 443 (2013) 324-337).*
Gilmour, K.M., "Perspectives on carbonic anhydrase", Comparative Biochemistry and Physiology, Part A (2010), vol. 157, pp. 193-197.
Farid, K. et al., "Brain perfusion SPECT imaging and acetazolamide challenge in vascular cognitive impairment", Nuclear Medicine Communications, Review Article (2012), vol. 33, pp. 571-580.
Fossati, S. et al., "The carbonic anhydrase inhibitor methazolamide prevents amyloid beta-induced mitochondrial dysfunction and caspase activation protecting neuronal and glial cells in vitro and in the mouse brain", Neurobiology of Disease (2016), vol. 86, pp. 29-40.
Fossati, S. et al., "Differential contribution of isoaspartate post-translational modifications to the fibrillization and toxic properties of amyloid β and the Asn23 Iowa mutation", Biochem J. (2013), vol. 456(3), pp. 347-360.
Fossati, S., et al., "TRAIL death receptors DR4 and DR5 mediate cerebral microvascular endothelial cell apoptosis induced by oligomeric Alzheimer's A beta" Cell Death Dis. (2012), vol. 3, e321.
Fossati, S., et al., "Insights into Caspase-Mediated Apoptotic Pathways Induced by Amyloid-beta in Cerebral Microvascular Endothelial Cells", Neurodegenerative Diseases (2012), vol. 10, pp. 324-328.
Fossati, S., et al., "Differential activation of mitochondrial apoptotic pathways by vasculotropic amyloid-beta variants in cells composing the cerebral vessel walls", FASEB J. (2010), vol. 24, pp. 229-41.
Likitjaroen, Y. et al., "Vasoreactivity induced by acetazolamide in patients with vascular dementia versus Alzheimer's disease", Journal of the Neurological Sciences (2009), vol. 283, pp. 32-35.
Meyer, J. S. et al., "Vasodilator Responses to Acetazolamide Tested in Subtypes of Vascular Dementia", Featured Clinical Investigation, Journal of Stroke and Cerebrovascular Diseases (1998), vol. 7, No. 5, pp. 323-329.
Oishi, M. et al., "Regional differences in cerebrovascular reactivity to acetazolamide in Alzheimer's disease", Clinical Studies, Journal of Clinical Neuroscience (1999), vol. 6(5), pp. 380-381.
Silvia Fossati, Maria E. Solesio, Evgeny Pavlov, Thomas Wisniewski, "Carbonic Anhydrase is a Crucial Target for Prevention of Mitochondrial Pathology in Alzheimer's Models", Alzheimer's & Dementia: The Journal of the Alzheimer's Association, vol. 12, Issue 7, P650, Jul. 2016.
Solesio, M. et al., "Carbonic Anhydrase is a Crucial Target for Prevention of Mitochondrial Pathology in Alzheimer's Models", Poster, Alzheimer's Association International Conference (AAIC), Jul. 2016.

(Continued)

*Primary Examiner* — Kathrien A Cruz
(74) *Attorney, Agent, or Firm* — Troutman Pepper Hamilton Sanders LLP

(57) ABSTRACT

The invention is directed to the use of carbonic anhydrase inhibitors for treatment of neurological and psychiatric disorders.

6 Claims, 45 Drawing Sheets
(31 of 45 Drawing Sheet(s) Filed in Color)

(56) References Cited

OTHER PUBLICATIONS

Supuran, C. T., "Carbonic anhydrases: novel therapeutic applications for inhibitors and activators", Nature (2008), vol. 7, pp. 168-181.
Wang, X. et al., "Inhibitors of Cytochrome c Release with Therapeutic Potential for Huntington's Disease", The Journal of Neuroscience (2008), vol. 28(38), pp. 9473-9485.
Wang, X. et al., "Methazolamide and Melatonin Inhibit Mitochondrial Cytochrome C Release and are Neuroprotective in Experimental Models of Ischemic Injury", Stroke (2009), vol. 40, pp. 1877-1885.
Solesio, M. et al., "Carbonic Anhydrase Inhibition Selectively Prevents Amyloid β Neurovascular Mitochondrial Toxicity" Aging Cell (2018) e12787, 15 pages total.
Grinberg et al.; Vasculaar pathology in the aged human brain; Acta Neuropathol, (2010) 119:277-290.
Pantoni, Leonardo; Cerebral small vessel disease: from pathogenesis and clinical characteristics to therapeutic ahallenges; Lancet Neurol, (2010), 9, 689-701.
Tanskanen et al.; Prevalence and severity of cerebral amyloid angiopathy: a population-based study on very eldery finns (Vantaa 85+); Neuropathology and Applied Neurobiology; (2012), 38, 329-336.
Biffi et al.; Cerebral Amyloid Angiopathy: A Systematic Review; J Clin Neurol, (2011), 7, 1-9.
Iadecola, Costantino; The Pathobiology of Vascular Dementia, Neuron, (2013), 80, 844-66.
Kisler et al.; Cerebral blood flow regulation and neurovascular dysfunction in Alzheimer's disease, Nat Rev Neurosci, (2017), 18, 419-434.
Alzforum: Networking for a Cure, "Tg-SwDI(APP—Swedish, Dutch, Iowa)" (2019) 5 pages total.
Ehrenreich, D.L. et al., "Influence of Acetazolamide on Cerebral Blood Flood" Archives of Neurology (1961) vol. 5, pp. 227-232.
Glodzik, L. et al., "Cerebrovascular Reactivity to Carbon Dioxide in Alzheimer's Disease. A Review" J. Alzheimers Dis. (2013) vol. 35, No. 3, pp. 427-440.
Grossmann, W.M. et al., "The Does-Response Relationship of Acetazolamide on the Cerebral Blood Flow in Normal Subjects" Cerebrovascular Diseases (2000) vol. 10, pp. 65-69.
Güzel-Akdemir, Ö. et al., "Structural Study of the Location of the Phenyl Tail of Benzene Sulfonamides and the Effect on Human Carbonic Anhydrase Inhibition" Bioorganic & Medicinal Chemistry (2013) vol. 21, 6674-6680.
Iadecola, C., "The Pathobiology of Vascular Dementia" Neuron (2013) vol. 80, pp. 844-866.
Regli, F. et al., "Effects of Acetazolamide on Cerebral Ischemia and Infarction After Experimental Occlusion of Middle Cerebral Artery" Stroke (1971) vol. 2, pp. 456-460.
Ringelstein, E.B. et al., "Evaluation of Cerebral Vasomotor Reactivity by Various Vasodilating Stimuli: Comparison of CO2 to Acetazolamide" Journal of Cerebrak Blood Flow and Metabolism (1992) vol. 12, No. 1, pp. 162-168.
Vorstrup, S. et al., "Effect of Acetazolamide on Cerebral Blood Flow and Cerebral Metabolic Rate for Oxygen" J. Clin. Invest. (1984) vol. 74, pp. 1634-1639.
Yang, M-T. et al., "Acetazolamide Impairs Fear Memory Consolidation in Rodents" Neuropharmacology (2013) vol. 67, pp. 412-418.

\* cited by examiner

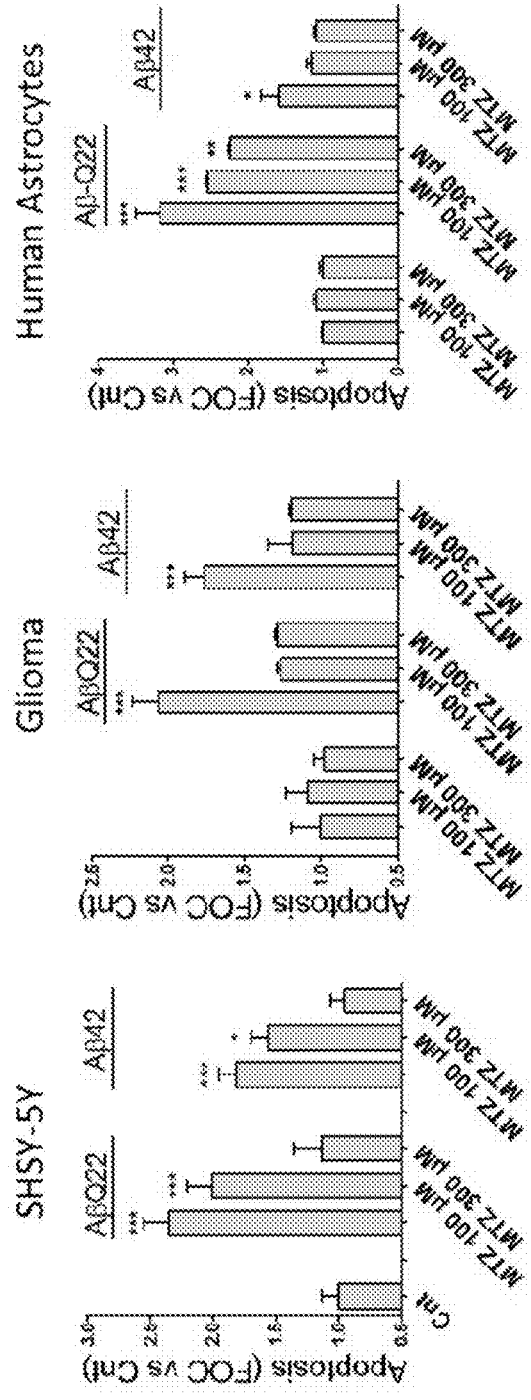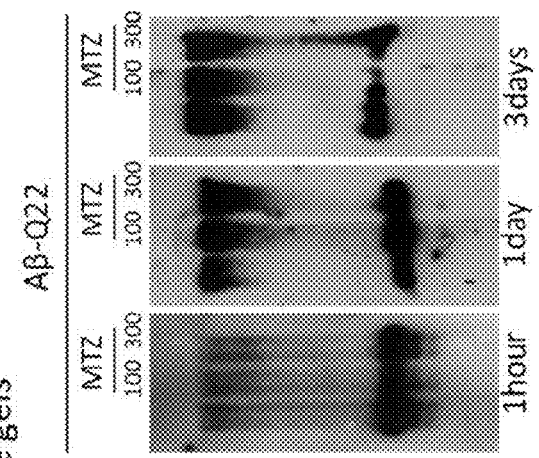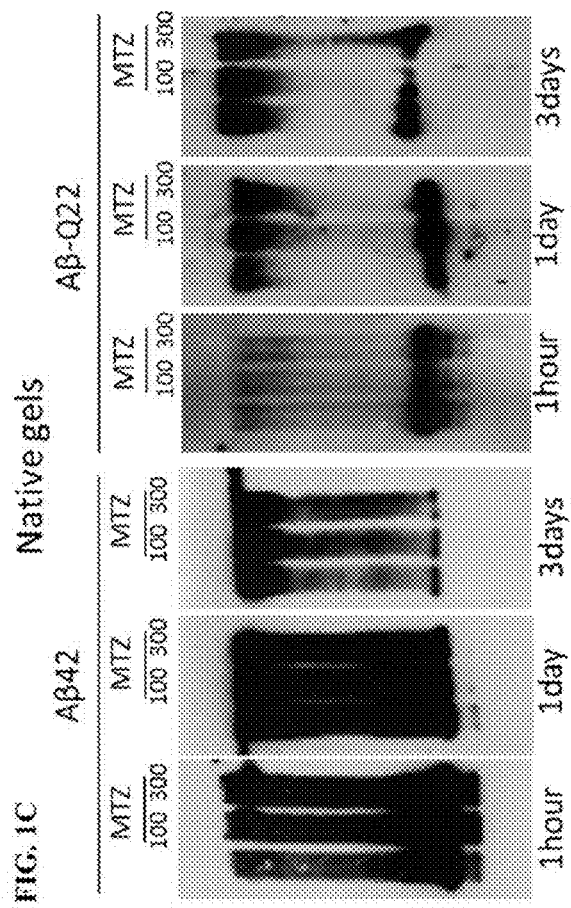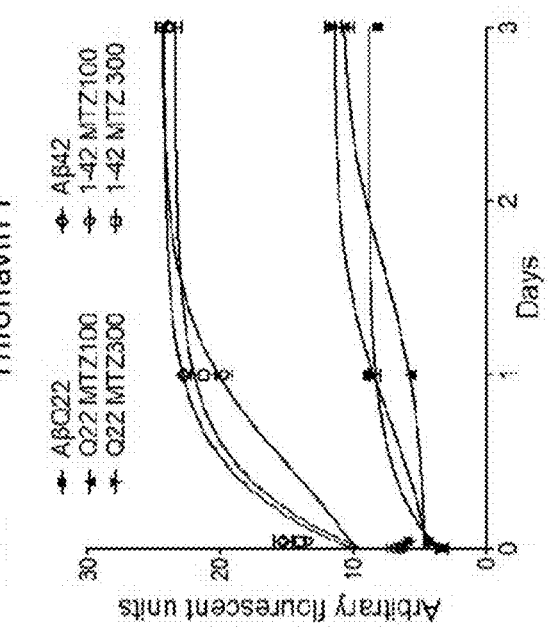
FIG. 1A
FIG. 1B
FIG. 1C

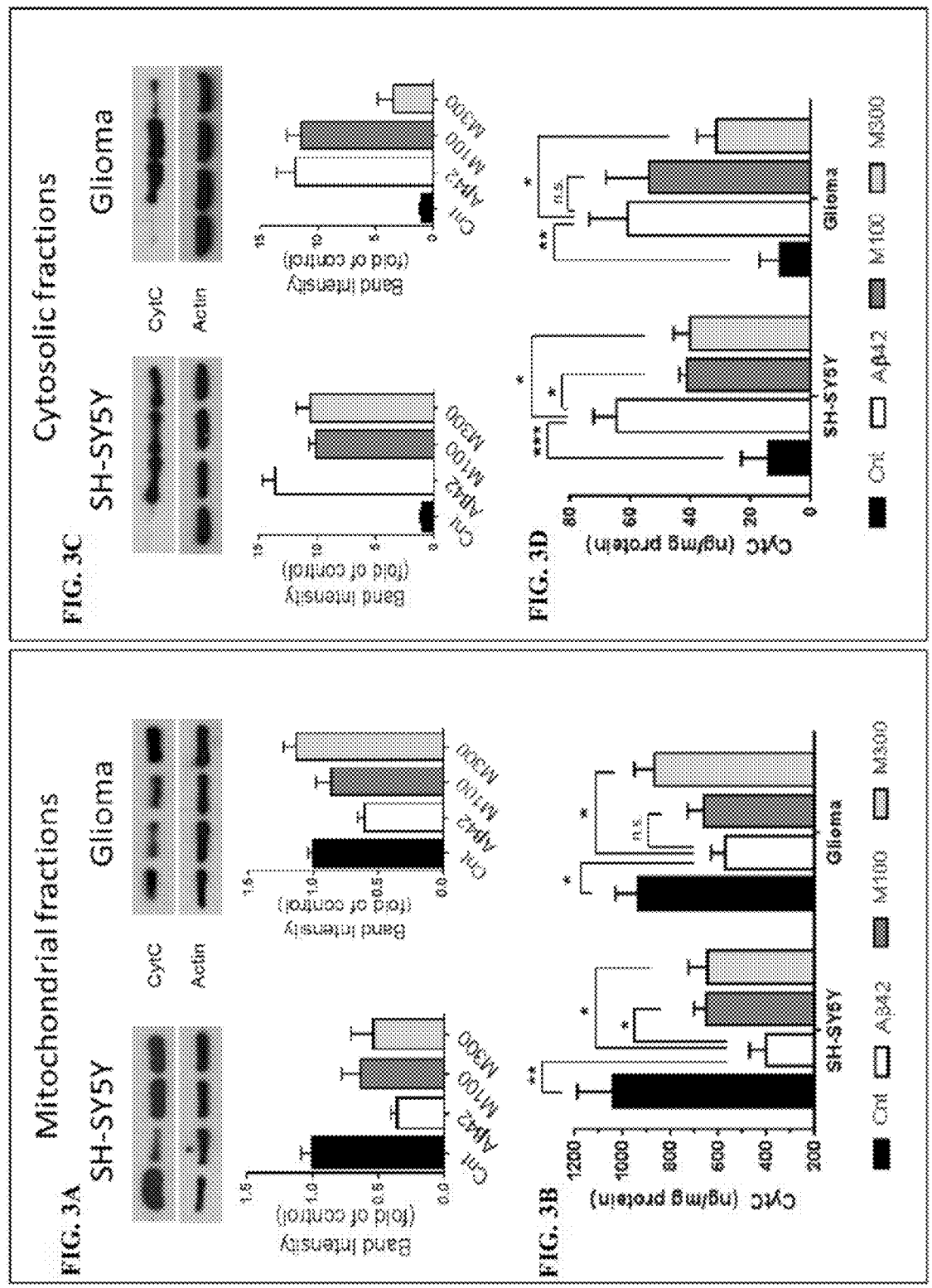

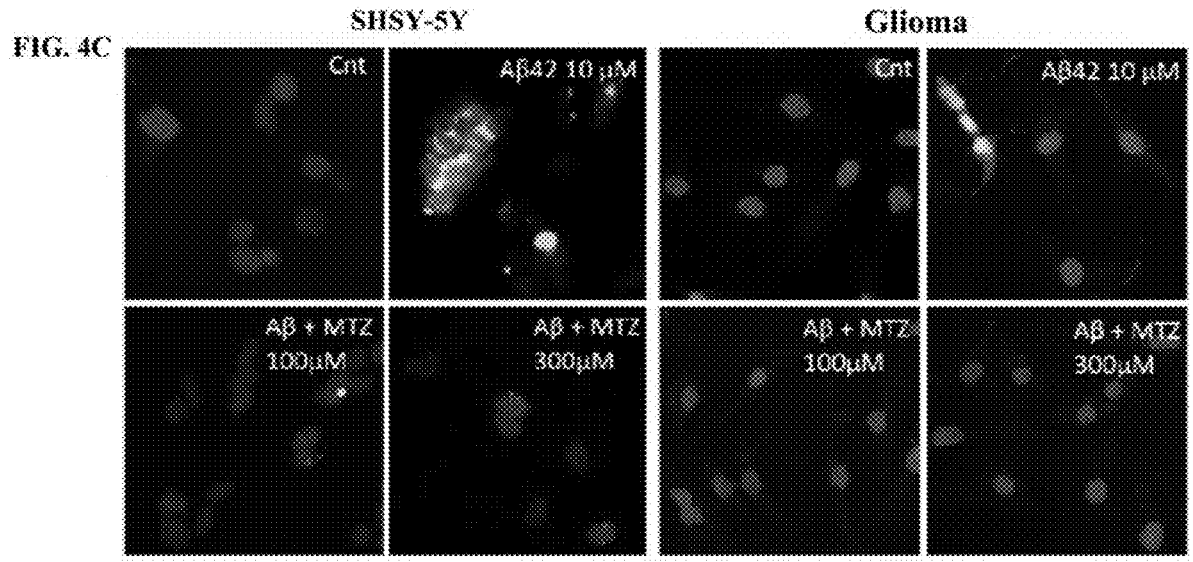
FIG. 4C
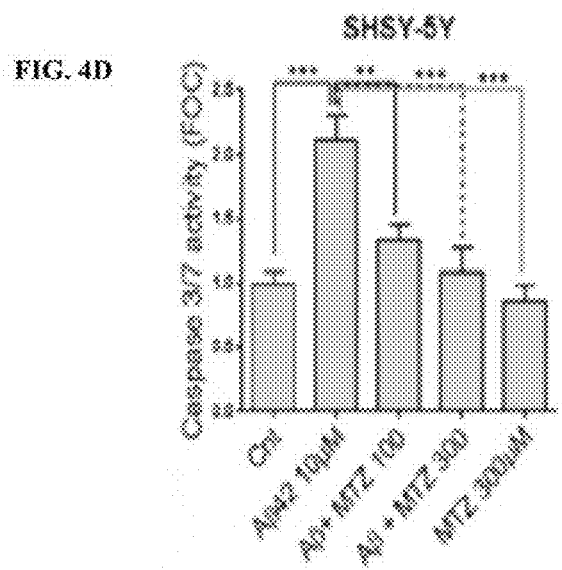
FIG. 4D
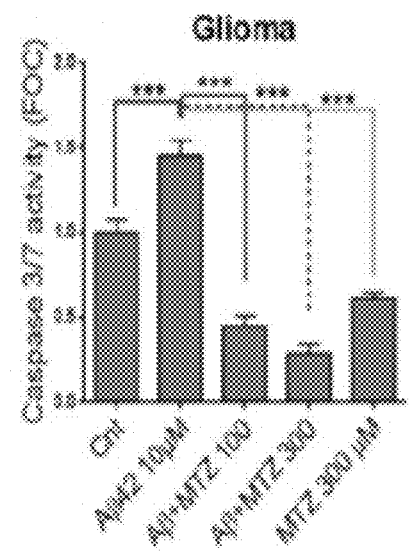

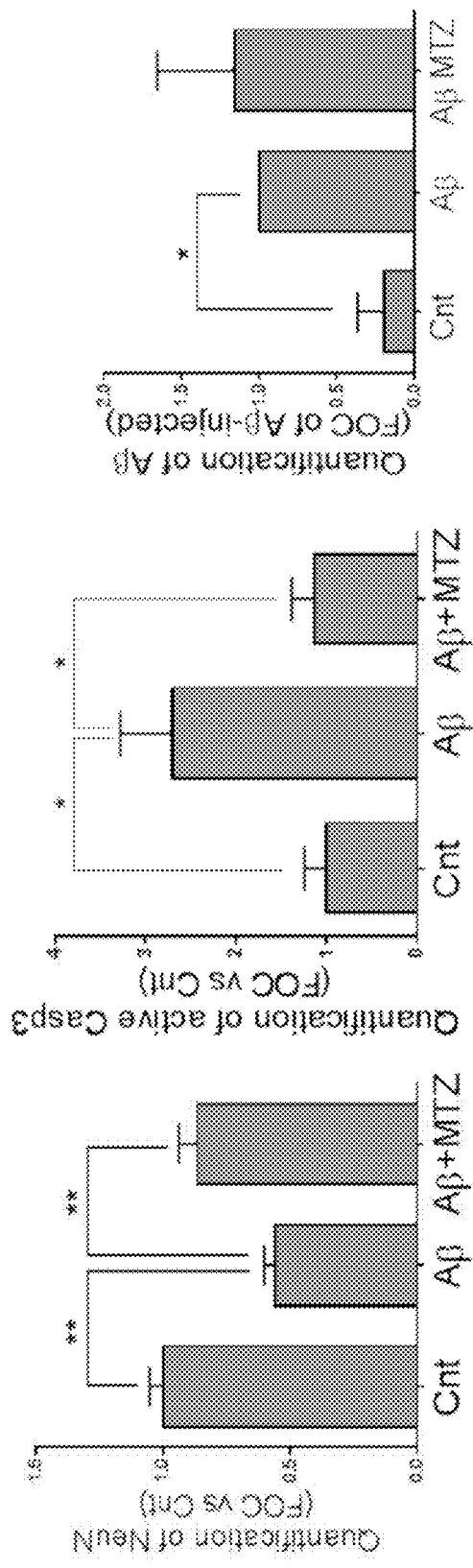
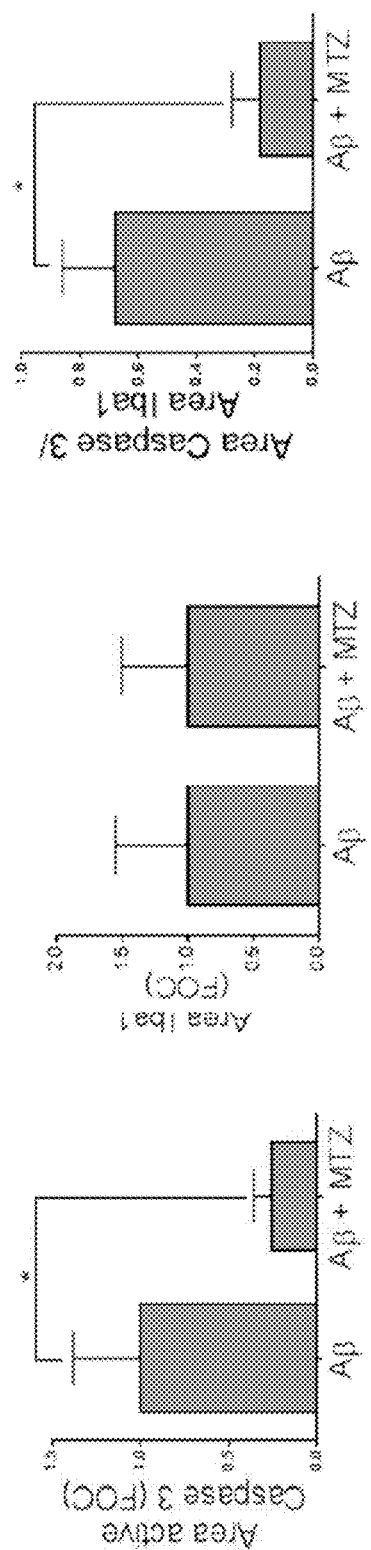
FIG. 9A
FIG. 9B

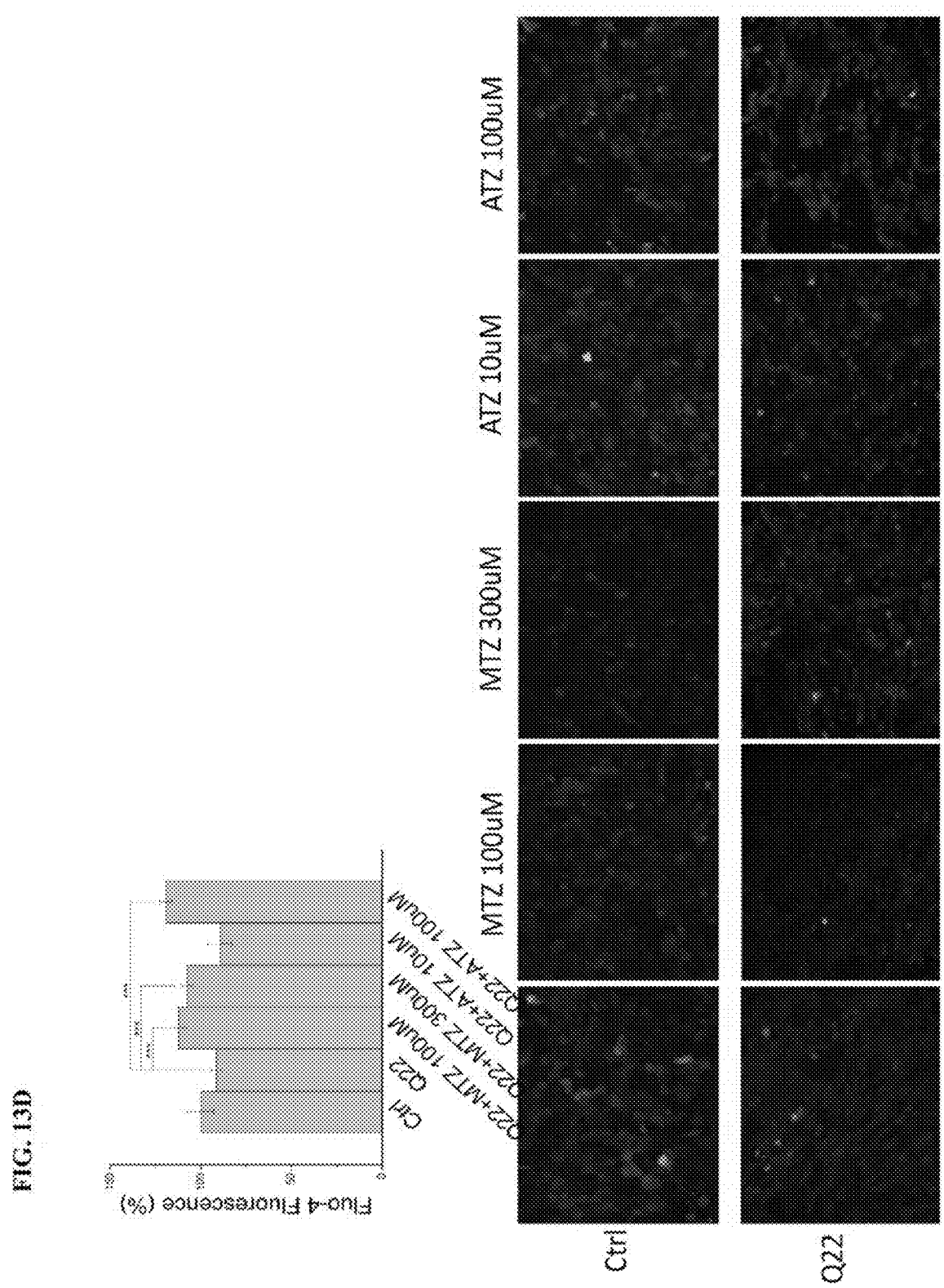

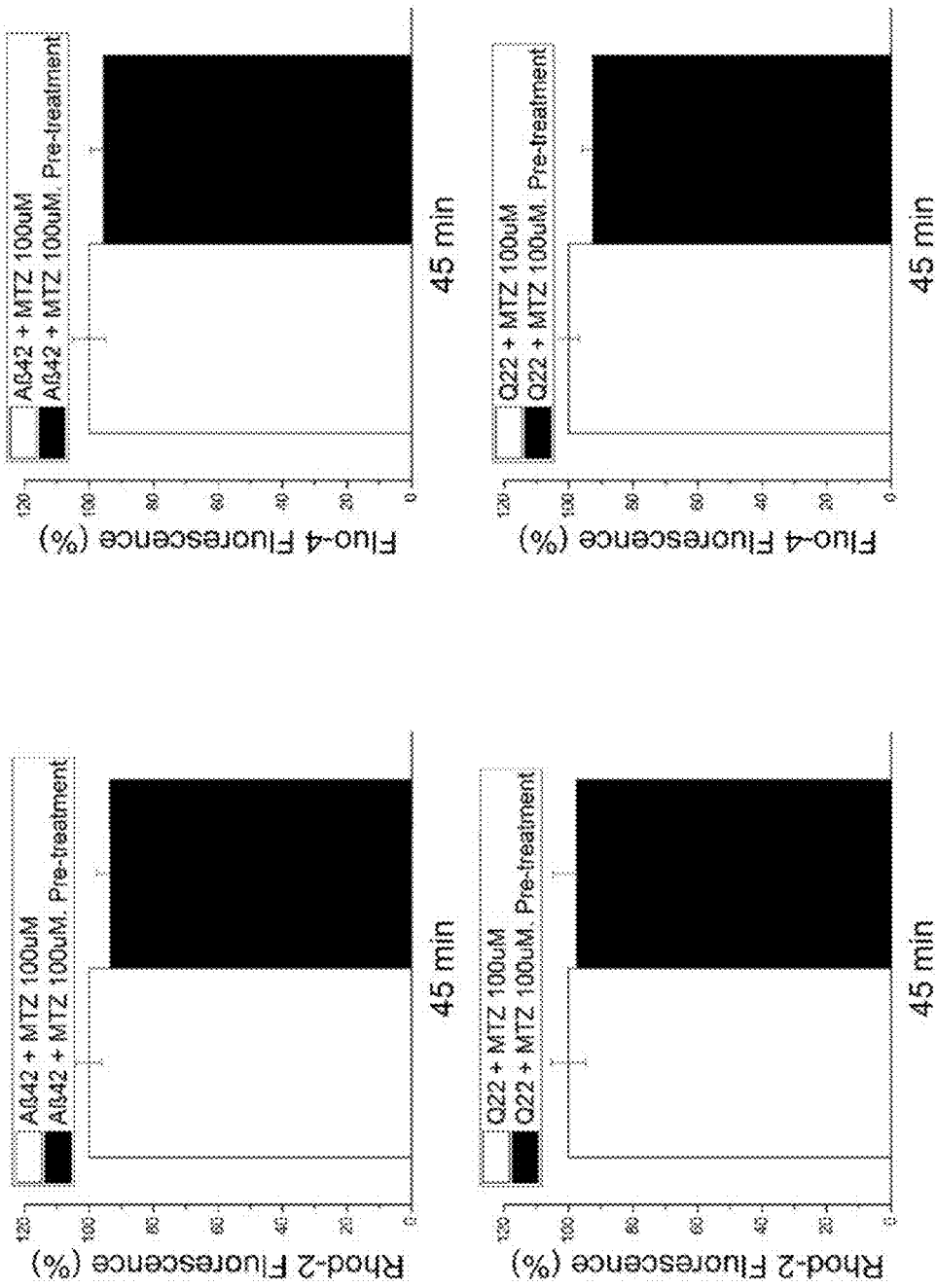

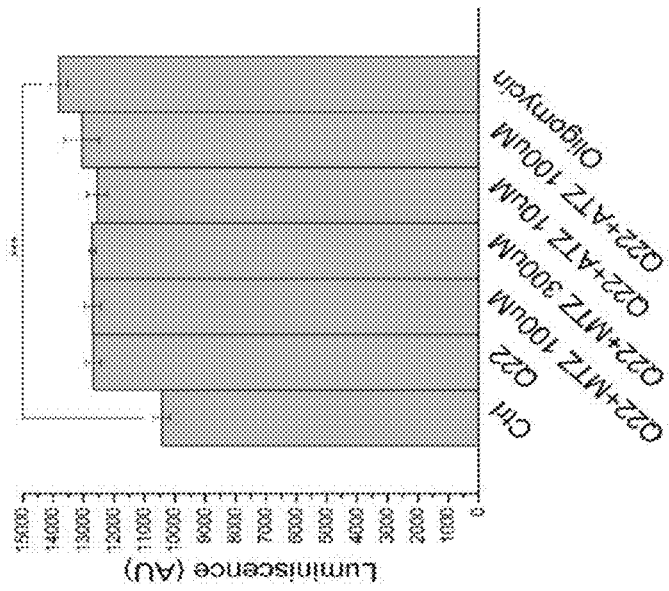
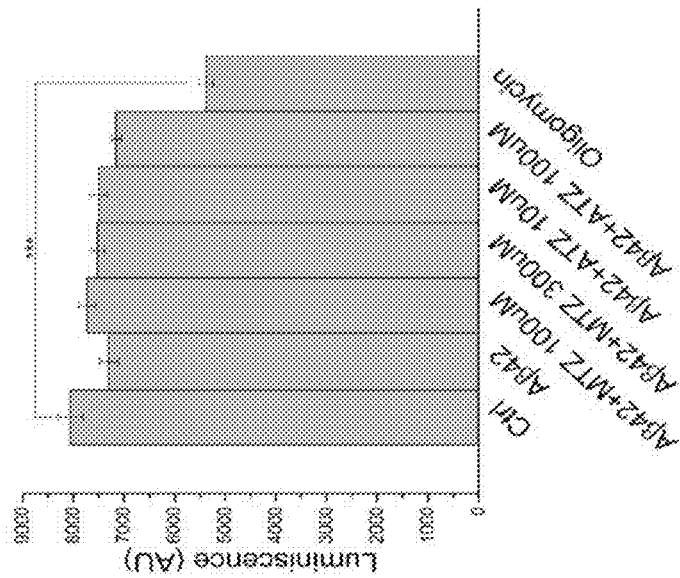
FIG. 15A
FIG. 15B

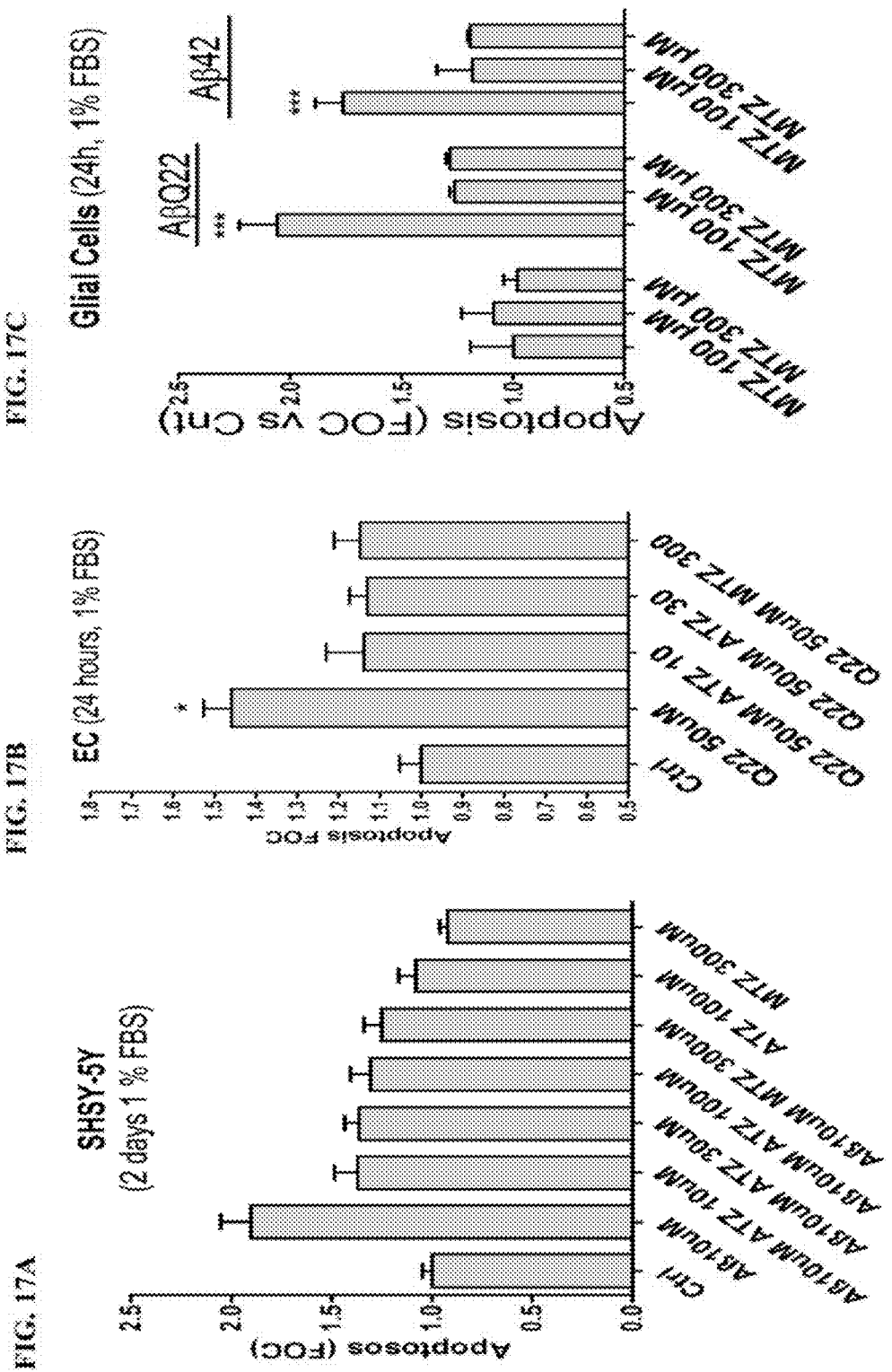

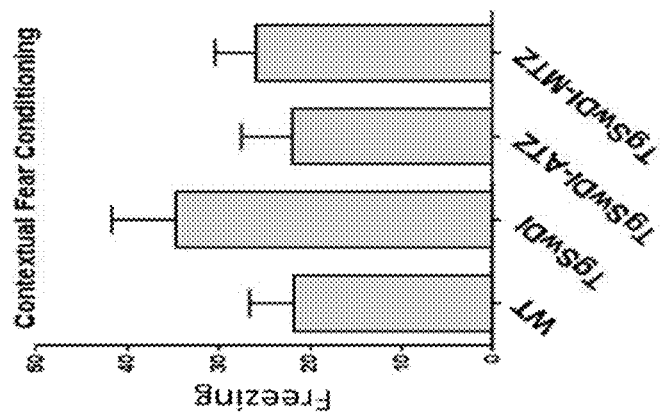
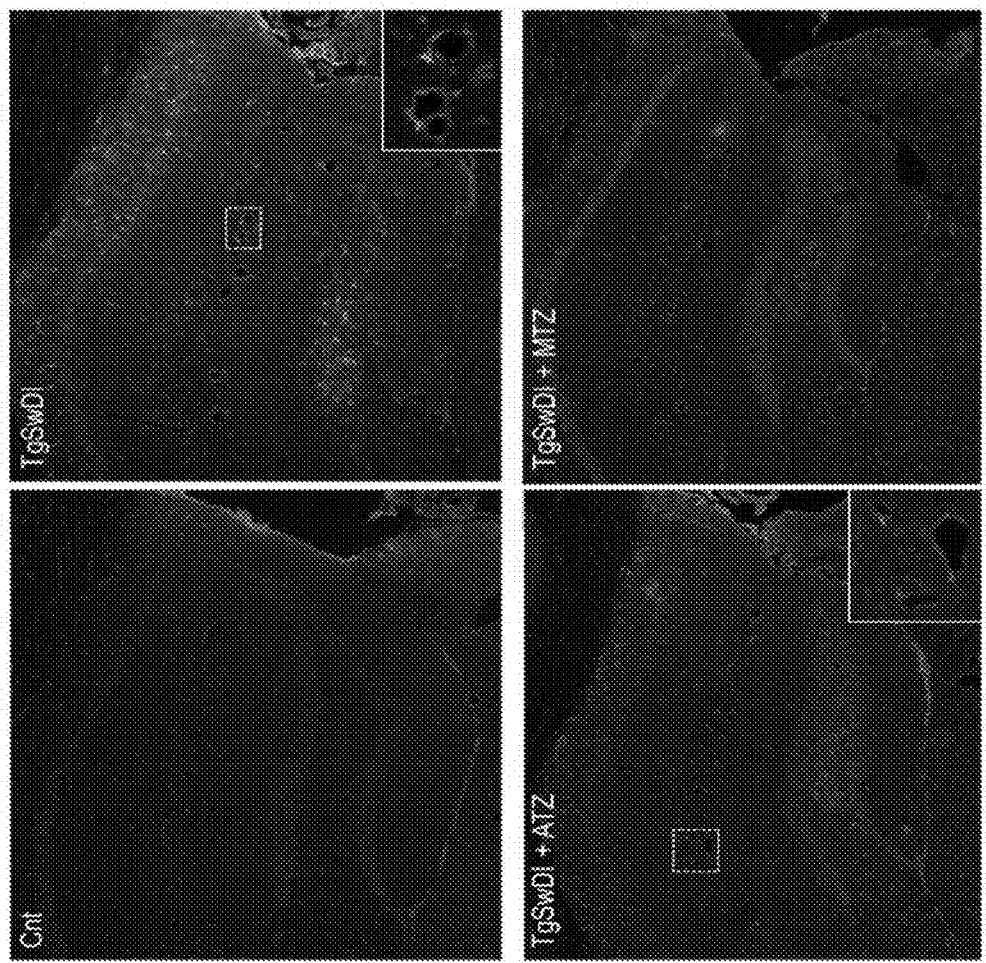

FIG. 18C
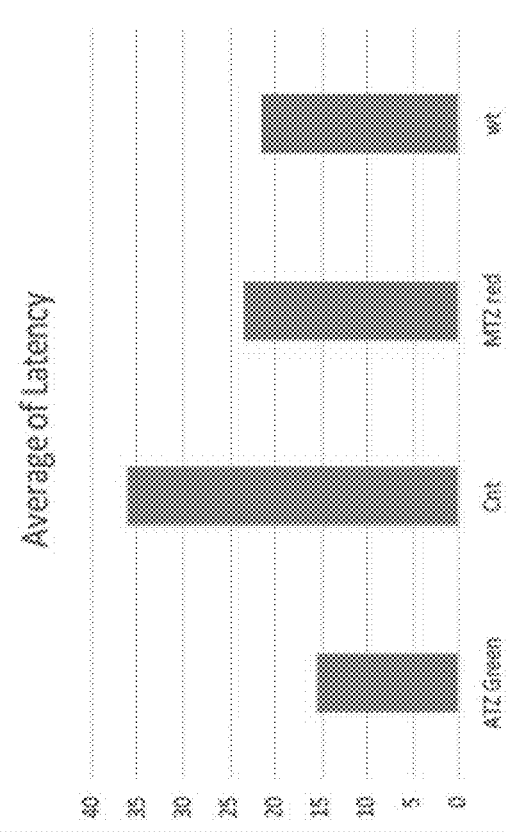
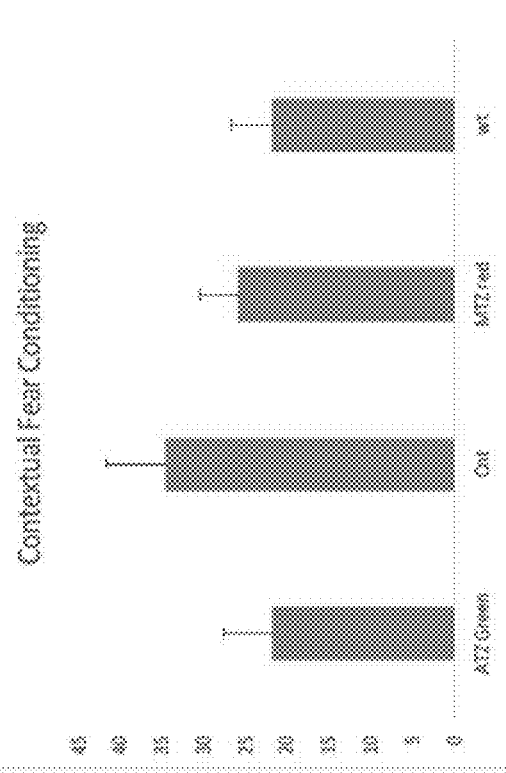

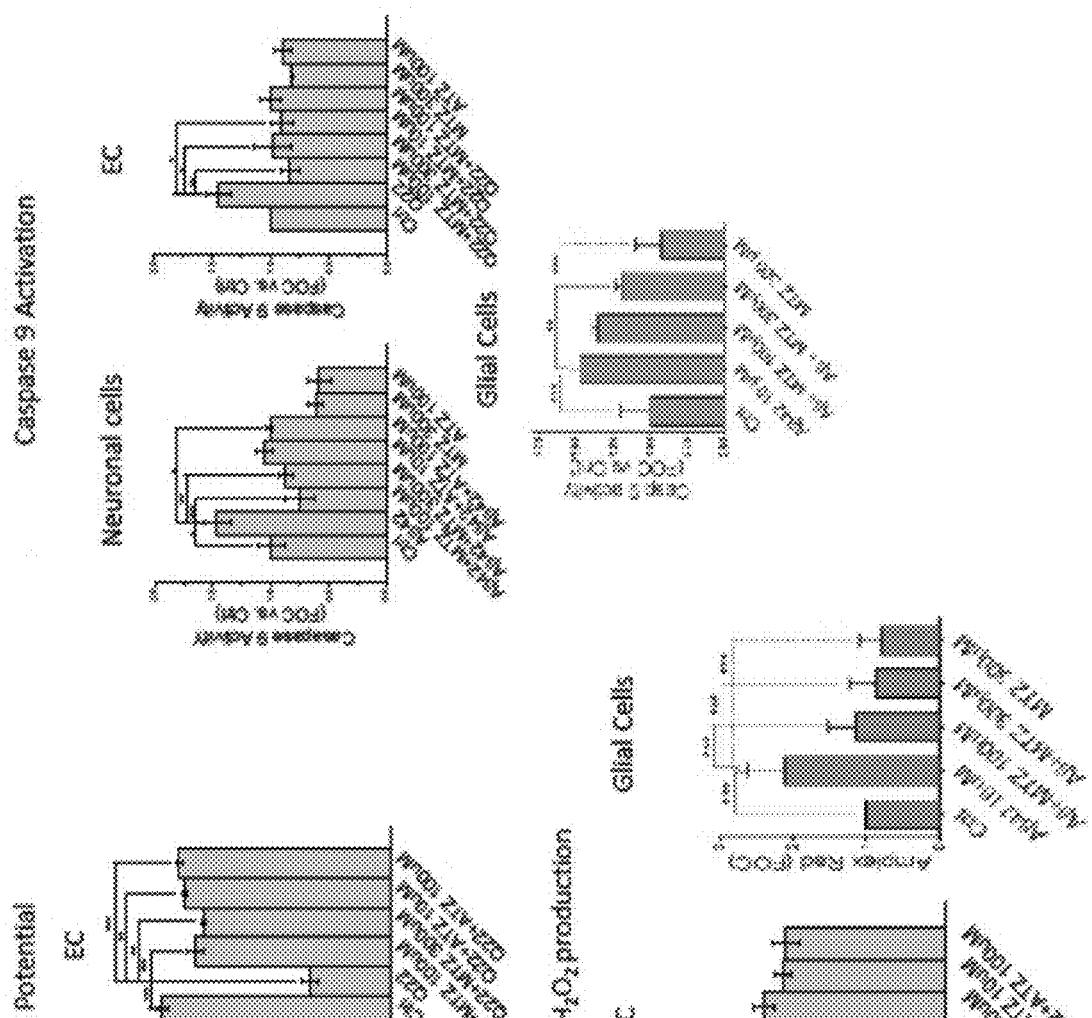
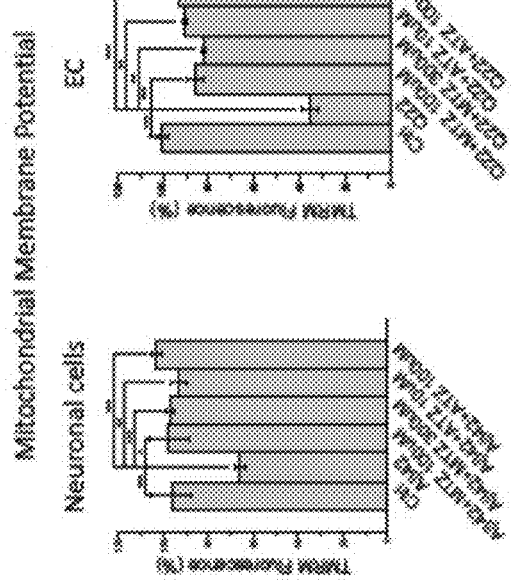
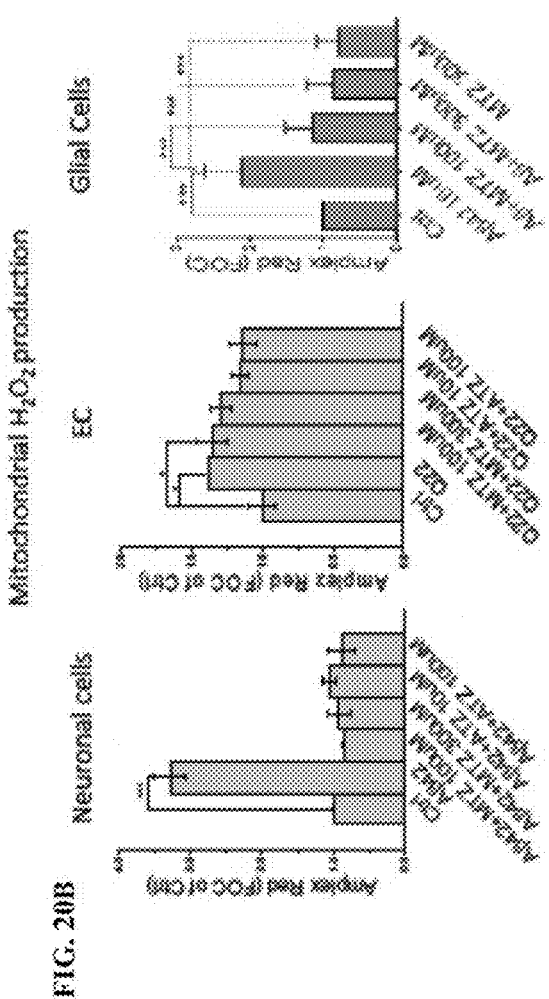
FIG. 20A
FIG. 20B
FIG. 20C

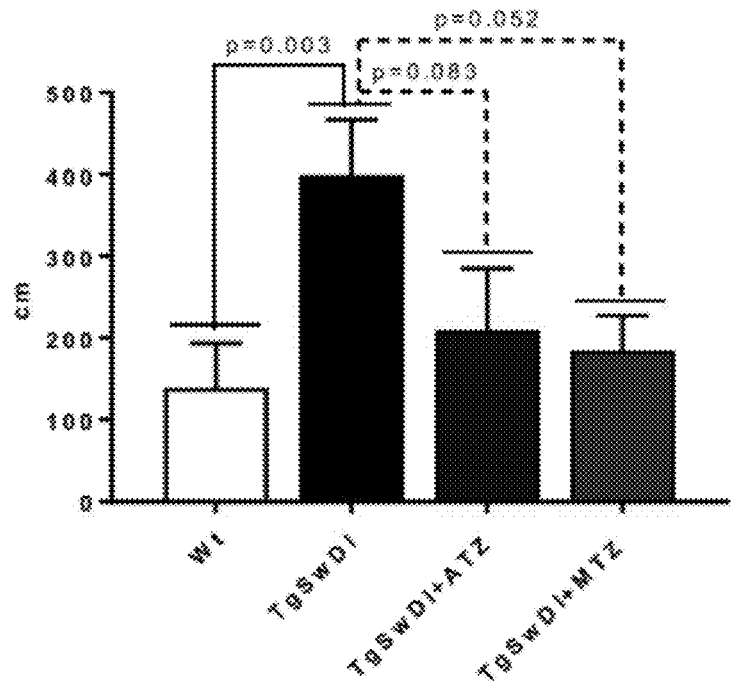
FIG. 26C Distance travelled trial 10
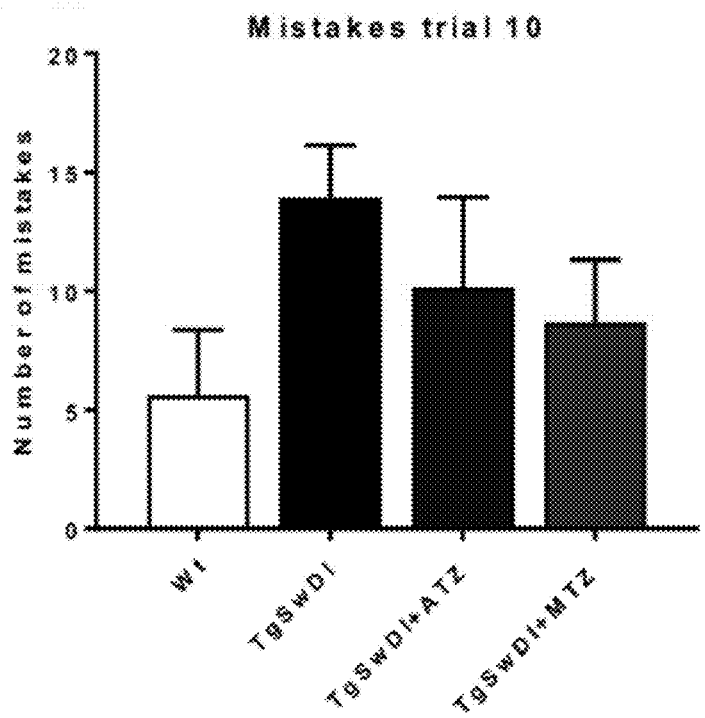
FIG. 26D Mistakes trial 10

USE OF CARBONIC ANHYDRASE INHIBITORS FOR TREATMENT OF NEUROLOGICAL AND PSYCHIATRIC DISORDERS

CROSS-REFERENCE TO RELATED APPLICATIONS

This application claims priority to U.S. Provisional Application No. 62/365,823, filed on Jul. 22, 2016, the disclosure of which is herein incorporated by reference in its entirety.

STATEMENT AS TO FEDERALLY SPONSORED RESEARCH

This invention was made with government support under Grant Nos. NS051715 and AG030539 awarded by the National Institutes of Health—NIA. The government has certain rights in the invention.

FIELD OF THE INVENTION

The invention is directed to the use of carbonic anhydrase inhibitors for treatment of neurological and psychiatric disorders.

BACKGROUND OF THE INVENTION

Alzheimer's disease (AD) is the most prevalent and incident type of dementia in the developed world. An estimated 5.3 million Americans of all ages had AD in 2015. Despite the enormous efforts made by the scientific community in the last decades, an effective therapeutic strategy to prevent or treat AD is still needed. Recently, the importance of mitochondrial dysfunction in the pathogenesis and evolution of AD, as well as other neurodegenerative diseases, has been increasingly recognized [1-5]. Specifically in AD, a clear causal correlation has been found between mitochondrial dysfunction and amyloid β (Aβ)-induced neuronal and vascular degeneration [2, 6-9]. Indeed, mitochondrial pathology and energy metabolism impairment are both present in AD patients and transgenic animal models, appearing during the early stages of the disease and preceding formation of Aβ plaques and memory loss [10-13]. Increments in the apoptotic rate of cell death, closely linked to mitochondrial dysfunction and to the release of pro-apoptotic proteins from the mitochondria, have been found in neurodegenerative diseases such as PD [16], Huntington's disease (HD) [17], and AD [12, 18, 19].

Mitochondrial pathology and energy metabolism impairment are early events in Alzheimer's disease (AD) patients and AD mice models, preceding the formation of amyloid plaques and memory loss [1-4]. Mitochondrial dysfunction has been associated with neurodegeneration and amyloid (Aβ) toxicity in many reports [3, 5], and constitutes a novel and valuable therapeutic target for AD [6-8]. Recent findings in AD mice revealed severe impairments, including reduction of membrane potential and the emergence of dystrophic and fragmented mitochondria, revealing Aβ plaques as focal sources of toxicity [9]. Recent findings in AD mice also revealed the emergence of dystrophic and fragmented mitochondria, as well as increased production of hydrogen peroxide ($H_2O_2$), with Aβ plaques identified as the source of toxicity (Calkins et al., 2011; Xie et al., 2013). Apoptotic cell death and caspase-3 activation have been implicated in the pathogenesis of AD. Up-regulation of pro-apoptotic proteins and DNA fragmentation were also found in the AD brain (Smale et al., 1995; Stadelmann et al., 1999). Release of Cytochrome C (CytC) is one of the main events linking mitochondrial damage and Aβ-mediated apoptotic cell death [10, 11]. Mitochondrial deregulation and the presence of CytC in the cytoplasm is often detected after acute or chronic neurodegenerative insults (Friedlander, 2003; Solesio et al., 2013a; Wang et al., 2003; Zhu et al., 2004; Zhu et al., 2002). CytC release, through activation of the "apoptosome", induces procaspase 9 proteolysis and the formation of mature caspase 9. This enzyme in turn activates caspase 3, which plays important roles in neurodegeneration, particularly in AD (de Calignon et al., 2010; Eckert et al., 2003b; Marques et al., 2003).

Carbonic anhydrases (CA) are a family of enzymes catalyzing the conversion of $CO_2$ and $H_2O$ to bicarbonate and protons (or vice versa), maintaining acid-base balance in blood and other tissues. CA isoforms are present in the mitochondria. CAs have a role in a number of physiological processes such as diuresis, production of body fluids, gluconeogenesis and lipogenesis. 16 mammalian CA isozymes have been discovered, among which CA VA and CA VB are mitochondrial.

SUMMARY OF THE INVENTION

As specified in the Background Section, there is a great need in the art to develop new treatments for neurological and psychiatric disorders, including neurodegenerative diseases. The present invention addresses these and other needs.

In one aspect, the invention provides a method for inhibiting mitochondrial dysfunction in a cell, said method comprising administering to said cell an effective amount of an inhibitor of a carbonic anhydrase, wherein the cell is selected from the group consisting of neuronal cells, glial cells, endothelial cells, and smooth muscle cells.

In another aspect, the invention provides a method for inhibiting caspase activation in a cell, said method comprising administering to said cell an effective amount of an inhibitor of a carbonic anhydrase, wherein the cell is selected from the group consisting of neuronal cells, glial cells, endothelial cells, and smooth muscle cells. In one embodiment, the caspase is caspase 3 and/or caspase 7.

In a further aspect, the invention provides a method for inhibiting Cytochrome C (CytC) release in a cell, said method comprising administering to said cell an effective amount of an inhibitor of a carbonic anhydrase, wherein the cell is selected from the group consisting of neuronal cells, glial cells, endothelial cells, and smooth muscle cells.

In yet another aspect, the invention provides a method for inhibiting cell death, said method comprising administering to said cell an effective amount of an inhibitor of a carbonic anhydrase, wherein the cell is selected from the group consisting of neuronal cells, glial cells, endothelial cells, and smooth muscle cells.

In one embodiment of any of the above methods, the neuronal cell is a dopaminergic neuron. In one embodiment of any of the above methods, the endothelial cell is a microvascular endothelial cell. In one embodiment of any of the above methods, the cell is in a subject (e.g., a subject who has a neurological and/or psychiatric disorder).

In a further aspect, the invention provides a method for inhibiting a neuronal and/or glial and/or vascular degeneration in a subject in need thereof, said method comprising administering to the subject a therapeutically effective amount of an inhibitor of a carbonic anhydrase. In one embodiment, the neuronal and/or glial and/or vascular degeneration is associated with a neurological and/or psychiatric disorder.

In another aspect, the invention provides a method for treating a neurological and/or psychiatric disorder in a subject in need thereof, said method comprising administering to the subject a therapeutically effective amount of an inhibitor of a carbonic anhydrase.

In yet another aspect, the invention provides a method for inhibiting blood-brain barrier permeability associated with a neurological and/or psychiatric disorder in a subject in need thereof, said method comprising administering to the subject a therapeutically effective amount of an inhibitor of a carbonic anhydrase.

Non-limiting examples of neurological or psychiatric disorders treatable by the above methods of the invention include Alzheimer's disease (AD), Mild Cognitive Impairment (MCI), Parkinson's disease (PD; including, among others, human and equine species PD), Huntington's disease (HD), prion-caused diseases, frontotemporal dementia (FTD), Lewy body dementia, vascular dementias, white matter disease, traumatic brain injury, post-traumatic stress, stroke, tauopaties, Down Syndrome, Amyotrophic Later Sclerosis (ALS), chronic traumatic encephalopathy (CTE), progressive supranuclear palsy (PSP), multiple system atrophy (MSA), corticobasal degeneration (CBGD), Pick's disease, olivopontocerebellar atrophy (OPCA), senile dementia of the Alzheimer type, progressive supranuclear palsy (Steel-Richardson-Olszewski), corticodentatonigral degeneration, Hallervorden-Spatz disease, striatonigral degeneration, torsion dystonia (e.g., torsion spasm; dystonia musculorum deformans), spasmodic torticollis and other dyskinesis, familial tremor, Gilles de la Tourette syndrome, cerebellar cortical degeneration, spinocerebellar degeneration (e.g., Friedreich's ataxia and related disorders), Shy-Drager syndrome, spinal muscular atrophy, primary lateral sclerosis, hereditary spastic paraplegia, peroneal muscular atrophy (Charcot-Marie-Tooth), hypertrophic interstitial polyneuropathy (Dejerine-Sottas), chronic progressive neuropathy, pigmentary degeneration of the retina (retinitis pigmentosa), hereditary optic atrophy (Leber's disease), Cognitive Dysfunction Syndrome (e.g., affecting domestic pets), White dog shaker syndrome, degenerative myelopathy, neuroaxonal dystrophy (e.g., in dogs), cerebellar degeneration (e.g., in cats or dogs), and cerebellar abiotrophy.

In one embodiment of any of the above methods involving neurological or psychiatric disorders, the disorder is a neurodegenerative disease (e.g., Alzheimer's Disease (AD), Parkinson's Disease (PD), Huntington's Disease (HD), etc.). In one specific embodiment, the neurodegenerative disease is Alzheimer's Disease (AD).

In a further aspect, the invention provides a method for inhibiting progression from Mild Cognitive Impairment (MCI) or pre-MCI to dementia stage of Alzheimer's Disease (AD) in a subject in need thereof, said method comprising administering to the subject a therapeutically effective amount of an inhibitor of a carbonic anhydrase.

In another aspect, the invention provides a method for inhibiting progression to dementia stage of Alzheimer's Disease (AD) in a subject with Down Syndrome or a subject with familial AD mutation, comprising administering to the subject a therapeutically effective amount of an inhibitor of a carbonic anhydrase.

In yet another aspect, the invention provides a method for inhibiting or reducing an amyloid pathology or proteinopathy in a subject in need thereof, said method comprising administering to the subject a therapeutically effective amount of an inhibitor of a carbonic anhydrase. Amyloid pathologies encompassed by the method of the present invention include pathologies associated with various amyloidogenic peptides, including, for example, A$\beta$, islet amyloid polypeptide (IAPP), $\alpha$-synuclein, AA amyloid, PrP, $\beta$2-microglobulin amyloid, transthyretin, prealbumin, procalcitonin, etc. Non-limiting examples of amyloid pathologies and proteinopathies encompassed by this method include, e.g., sporadic or familial Alzheimer's disease, cerebral amyloid angiopathy (CAA), hereditary CAAs (such as, e.g., Dutch, Italian Flemish, Piedmont, Icelandic, Artic, British or Danish Dementia, Swedish, Iowa, Hungarian, or Ohio mutants), Down syndrome, small vessel disease, diabetes mellitus (including type I diabetes and type II diabetes), inclusion body myositis, cerebral amyloid angiopathy, Lewy Body dementia, Parkinson's disease, Huntington's disease, amyotrophic lateral sclerosis (ALS), prion diseases, and Tauopathies.

In one embodiment of any of the above methods involving administering an inhibitor of a carbonic anhydrase to a subject, such inhibitor is administered chronically, e.g., over a period of more than 6 months or over a period of more than 1 year.

In one embodiment of any of the above methods involving administering an inhibitor of a carbonic anhydrase to a subject, such inhibitor is administered to the subject orally.

In one embodiment of any of the above methods involving administering an inhibitor of a carbonic anhydrase to a subject, the subject is human. In another embodiment, the subject is a veterinary animal.

In one embodiment of any of the above methods of the invention, the carbonic anhydrase is CA VA or CA VB.

In one embodiment of any of the above methods of the invention, the inhibitor of a carbonic anhydrase inhibits CA VA and/or CA VB.

Non-limiting examples of inhibitors of carbonic anhydrases useful in the methods of the invention include acetazolamide (ATZ), methazolamide (MTZ), and ethoxzolamide (ETZ), sulthiame, dichlorophenamide, dorzolamide, brinzolamide, indisulam, topiramate, zonisamide, sulpiride, COuMATE, EMATE, celecoxib, valdecoxib, saccharin, chlorothiazide, hydrochlorothiazide, hydroflumethiazide, bendroflumethiazide, trichloromethiazide, polythiazide, quinethazone, metolazone, chlorthalidone, indapamide, furosemide, bumetanide, and various analogs and derivatives thereof.

In one embodiment of any of the above methods of the invention, the inhibitor of a carbonic anhydrase is not methazolamide (MTZ).

In one embodiment of any of the above methods of the invention, the inhibitor of a carbonic anhydrase is methazolamide (MTZ) or a derivative or an analog thereof. In one embodiment of any of the above methods involving administering to a subject, methazolamide (MTZ) or a derivative or an analog thereof is administered to the subject in a dose of 0.1-20 mg/kg/day. In another embodiment, methazolamide (MTZ) or a derivative or an analog thereof is administered to the subject in a dose of 0.1-1 mg/kg/day.

In one embodiment of any of the above methods of the invention, the inhibitor of a carbonic anhydrase is acetazolamide (ATZ) or a derivative or an analog thereof. In one embodiment of any of the above methods involving administering to a subject, acetazolamide (ATZ) or a derivative or an analog thereof is administered to the subject in a dose of 0.1-20 mg/kg/day. In another embodiment, acetazolamide (ATZ) or a derivative or an analog thereof is administered to the subject in a dose of 0.1-1 mg/kg/day.

These and other aspects of the present invention will be apparent to those of ordinary skill in the art based on the following description, claims and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1C. Methazolamide prevents DNA fragmentation in neuronal and glial cells without affecting Aβ aggregation. Cultures of neuronal SHSY-5Y cells, glioma cells and normal human astrocytes were challenged with 50 μM Aβ40-Q22 or 10 μM Aβ42, in the presence or absence of methazolamide (MTZ) 100 or 300 μM (FIG. 1A). Apoptosis was evaluated as presence of fragmented nucleosomes by Cell Death Detection ELISA$^{plus}$ after 1 day in SHSY-5Y cells and astrocytes and after 3 days in glioma cells. Results are expressed as fold of change compared with no-peptide controls (Cnt). Data are representative of at least three independent experiments performed in duplicate. Bars represent means+/−S.D. *P<0.05, P<0.001, *P<0.0001 compared to Cnt cells in absence of peptides and MTZ. Thioflavin T binding of Aβ42 and Aβ40-Q22 (both aggregated at 500 μM concentration for up to 3 days) in the presence or absence of MTZ (1000 μM or 3000 μM) (FIG. 1B). Fluorescence evaluation (excitation 435 nm/emission 490 nm) of Thioflavin T at different time points during peptide aggregation was performed as described in Materials and Methods. Thioflavin T binding, indicating peptide oligomerization/fibrillization was not significantly affected by MTZ. Data is representative of experiments performed 3 times in duplicate. Native Western Blotting analysis. Aβ peptides were aggregated for different time points (1 hour, 1 day and 3 days) in the presence or absence of MTZ (FIG. 1C). Samples were separated in non-denaturing 5-30% gradient gels, electrotransferred to nitrocellulose, and probed with an antibody recognizing Aβ. Electrophoretic mobility at each aggregation time point was not affected by the presence of MTZ. Data are representative of 3 different experiments.

FIGS. 3A-3D. Evaluation of the preventive effect of MTZ on Aβ-mediated mitochondrial CytC release by Western blot and ELISA. Neuronal SH-SY5Y and glioma cells were challenged with Aβ42 (10 μM; 24 h) in the presence or absence of MTZ (100 and 300 μM) and subsequently subjected to subcellular fractionation. CytC was evaluated in mitochondrial and cytosolic extracts by WB and ELISA. (FIG. 3A-FIG. 3C) Western blot analysis of mitochondrial (FIG. 3A) and cytosolic (FIG. 3C) extracts. After electrophoretic separation of the respective subcellular fractions and electrotransfer to PVDF, membranes were probed for CytC and β-actin as loading control. Band intensities after normalization to the respective loading controls are illustrated in the bar-graphs below the corresponding WB. Each WB is representative of duplicate independent experiments. (FIG. 3B-FIG. 3D) CytC quantitated by ELISA in the mitochondrial (FIG. 3B) and cytoplasmic (FIG. 3D) extracts. Bars represent mean±SD of triplicate experiments. * indicates p<0.05,  p<0.01, and * indicates p<0.001.

FIGS. 4A-4D. Effect of MTZ on Aβ-mediated caspase activation and $H_2O_2$ production. Caspase 9 activity in neuronal and glial cells was measured by luminescence (FIG. 4A). MTZ inhibited the activation of caspase 9 induced by incubation with 100 μM Aβ42 for 24 hours in both cell types. Mitochondria were isolated after cell treatment with Aβ42 in the presence or absence of MTZ, and mitochondrial $H_2O_2$ production was quantified using Amplex Red Hydrogen Peroxidase/Peroxidase Assay as specified in Methods (FIG. 4B). Results are expressed as fold change in $H_2O_2$ production compared with no-peptide controls (Cnt). MTZ inhibited Aβ-mediated caspase 3 activation, visualized by anti-active caspase 3 staining after 24 hours treatment with 10 μM Aβ42 (FIG. 4C). Green fluorescence highlights cells presenting active caspase 3. Nuclei were stained in blue with DAPI. Magnification: 20×. Caspase 3/7 activity in neuronal and glial cells was measured by luminescence (FIG. 4D). MTZ inhibited the activation of caspase 3/7 after 24 hours in both cell types. For FIG. 4A, FIG. 4B, FIG. 4C, and FIG. 4D, data are representative of at least three independent experiments performed in duplicate. Bars represent means+/−S.D. * P<0.05,  P<0.01, * P<0.0001.

FIGS. 9A-9B. Quantification of the protective effect of MTZ in the in vivo experiments. Immunostaining in proximity of the injection site in mice injected with Aβ in the presence or absence of MTZ was quantified with Image J. The total area of each specific staining is represented in the graphs. Loss of hippocampal NeuN staining (FIG. 9A, left panel) in the Aβ-injected hemisphere (compared to the contralateral hemisphere) is prevented by MTZ. Caspase 3 activation (central panel) is increased in the Aβ injected hippocampus and is prevented by MTZ. Staining of Aβ (right panel) is low in the contralateral (Cnt) hemisphere and similarly increased in the hemisphere subjected to injection of Aβ in the presence or absence of MTZ. Quantification of active caspase 3 staining, IBA1 staining, and the ratio between active caspase 3 and IBA1 staining in microglia are represented respectively in the left, central and right panel (FIG. 9B). For all experiments (FIG. 9A and FIG. 9B), quantification was performed in brain slices of 3 or more different animals. * indicates $p<0.05$; ** indicates $p<0.01$.

(FIG. 10C) Effect of FCCP addition to SH-SY5Y and D3 cell cultures. Mitochondrial membrane depolarization in response to Aβ and its inhibition in the presence of CAIs was measured by tetramethylrhodamine methyl ester (TMRM) in (FIG. 10A) SH-SY5Y neuronal cells and (FIG. 10B) D3 cerebral microvascular endothelial cells. The depolarization is counteracted by the CAIs methazolamide (MTZ) and acetazolamide (ATZ) in both cases. In FIGS. 10A-10B ATZ is effective at concentrations 10 times lower than MTZ. Mitochondrial membrane depolarization in response to Aβ and its inhibition in the presence of an inactive analog of ATZ was measured by TMRM in SH-SY5Y neuronal cells (FIG. 10D).

In FIGS. 11A-11B ATZ is effective at concentrations 10 times lower than MTZ.

FIG. 13A-13F. Effect of Aβ on calcium homeostasis. Graphs and images showing mitochondrial calcium concentration in (FIG. 13A) SH-SY5Y cells and in (FIG. 13B) D3 ones and cytoplasmic calcium concentration in the same cell models (FIG. 13C and FIG. 13D, respectively). (FIG. 13E) Effect of the pre-treatment of the cells with the Aβ peptide, in both mitochondrial and cytoplasmic calcium concentration. (FIG. 13F) Effect of Ionomycin in both mitochondrial and cytoplasmic calcium concentration after the treatments.

FIGS. 15A-15B. ATP Production. Graphs showing ATP production in response to the peptide or the peptide and drug treatment (FIG. 15A) SH-SY5Y and (FIG. 15B) D3 cell cultures.

FIGS. 17A-17C. Apoptotic cell death in response to Aβ is prevented by ATZ and analog CAIs in neuronal, endothelial and glial cells. Apoptosis in response to Aβ and its inhibition in the presence of CAIs was measured by Cell death ELISA plus (Roche) in (FIG. 17A) SH-SY5Y neuronal cells, (FIG. 17B) D3 endothelial cells and (FIG. 17C) glial cells. Apoptosis is prevented by the CAIs methazolamide (MTZ) and acetazolamide (ATZ).

FIGS. 18A-18C. Effect of ATZ and MTZ on hippocampal amyloid pathology and caspase 3 activation in TgSwDi mice. Immunostaining was performed in control (Cnt) mice and TgSwDI ((Swedish-Dutch-Iowa mice, a model of vascular and parenchymal amyloidosis) in the presence or absence of MTZ or ATZ. Mice were treated with the drugs incorporated in their diet starting at 5-6 months of age and sacrificed at 9 months. Aβ is stained in red, active caspase 3 in green, and nuclei are stained in blue by DAPI (FIG. 18A). Colocalization of caspase 3 and aβ results in a yellow staining. The top left panel represents the control WT mouse. In the top-right panel, the hippocampus of a 9 months old TgSwDI mouse shows extensive aβ deposition in vessels and diffused parenchimal plaques. Caspase 3 activation is evident in vessels and neuronal and glial cells presenting aβ deposition (yellow). Caspase activation is prevented by ATZ (bottom left panel). In mice treated with MTZ, a reduced deposition of Aβ can be also observed. MTZ and ATZ also had a normalizing effect on the increase of freezing shown by TgSwDI mice in contextual fear conditioning (FIG. 18B). The increase in caspase 3 activation induced by Aβ is inhibited in mice treated with MTZ and ATZ. Moreover, mice treated with MTZ in particular, show a reduction in Aβ deposition compared to TgSwDI mice, likely due to the known increase in CBF by CAIs. A short-term treatment (3 months) with CAIs also improved freezing in fear conditioning and latency (trial 7-10 shown) in the Barnes maze (FIG. 18B-18C).

FIGS. 20A-20C. Effect of CAIs on Aβ-mediated loss of mitochondrial membrane potential, caspase activation and $H_2O_2$ production. Mitochondrial membrane potential was measured by TMRM in neuronal and endothelial cells after treatment with Aβ in the presence or absence of MTZ or ATZ (FIG. 20A). Mitochondria were isolated after cell treatment with Aβ in the presence or absence of MTZ or ATZ, and mitochondrial $H_2O_2$ production was quantified using Amplex Red Hydrogen Peroxidase/Peroxidase Assay (FIG. 20B). Results are expressed as fold change in $H_2O_2$ production compared with no-peptide controls (Cnt). Caspase 9 activity in neuronal and glial cells was measured by luminescence (FIG. 20C). MTZ inhibited the activation of caspase 9 induced by incubation with 10 μM Aβ42 for 24 hours in both cell types.

FIGS. 26A-26D. Barnes Maze testing (spatial memory). Spatial memory was assessed by Barnes Maze in younger (8-9 months) and older (15-16 months) Tg-SwDI and C57/B6 control mice. Both MTZ and ATZ were given at 15-20 mg/kg/day (incorporated in the diet). Drugs were incorporated in the mouse diet at 100 ppm by TestDiets. Time administered was 3 months for the young, and 8 months for the old (15 months-old mice). The presented data are from a probe test session in which navigation to the escape hole location (green arrows) was assessed following 10 prior training trials. Heat maps illustrating the navigation patterns of representative (median performance) 15-16-month old C57/B6 (n=10), Tg-SwDI (n=19), Tg-SwDI+MTZ (n=12), and Tg-SwDI mice+ATZ (n=9) (FIG. 26A). Mean (+SEM) of the total number of mistakes (left) and distance traveled (right) prior to trial completion (FIG. 26B). Data were averaged across roughly equivalent numbers of males and females in each group as there were no significant effects of gender. *15-16-month old Tg-SwDI mice were significantly impaired relative to younger Tg-SwDI mice (p<0.05) as well as to older C57/B6 controls (p<0.05). A 300-sec probe trial, conducted 1 h after the final training trial, was identical to the training trials except that all 12 holes were blocked. The mouse was therefore unable to escape the maze during the probe trial. Distance for TgSwDI treated with MTZ and ATZ in the diet for 8 months was not significantly higher than WT mice, suggesting a protective effect of the drugs against loss of spatial memory. Results of Barnes Maze testing in TgSwDI mice treated with MTZ and ATZ for 8 months and tested at 15-16 months (FIGS. 26C-26D). Distance traveled in trial 10 (last trial), representing memory loss on the maze, was higher in TgSwDI mice than WT (FIG. 26C). Distance for TgSwDI mice treated with MTZ and ATZ was not significantly higher than WT mice, suggesting that both MTZ and ATZ restore memory to levels similar to the controls (FIG. 26D).

FIGS. 28A-28B represent an area of the hippocampus including the dentate gyrus at respectively 10× (FIG. 28A) and 20× (FIG. 28B) magnification, in 16 months old TgSwDI. Thioflavin S bright green fluorescence stained amyloid deposits. There was an effect of the drugs on amyloid deposition, with both Methazolamide (MTZ) and acetazolamide (ATZ) inducing a decrease in the hippocampal deposition of Amyloid beta (Aβ). Mice were subjected to the drug regimen (incorporated in their diet) for 8 months. FIG. 28C represents the accumulation of amyloid deposits stained by Thioflavin S in the cortex (top panels) and in the thalamic region (bottom panels), in 16 months old mice subjected to drug treatment as above. ATZ and MTZ also reduced deposition in these brain areas. FIG. 28D shows Thioflavin S staining in age-matched Wild Type (WT) mice as a negative control. No amyloid deposition was observed in the WT brain, either in the hippocampus, the cortex, or the thalamus.

DETAILED DESCRIPTION OF THE INVENTION

Definitions

Figure 2:
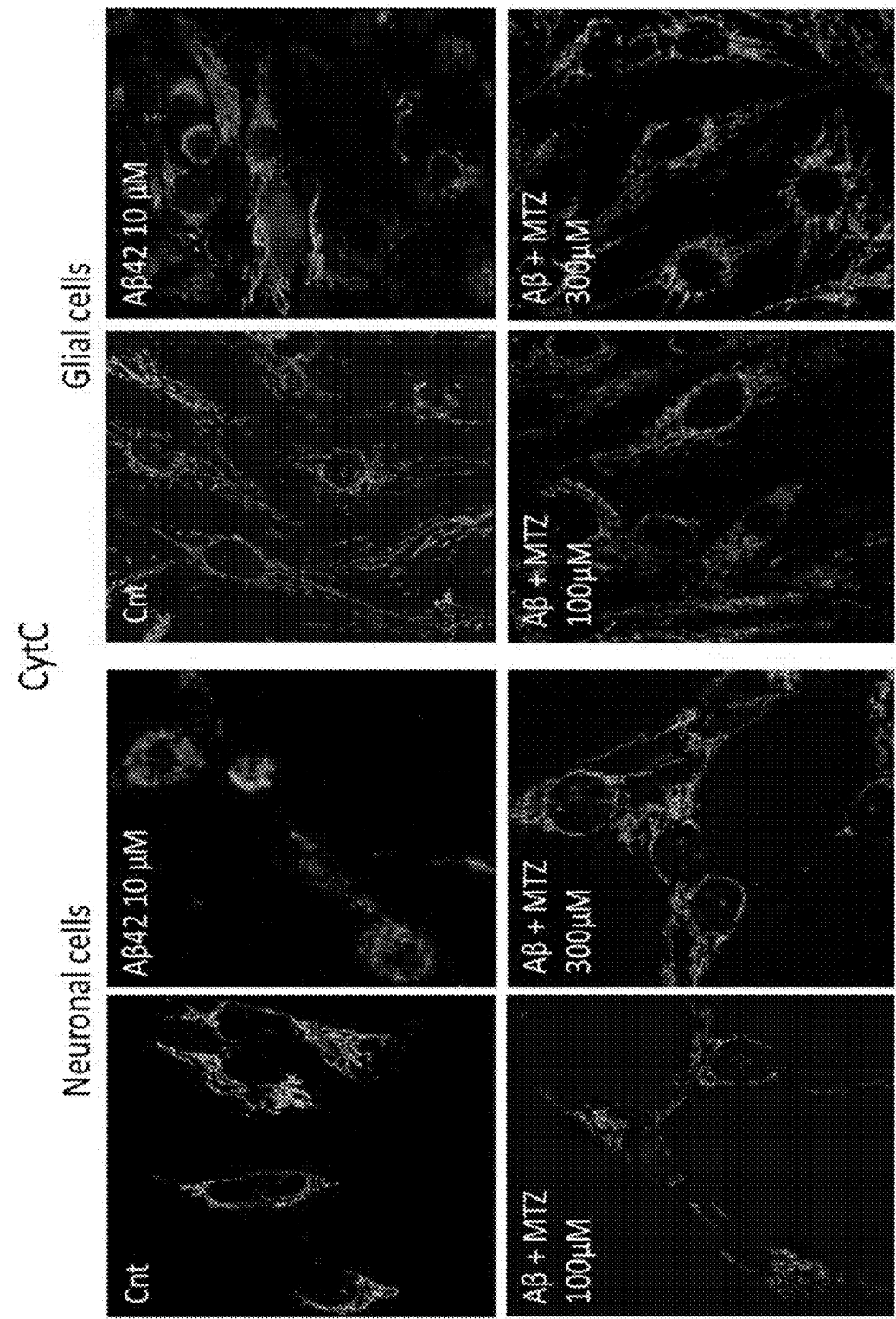
FIG. 2. Methazolamide inhibits mitochondrial CytC release in neuronal and glial cells challenged with Aβ. Neuronal SHSY-5Y (left panel) and Glioma cells (right panel) were challenged with 10 μM Aβ42 for 24 hours. Green fluorescence highlights CytC staining; chain-like appearance of CytC represents mitochondrial localization, whereas more diffuse green staining indicates release into the cytoplasm. Magnification 40×. Cnt=control cells in absence of peptide and MTZ. Images are representative of 3 independent experiments.

The term "pre-Mild Cognitive Impairment" or "pre-MCI" refers to asymptomatic, preclinical phase of Alzheimer's Disease (AD) and other neurodegenerative diseases leading to dementia (Jack et al., Alzheimer's and Dementia. 2011, Epub April 19; Khachaturian Z S, 2011 Alzheimer's and Dementia. 7, 253-256). The first symptomatic stage of Alzheimer's disease that is manifested by mild clinical symptoms is "Mild Cognitive Impairment (MCI)", which is usually defined as an intermediate state between normal aging and dementia (DeCarli, Lancet Neurol., 2003, 2:15-21; Stephan et al., Alzheimer's Res Therapy, 2009, 1:1-9; Apostolova et al., Human Brain Mapping, 2010, 31:786-797). On average, MCI patients convert to dementia at a rate of 10-15% annually (Petersen et al., Arch Neurol. 2001, 58:1985-1992; Apostolova et al., Human Brain Mapping, 2010, 31:786-797). Disease progression varies for AD patients from slow to intermediate and rapid (Doody et al., Alzheimer's Res Therapy, 2010, 2:2-10). Clinically MCI is not a homogeneous pathology and can be described as two conditions, with amnestic symptoms (aMCI) and without amnestic symptoms (Dlugaj et al., Dement Geriatr Cogn Disord., 2010, 30:362-373; Brooks, Loewenstein, Alzheimer's Res Therapy, 2010, 2:28-36).

In the context of the present invention insofar as it relates to neurodegeneration or any of the specific disease conditions recited herein, the terms "treat", "treatment", and the like mean to relieve or alleviate at least one symptom associated with such condition, or to slow or reverse the progression of such condition. Within the meaning of the present invention, the term "treat" also denotes to arrest, delay the onset (i.e., the period prior to clinical manifestation of a disease) and/or reduce the risk of developing or worsening a disease.

As used herein the term "therapeutically effective" applied to dose or amount refers to that quantity of a compound or pharmaceutical composition that is sufficient to result in a desired activity upon administration to a subject in need thereof. Within the context of the present invention, when the term "therapeutically effective" is used in connection with the use of an inhibitor of a carbonic anhydrase, it refers to an amount of such inhibitor or a pharmaceutical composition comprising such inhibitor that is effective to relieve or alleviate at least one symptom associated with a neurological or psychiatric disorder, or to slow or reverse the progression of such disorder. Note that when a combination of active ingredients is administered (e.g., a combination of an inhibitor of a carbonic anhydrase and another compound effective for preventing, treating and/or inhibiting progression of a neurological or psychiatric disorder) the effective amount of the combination may or may not include amounts of each ingredient that would have been effective if administered individually.

The phrase "pharmaceutically acceptable", as used in connection with compositions of the invention, refers to molecular entities and other ingredients of such compositions that are physiologically tolerable and do not typically produce untoward reactions when administered to a subject (e.g., a mammal such as a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

As used in this specification and the appended claims, the singular forms "a," "an," and "the" include plural references unless the context clearly dictates otherwise.

The terms "patient", "individual", "subject", and "animal" are used interchangeably and refer to humans, veterinary animals (e.g., cats, dogs, cows, horses, sheep, pigs, etc.) and experimental animal models of neurological and psychiatric diseases, including animal models of neurodegenerative diseases.

The term "about" or "approximately" means within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition. Cold Spring Harbor, N.Y.: Cold Spring Harbor Laboratory Press, 1989 (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); Ausubel, F. M. et al. (eds.). Current Protocols in Molecular Biology. John Wiley & Sons, Inc., 1994. These techniques include site directed mutagenesis as described in Kunkel, Proc. Natl. Acad. Sci. USA 82: 488-492 (1985), U.S. Pat. No. 5,071,743, Fukuoka et al., Biochem. Biophys. Res. Commun. 263: 357-360 (1999); Kim and Maas, BioTech. 28: 196-198 (2000); Parikh and Guengerich, BioTech. 24: 4 28-431 (1998); Ray and Nickoloff, BioTech. 13: 342-346 (1992); Wang et al., BioTech. 19: 556-559 (1995); Wang and Malcolm, BioTech. 26: 680-682 (1999); Xu and Gong, BioTech. 26: 639-641 (1999), U.S. Pat. Nos. 5,789,166 and 5,932,419, Hogrefe, Strategies 14. 3: 74-75 (2001), U.S. Pat. Nos. 5,702,931, 5,780,270, and 6,242,222, Angag and Schutz, Biotech. 30: 486-488 (2001), Wang and Wilkinson, Biotech. 29: 976-978 (2000), Kang et al., Biotech. 20: 44-46 (1996), Ogel and McPherson, Protein Engineer. 5: 467-468 (1992), Kirsch and Joly, Nucl. Acids. Res. 26: 1848-1850 (1998), Rhem and Hancock, J. Bacteriol. 178: 3346-3349 (1996), Boles and Miogsa, Curr. Genet. 28: 197-198 (1995), Barrenttino et al., Nuc. Acids. Res. 22: 541-542 (1993), Tessier and Thomas, Meths. Molec. Biol. 57: 229-237, and Pons et al., Meth. Molec. Biol. 67: 209-218.

Methods and Compositions of the Invention

As described in the Examples section below, the present invention is based on the inventors' observations of the protective effect exerted by methazolamide (MTZ), a drug of the Carbonic Anhydrase Inhibitor (CAI) family, against mitochondrial damage induced by the Aβ in vitro and in vivo. As further demonstrated in the Examples, not only MTZ, but also other analogs of CAIs such as acetazolamide (AZT), are able to exert a positive effect on preventing or reverting the Aβ-induced mitochondrial dysfunctions and cell death, in both neuronal and endothelial cells. In fact, AZT appears to be more efficient requiring much lower concentrations for its effect.

Carbonic anhydrase CAIs function through the mitochondrial membrane depolarization and $H_2O_2$ generation. Interestingly, the intracellular presence of the rest of the Reactive Oxygen Species (ROS) and the mitochondrial calcium homeostasis were not affected in this model. In addition, no changes on intracellular pH or ATP were observed. This work shows a previously unrecognized pathway implicated in the Aβ-induced toxicity and opens the door to the use of old drugs, as CAIs, with a well-known profile of safety and efficacy, in the therapy of various neurological and psychiatric disorders, including neurodegenerative diseases such as AD.

Here, the inventors studied the effects of MTZ on caspase activation and apoptosis induced by Aβ challenge in neuronal and glial cells through the modulation of CytC release and mitochondrial $H_2O_2$ production. Moreover, the inventors analyzed the influence of MTZ on caspase 3 activation and neurodegeneration induced by Aβ after intra-hippocampal injection in the mouse brain. These results provide in vitro and in vivo evidence highlighting the potential of pharmacological strategies employing MTZ as promising new therapeutic avenues to explore in AD.

The inventors' work further shows that the carbonic anhydrase inhibitor (CAI) acetazolamide (ATZ) is able to inhibit the release of CytC from the mitochondria, as well as the production of mitochondrial reactive oxygen species (ROS), in particular hydrogen peroxide ($H_2O_2$). The inhibition of mitochondrial dysfunction results in the inventors' models in the prevention of caspase-3 activation and endothelial, neuronal and glial cell death. Herein is also provided mechanistic insights into the molecular pathways driving mitochondrial dysfunction induced by Aβ in both neuronal and endothelial cells (ECs), analyzing mitochondrial and cytoplasmic Calcium influx, membrane potential, ATP, ROS (Reactive Oxygen Species) and $H_2O_2$ (hydrogen peroxide) production, caspase activation and cell death. Furthermore, a novel therapeutic approach is proposed for preventing these events, analyzing the role of two carbonic anhydrase inhibitors (CAIs), methazolamide (MTZ) and, for the first time, acetazolamide (ATZ), on Aβ-mediated mitochondrial dysfunction and apoptotic cell death, in both neuronal (SH-SY5Y dopaminergic) cells and microvascular ECs, challenged respectively with Aβ42 and the vasculotropic Aβ40-Q22 mutant [18].

The ATZ compound belongs to a family of sulfonamides with CAI properties, FDA approved and capable of crossing the blood brain barrier, clinically used in the treatment of glaucoma—via both oral and local administration—as well as in the prevention of acute mountain sickness and related high-altitude cerebral edema, and in other indications, confirming the efficiency of the drug in the brain and the safety of its systemic administration [14]. Carbonic anhydrases (CA) are a family of enzymes catalyzing the conversion of $CO_2$ and $H_2O$ to bicarbonate and protons. CAs have a role in a number of physiological processes such as diuresis, production of body fluids, gluconeogenesis and lipogenesis. CAIs, among the other things, increase CBF (15), and decrease extracellular pH in the brain inducing vasodilation (41). An increase of CBF will likely induce additional protective effects in the AD brain, accelerating the clearance of Aβ from brain to blood (42, 43), which could act synergistically with the prevention of mitochondrial dysfunction. 16 mammalian CA isozymes have been discovered, among which CA VA and CA VB are mitochondrial. MTZ, acetazolamide (ATZ) and ethoxzolamide (ETZ), have a high activity on mitochondrial CA, although none of the presently available inhibitors has a specific isozyme selectivity (16). Through the inhibition of mitochondrial CA, ETZ was also able to inhibit ROS formation and cell death induced by high glucose in diabetes models (44, 45).

In the data provided herein, the effect of analog FDA-approved members of the CAI family, such as AZT, is demonstrated on mitochondrial damage and neurodegeneration. MTZ and AZT were approved decades ago by the FDA and other drug agencies, for human use in the treatment of glaucoma. AZT is also used for the prevention of acute mountain sickness and related cerebral edema, and as a diuretic drug. Due to the long-term use of MTZ and ATZ in chronic conditions, the efficacy and safety of their systemic administration has been widely proved [27].

In the Examples section, below, new mechanistic insights into the deleterious mitochondrial actions of amyloid are provided, and it is demonstrated that analog CAIs have similar protective effect on specific mitochondrial parameters in neuronal and microvascular ECs challenged with Aβ.

As demonstrated herein, ATZ is able to rescue human vascular (endothelial), neuronal and glial cells from Aβ-mediated apoptosis, preventing caspase activation and mitochondrial CytC release, and likely exerting its protective effect through inhibition of mitochondrial $H_2O_2$ production and reduced loss of mitochondrial membrane potential ($\Delta\Psi$).

ATZ, inhibiting mitochondrial ROS production, loss of $\Delta\Psi$, and the subsequent mitochondrial dysfunction, prevents the release of apoptotic factors that induce caspase activation and cell death, and could represent a highly effective strategy to attenuate neuronal synaptic loss and vascular cell death and mitochondrial dysfunction in AD. This compound has never been studied before for the inhibition of mitochondrial dysfunction and cell death in models of amyloidosis and Alzheimer's disease. The compound was effective in in vitro studies at concentrations 10 times lower than an analog compound the inventors have previously tested (Methazolamide). Animal studies in a model of cerebral vascular and parenchymal amyloidosis (TgSwDI mice) suggest that ATZ exerts positive effects on memory performance in mice treated for 3 months, starting the treatment at an age in which the pathology is at intermediate levels (5 months).

This new possible therapeutic use of ATZ in treatment of AD, based on the prevention of mitochondrial dysfunction and the consequent cell stress/death represents an important aspect of the present invention. The drug could be used as an early therapeutic/preventive agent to be given to MCI patients or patients at high risk of developing AD, such as, e.g., patients with Down Syndrome or Familial AD mutations (since mitochondrial dysfunction is an early event in all these types of pathology). The fact that ATZ is FDA approved makes the translation to clinical use faster and dramatically increases the possibility of human use and the safety of its administration, making clinical trials faster. ATZ could also be effective at reducing neurotoxic signals from active glial cells to neurons, also increased by ROS production and caspase activation. Glial overactivation, which results in glial cell death, release of cytokines and neuronal loss, is also known to trigger neuronal dysfunction. ATZ and analogs may also be able to decrease vascular endothelial cell dysfunction and the related blood brain barrier permeability, a known issue in AD and also a cause of white matter disease.

Various methods of the invention are specified in the Summary of the Invention section, above. All of these methods involve administration of an inhibitor of a carbonic anhydrase.

In one embodiment of any of the methods of the invention involving administering an inhibitor of a carbonic anhydrase to a subject, such inhibitor is administered chronically, e.g., over a period of more than 6 months or over a period of more than 1 year.

In the methods of the invention involving administering an inhibitor of a carbonic anhydrase to a subject, such inhibitor can be administered by any route of administration, including both systemic and local routes such as, e.g., oral, intravenous, intramuscular, mucosal, intranasal, by inhalation, sublingual, parenteral, intraperitoneal, intradermal, transdermal, etc. In one specific embodiment, CAI is administered to the subject orally.

In one embodiment of any of the methods of the invention, the carbonic anhydrase is CA VA or CA VB. In one embodiment of any of the above methods of the invention, the inhibitor of a carbonic anhydrase inhibits CA VA and/or CA VB. Non-limiting examples of inhibitors of carbonic anhydrases useful in the methods of the invention include acetazolamide (ATZ), methazolamide (MTZ), and ethoxzolamide (ETZ), sulthiame, dichlorophenamide, dorzolamide, brinzolamide, indisulam, topiramate, zonisamide, sulpiride, COuMATE, EMATE, celecoxib, valdecoxib, saccharin, chlorothiazide, hydrochlorothiazide, hydroflumethiazide, bendroflumethiazide, trichloromethiazide, polythiazide, quinethazone, metolazone, chlorthalidone, indapamide, furosemide, bumetanide, and various analogs and derivatives thereof. In one embodiment of any of the methods of the invention, the inhibitor of a carbonic anhydrase is not methazolamide (MTZ). In one embodiment of any of the methods of the invention, the inhibitor of a carbonic anhydrase is acetazolamide (ATZ) or a derivative or an analog thereof. In one embodiment of any of the methods of the invention, the inhibitor of a carbonic anhydrase is methazolamide (MTZ) or a derivative or an analog thereof.

The useful dosages of the compounds and pharmaceutical compositions of the invention will vary widely, depending upon the nature of the disease, the patient's medical history, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc., to maintain an effective dosage level. It is contemplated that a variety of doses will be effective to achieve a therapeutic effect. While it is possible to use a compound of the present invention for therapy as is, it may be preferable to administer it in a pharmaceutical formulation, e.g., in admixture with a suitable pharmaceutical excipient, diluent or carrier selected with regard to the intended route of administration and standard pharmaceutical practice. The excipient, diluent and/or carrier must be "acceptable" in the sense of being compatible with the other ingredients of the formulation and not deleterious to the recipient thereof. Acceptable excipients, diluents, and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient, diluent, and carrier can be selected with regard to the intended route of administration and standard pharmaceutical practice.

In one specific embodiment of any of the methods of the invention involving administering to a subject, acetazolamide (ATZ) or a derivative or an analog thereof is administered to the subject in a dose of 0.1-20 mg/kg/day. In another embodiment, acetazolamide (ATZ) or a derivative or an analog thereof is administered to the subject in a dose of 0.1-1 mg/kg/day.

In one specific embodiment of any of the methods of the invention involving administering to a subject, methazolamide (MTZ) or a derivative or an analog thereof is administered to the subject in a dose of 0.1-20 mg/kg/day. In another embodiment, methazolamide (MTZ) or a derivative or an analog thereof is administered to the subject in a dose of 0.1-1 mg/kg/day.

Non-limiting examples of neurological or psychiatric disorders treatable by the methods of the invention include Alzheimer's disease (AD), Mild Cognitive Impairment (MCI), Parkinson's disease (PD), Huntington's disease (HD), prion-caused diseases, frontotemporal dementia (FTD), Lewy body dementia, vascular dementias, white matter disease, traumatic brain injury, post-traumatic stress, stroke, tauopaties, Down Syndrome, Amyotrophic Later Sclerosis (ALS), chronic traumatic encephalopathy (CTE), progressive supranuclear palsy (PSP), multiple system atrophy (MSA), corticobasal degeneration (CBGD), Pick's disease, olivopontocerebellar atrophy (OPCA), senile dementia of the Alzheimer type, progressive supranuclear palsy (Steel-Richardson-Olszewski), corticodentatonigral degeneration, Hallervorden-Spatz disease, striatonigral degeneration, torsion dystonia (e.g., torsion spasm; dystonia musculorum deformans), spasmodic torticollis and other dyskinesis, familial tremor, Gilles de la Tourette syndrome, cerebellar cortical degeneration, spinocerebellar degeneration (e.g., Friedreich's ataxia and related disorders), Shy-Drager syndrome, spinal muscular atrophy, primary lateral sclerosis, hereditary spastic paraplegia, peroneal muscular atrophy (Charcot-Marie-Tooth), hypertrophic interstitial polyneuropathy (Dejerine-Sottas), chronic progressive neuropathy, pigmentary degeneration of the retina (retinitis pigmentosa), hereditary optic atrophy (Leber's disease), Cognitive Dysfunction Syndrome, White dog shaker syndrome, degenerative myelopathy, neuroaxonal dystrophy, cerebellar degeneration, and cerebellar abiotrophy.

The CAIs useful in the methods of the invention can be administered in combination with other known treatments. Such combination treatments may involve the use of pharmaceutical compositions comprising several active ingredients.

In conjunction with the methods of the invention, provided herein are various pharmaceutical compositions comprising CAIs of the invention.

The compositions of the invention can comprise a carrier and/or excipient. While it is possible to use a compound of the present invention for therapy as is, it may be preferable to administer it in a pharmaceutical formulation, e.g., in admixture with a suitable pharmaceutical excipient and/or carrier selected with regard to the intended route of administration and standard pharmaceutical practice. The excipient and/or carrier must be "acceptable" in the sense of being compatible with the other ingredients of the formulation and not deleterious to the recipient thereof. Acceptable excipients and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient and carrier can be selected with regard to the intended route of administration and standard pharmaceutical practice. Oral formulations readily accommodate additional mixtures, such as, e.g., milk, yogurt, and infant formula. Solid dosage forms for oral administration can also be used and can include, e.g., capsules, tablets, caplets, pills, troches, lozenges, powders, and granules. Non-limiting examples of suitable excipients include, e.g., diluents, buffering agents, preservatives, stabilizers, binders, compaction agents, lubricants, dispersion enhancers, disintegration agents, antioxidants, flavoring agents, sweeteners, and coloring agents. Those of relevant skill in the art are well able to prepare suitable solutions.

The compositions of the invention can be formulated for delivery by any useful route of administration.

Oral delivery may also include the use of nanoparticles that can be targeted, e.g., to the GI tract of the subject, such as those described in Yun et al., Adv Drug Deliv Rev. 2013, 65(6):822-832 (e.g., mucoadhesive nanoparticles, negatively charged carboxylate- or sulfate-modified particles, etc.). Non-limiting examples of other methods of targeting delivery of compositions to the GI tract are discussed in U.S. Pat. Appl. Pub. No. 2013/0149339 and references cited therein (e.g., pH sensitive compositions [such as, e.g., enteric polymers which release their contents when the pH becomes alkaline after the enteric polymers pass through the stomach], compositions for delaying the release [e.g., compositions which use hydrogel as a shell or a material which coats the active substance with, e.g., in vivo degradable polymers, gradually hydrolyzable polymers, gradually water-soluble polymers, and/or enzyme degradable polymers], bioadhesive compositions which specifically adhere to the colonic mucosal membrane, compositions into which a protease inhibitor is incorporated, a carrier system being specifically decomposed by an enzyme present in the colon).

For oral administration, the active ingredient(s) can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and nonaqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Solutions or suspensions can include any of the following components, in any combination: a sterile diluent, including by way of example without limitation, water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity, such as sodium chloride or dextrose.

In instances in which the agents exhibit insufficient solubility, methods for solubilizing agents may be used. Such methods are known to those of skill in this art, and include, but are not limited to, using co-solvents, such as, e.g., dimethylsulfoxide (DMSO), using surfactants, such as TWEEN® 80, or dissolution in aqueous sodium bicarbonate. Pharmaceutically acceptable derivatives of the agents may also be used in formulating effective pharmaceutical compositions.

The composition can contain along with the active agent, for example and without limitation: a diluent such as lactose, sucrose, dicalcium phosphate, or carboxymethylcellulose; a lubricant, such as magnesium stearate, calcium stearate and talc; and a binder such as starch, natural gums, such as gum acacia gelatin, glucose, molasses, polyvinylpyrrolidone, celluloses and derivatives thereof, povidone, crospovidones and other such binders known to those of skill in the art. Liquid pharmaceutically administrable compositions can, for example, be prepared by dissolving, dispersing, or otherwise mixing an active agent as defined above and optional pharmaceutical adjuvants in a carrier, such as, by way of example and without limitation, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, such as, by way of example and without limitation, acetate, sodium citrate, cyclodextrin derivatives, sorbitan monolaurate, triethanolamine sodium acetate, triethanolamine oleate, and other such agents. Actual methods of preparing such dosage forms are known, or will be apparent, to those skilled in this art (e.g., Remington's Pharmaceutical Sciences, Mack Publishing Company, Easton, Pa., 15th Edition, 1975). The composition or formulation to be administered will, in any event, contain a quantity of the active agent in an amount sufficient to alleviate the symptoms of the treated subject.

The active agents or pharmaceutically acceptable derivatives may be prepared with carriers that protect the agent against rapid elimination from the body, such as time release formulations or coatings. The compositions may include other active agents to obtain desired combinations of properties.

Oral pharmaceutical dosage forms include, by way of example and without limitation, solid, gel and liquid. Solid dosage forms include tablets, capsules, granules, and bulk powders. Oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or agents of a similar nature: a binder; a diluent; a disintegrating agent; a lubricant; a glidant; a sweetening agent; and a flavoring agent.

Examples of binders include, by way of example and without limitation, microcrystalline cellulose, gum tragacanth, glucose solution, acacia mucilage, gelatin solution, sucrose, and starch paste. Lubricants include, by way of example and without limitation, talc, starch, magnesium or calcium stearate, lycopodium and stearic acid. Diluents include, by way of example and without limitation, lactose, sucrose, starch, kaolin, salt, mannitol, and dicalcium phosphate. Glidants include, by way of example and without limitation, colloidal silicon dioxide. Disintegrating agents include, by way of example and without limitation, croscarmellose sodium, sodium starch glycolate, alginic acid, corn starch, potato starch, bentonite, methylcellulose, agar and carboxymethylcellulose. Coloring agents include, by way of example and without limitation, any of the approved certified water soluble FD and C dyes, mixtures thereof; and water insoluble FD and C dyes suspended on alumina hydrate. Sweetening agents include, by way of example and without limitation, sucrose, lactose, mannitol and artificial sweetening agents such as saccharin, and any number of spray dried flavors. Flavoring agents include, by way of example and without limitation, natural flavors extracted from plants such as fruits and synthetic blends of agents which produce a pleasant sensation, such as, but not limited to peppermint and methyl salicylate. Wetting agents include, by way of example and without limitation, propylene glycol monostearate, sorbitan monooleate, diethylene glycol monolaurate, and polyoxyethylene laural ether. Emetic-coatings include, by way of example and without limitation, fatty acids, fats, waxes, shellac, ammoniated shellac and cellulose acetate phthalates. Film coatings include, by way of example and without limitation, hydroxyethylcellulose, sodium carboxymethylcellulose, polyethylene glycol 4000 and cellulose acetate phthalate.

If oral administration is desired, the agent could be provided in a composition that protects it from the acidic environment of the stomach. For example, the composition can be formulated in an enteric coating that maintains its integrity in the stomach and releases the active agent in the intestine. The composition may also be formulated in combination with an antacid or other such ingredient.

When the dosage unit form is a capsule, it can contain, in addition to material of the above type, a liquid carrier such as fatty oil. In addition, dosage unit forms can contain various other materials which modify the physical form of the dosage unit, for example, coatings of sugar and other enteric agents. The agents can also be administered as a component of an elixir, suspension, syrup, wafer, sprinkle, chewing gum or the like. A syrup may contain, in addition to the active agents, sucrose as a sweetening agent and certain preservatives, dyes and colorings and flavors. The active materials can also be mixed with other active materials which do not impair the desired action, or with materials that supplement the desired action, such as antacids, $H_2$ blockers, and diuretics.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents may be used in any of the above dosage forms.

Solvents include, by way of example and without limitation, glycerin, sorbitol, ethyl alcohol and syrup. Examples of preservatives include, without limitation, glycerin, methyl and propylparaben, benzoic acid, sodium benzoate and alcohol. Non-aqueous liquids utilized in emulsions include, by way of example and without limitation, mineral oil and cottonseed oil. Emulsifying agents include, by way of example and without limitation, gelatin, acacia, tragacanth, bentonite, and surfactants such as polyoxyethylene sorbitan monooleate. Suspending agents include, by way of example and without limitation, sodium carboxymethylcellulose, pectin, tragacanth, Veegum and acacia. Diluents include, by way of example and without limitation, lactose and sucrose. Sweetening agents include, by way of example and without limitation, sucrose, syrups, glycerin and artificial sweetening agents such as saccharin. Wetting agents include, by way of example and without limitation, propylene glycol monostearate, sorbitan monooleate, diethylene glycol monolaurate, and polyoxyethylene lauryl ether. Organic acids include, by way of example and without limitation, citric and tartaric acid. Sources of carbon dioxide include, by way of example and without limitation, sodium bicarbonate and sodium carbonate. Coloring agents include, by way of example and without limitation, any of the approved certified water soluble FD and C dyes, and mixtures thereof. Flavoring agents include, by way of example and without limitation, natural flavors extracted from plants, such as fruits, and synthetic blends of agents which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245, 4,409,239, and 4,410,545. For a liquid dosage form, the solution (e.g., in a polyethylene glycol) may be diluted with a sufficient quantity of a pharmaceutically acceptable liquid carrier (e.g., water) to be easily measured for administration.

Alternatively, liquid or semi-solid oral formulations may be prepared by dissolving or dispersing the active agent or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. RE28819 and U.S. Pat. No. 4,358,603. Briefly, such formulations include, but are not limited to, those containing an agent provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes, such as acetaldehyde diethyl acetal.

Tablets and capsules formulations may be coated as known by those of skill in the art in order to modify or sustain dissolution of the active ingredient. Thus, for example and without limitation, they may be coated with a conventional enterically digestible coating, such as phenylsalicylate, waxes and cellulose acetate phthalate.

Parenteral administration, generally characterized by injection, either subcutaneously, intramuscularly or intravenously, is also contemplated herein. Injectables can be prepared in conventional forms, either as liquid solutions or suspensions, solid forms suitable for solution or suspension in liquid prior to injection, or as emulsions. Suitable excipients include, by way of example and without limitation, water, saline, dextrose, glycerol or ethanol. In addition, if desired, the pharmaceutical compositions to be administered may also contain minor amounts of non-toxic auxiliary substances, such as wetting or emulsifying agents, pH buffering agents, stabilizers, solubility enhancers, and other such agents, such as, for example, sodium acetate, sorbitan monolaurate, triethanolamine oleate and cyclodextrins.

Implantation of a slow-release or sustained-release system, such that a constant level of dosage is maintained (e.g., U.S. Pat. No. 3,710,795) is also contemplated herein. Briefly, an inhibitor of Nt5e or A1R is dispersed in a solid inner matrix (e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate) that is surrounded by an outer polymeric membrane (e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer) that is insoluble in body fluids. The agent diffuses through the outer polymeric membrane in a release rate controlling step. The percentage of active agent contained in such parenteral compositions is highly dependent on the specific nature thereof, as well as the activity of the agent and the needs of the subject.

Lyophilized powders can be reconstituted for administration as solutions, emulsions, and other mixtures or formulated as solids or gels. The sterile, lyophilized powder is prepared by dissolving an agent provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain, by way of example and without limitation, a single dosage (10-1000 mg, such as 100-500 mg) or multiple dosages of the agent. The lyophilized powder can be stored under appropriate conditions, such as at about 4° C. to room temperature. Reconstitution of this lyophilized powder with water for injection provides a formulation for use in parenteral administration. For reconstitution, about 1-50 mg, such as about 5-35 mg, for example, about 9-30 mg of lyophilized powder, is added per mL of sterile water or other suitable carrier. The precise amount depends upon the selected agent. Such amount can be empirically determined.

The inventive composition or pharmaceutically acceptable derivatives thereof may be formulated as aerosols for application e.g., by inhalation or intranasally (e.g., as described in U.S. Pat. Nos. 4,044,126, 4,414,209, and 4,364,923). These formulations can be in the form of an aerosol or solution for a nebulizer, or as a microfine powder for insufflation, alone or in combination with an inert carrier such as lactose. In such a case, the particles of the formulation will, by way of example and without limitation, have diameters of less than about 50 microns, such as less than about 10 microns.

Other routes of administration, such as transdermal patches are also contemplated herein. Transdermal patches, including iontophoretic and electrophoretic devices, are well known to those of skill in the art. For example, such patches are disclosed in U.S. Pat. Nos. 6,267,983, 6,261,595, 6,256,533, 6,167,301, 6,024,975, 6,010,715, 5,985,317, 5,983,134, 5,948,433, and 5,860,957.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1. MTZ Prevents Amyloid Beta-Induced Mitochondrial Dysfunction and Caspase Activation Protecting Neuronal and Glial Cells In Vitro and in the Mouse Brain In this Example, the effects of MTZ on caspase activation and apoptosis induced by Aβ challenge were studied in neuronal and glial cells through the modulation of CytC release and mitochondrial $H_2O_2$ production. Moreover, the inventors analyzed the influence of MTZ on caspase 3 activation and neurodegeneration induced by Aβ after intrahippocampal injection in the mouse brain. The results disclosed herein provide in vitro and in vivo evidence highlighting the potential of pharmacological strategies employing MTZ as promising new therapeutic avenues to explore in AD. The data also shows that the carbonic anhydrase inhibitor (CAI) acetazolamide (ATZ) is able to inhibit the release of CytC from the mitochondria, as well as the production of mitochondrial reactive oxygen species (ROS), in particular hydrogen peroxide ($H_2O_2$). The inhibition of mitochondrial dysfunction results in the models in the prevention of caspase-3 activation and endothelial, neuronal and glial cell death.

This compound belongs to a family of sulfonamides with CAI properties, FDA approved and capable of crossing the blood brain barrier, clinically used in the treatment of glaucoma—via both oral and local administration—as well as in the prevention of acute mountain sickness and related high-altitude cerebral edema, and in other indications, confirming the efficiency of the drug in the brain and the safety of its systemic administration [14].

Materials and Methods

Aβ Peptides

Synthetic homologues of the amyloid subunits Aβ42 and Aβ40-Q22 (the Dutch genetic variant, containing the E22Q substitution) were synthesized using N-tert-butyloxycarbonyl chemistry by James I. Elliott at Yale University. Aβ homologues were dissolved to 1 mM in 1,1,1,3,3,3-hexafluoro-2-propanol (HFIP; Sigma), incubated overnight to break down pre-existing β-sheet structures (Fossati et al., 2010), and lyophilized. Peptides were subsequently dissolved in DMSO to a 10 mM concentration, followed by the addition of deionized water to 1 mM concentration and by further dilution into culture media to the required concentrations for the different experiments.

Cell Cultures

Human neuroblastoma cells (SH-SY5Y) were obtained from the American Type Culture Collection (ATCC, Manassas, Va., USA) and maintained in DMEM/F12 medium (50:50, Mediatech, Manassas, Va.) with 10% FBS. M059K Glioma cells were obtained from ATCC and maintained in DMEM with 10% FBS. Normal Human Astrocytes were purchased from Lonza (Walkersville, Md.) and were cultured in Astrocyte Growth Medium (Lonza) containing the pertinent growth factors and FBS provided by the manufacturer.

Cell Death ELISA

The extent of apoptosis caused by Aβ in the presence or absence of MTZ was assessed by quantitation of nucleosome formation using Cell Death ELISA$^{plus}$ (Roche Applied Science, Indianapolis, Ind.). Briefly, after incubation with the peptides, plates were centrifuged in a Beckman J-6B centrifuge (10 min; 1,000 rpm), cells lysed, and DNA-histone complexes (nucleosomes) quantitated by Cell Death ELISA, as previously described (Fossati et al., 2010).

Thioflavin T Binding Assay

Binding of the different Aβ peptides to Thioflavin-T was monitored by fluorescence evaluation, as described (Fossati et al., 2010; Walsh et al., 1999). Briefly, after peptide aggregation at 50 µM concentration in culture media in the presence or absence of MTZ, 6 µl aliquots from each of the time-points were added to 184 µl of 50 mM Tris-HCl buffer, pH 8.5, and 10 µl of 0.1 mM Thioflavin-T (Sigma). Fluorescence was recorded for 300 s in a LS-50B luminescence spectrometer (Perkin Elmer, Waltham, Mass.) with excitation and emission wavelengths of 435 and 490 nm (slit width 10 nm), respectively, as described (Solito et al., 2009; Viana et al., 2009).

Native Gel Electrophoresis and Western Blot Analysis

Electrophoretic analysis for assessment of peptide aggregation in the presence or absence of MTZ was performed under native conditions using 5-30% gradient polyacrylamide gels, in absence of SDS, using 25 mM Tris/glycine, pH 8.8, as running buffer, as previously described (Fossati et al., 2010). Aβ oligomerization patterns were visualized by subsequent WB analysis. Briefly, proteins were electrotransferred to nitrocellulose membranes (0.45 µM pore size; Hybond-ECL, GE Healthcare Life Sciences, Piscataway, N.J.) at 400 mA for 2.5 h, using 10 mM 3-cyclohexylamino-1-propanesulfonic acid (CAPS; Sigma) buffer, pH 11.0, containing 10% (v/v) methanol. After blocking with 5% nonfat milk in TBS containing 0.1% Tween 20 (TBST), membranes were immunoreacted with a combination of mouse monoclonal anti-Aβ antibodies 4G8 (epitope: residues Aβ18-22) and 6E10 (epitope: residues Aβ3-8), both from Covance (Princeton, N.J.), at 1:3000 dilution each, followed by HRP-labeled anti-mouse IgG and ECL chemistry (Fossati et al., 2010).

Immunocytochemical Evaluation of Cytochrome C Release

Both SH-SY5Y cells and Glioma cells were plated on glass chamber slides (Thermo Fisher Scientific, Rochester, N.Y.). Slides were pre-coated with poly-D-lysine for SH-SY5Y cells. After seeding, cells were allowed to attach for 1 day prior to treatment with Aβ in the presence or absence of MTZ for 24 hours. Cells were then washed with PBS, fixed with 4% paraformaldehyde (10 min, RT) and blocked for 1 hour with 20 mg/ml BSA in PBS containing 0.3% Triton X-100 (PBST). Slides were further incubated with mouse monoclonal anti-CytC antibody (BD Biosciences; 1:200 in PBST containing 5 mg/ml BSA; 2 h, RT) followed by Alexa Fluor 488-conjugated anti-mouse IgG (Life Technologies, Grand Island, N.Y.) 1:200 in PBST with 5 mg/ml BSA for 1 h at RT, as previously described (Fossati et al., 2013). Fluorescence signals were visualized in a Zeiss LSM 510 laser scanning confocal/Confocor2 microscope using a 40×DIC oil immersion objective and LSM 510 software; acquired images were imported into ImageJ (National Institute of Health; http://rsbweb.nih.gov/ij/).

ELISA and Western Blot Assessment of CytC in Mitochondrial and Cytoplasmic Subcellular Fractions Subcellular distribution of CytC in amyloid-challenged SH-SY5Y and glioma cells was determined in mitochondrial and cytoplasmic protein extracts prepared using Mitochondria Isolation Kit (MITOISO2, Sigma) following the manufacturer's specifications. Briefly, after amyloid challenge in the presence and absence of Methazolamide, as above, cells were collected by trypsinization, resuspended in 10 mM HEPES, pH 7.5, containing 200 mM mannitol, 70 mM sucrose, 1 mM EGTA added of Protease Inhibitor Cocktail, and homogenized with the aid of a Dounce glass homogenizer. Cell homogenates were centrifuged to remove unbroken cells and nuclei (600×g, 5 min, 4° C.) and supernatants further centrifuged at 11,000×g (5 min, 4° C.) to subfractionate mitochondria. Supernatants, representing the cytosolic fractions as well as mitochondrial fractions were analyzed by CytC ELISA and WB.

Solid Phase ELISA.

The concentration of CytC in cytosolic and mitochondrial fractions was quantitated by solid phase sandwich ELISA (Quantikine ELISA, human Cytochrome C Immunoassay, R&D Systems) as described by the manufacturer. Prior to the assay, fractions containing cytoplasmic proteins were concentrated on Vivaspin 500 centrifugal concentrators (GE HealthCare, molecular weight cut off 5000), mitochondrial pellets were resuspended in Cell Lysis Buffer provided with the kit, and total protein of the respective fractions was evaluated by BCA protein assay (Thermo Fisher Scientific/Pierce). Samples and human CytC standards were diluted in Calibrator Diluent and incubated with microtiter wells pre-coated with a monoclonal antibody specific for human CytC. After washing away unbound proteins, wells were further incubated with an HRP-linked monoclonal antibody anti-human CytC, color developed with tetramethylbenzinine peroxidase substrate, and evaluated through quantitation of the Absorbance at 450 nm. The CytC concentration of the different samples was interpolated from the standard curve with the aid of GraphPad Prism and normalized to the protein content of the respective subcellular fractions.

Western Blot Analysis.

Cytosolic and mitochondrial fractions were separated on 14% SDS-polyacrylamide gels under reducing conditions and electrotransferred to PVDF membranes (Immobilon, Millipore, Billerica, Mass.; 0.45 µm pore; 400 mA, 1.5 h) using CAPS buffer, as above. Membranes were blocked with 5% nonfat milk in TBST, and subsequently immunoreacted with mouse monoclonal anti-CytC antibody (BD; 1 µg/ml in 5% nonfat milk in TBST, overnight, 4° C.) followed by HRP-labeled anti-mouse IgG (1:10,000; GE Healthcare), and ECL detection, as above. As loading controls, membranes were probed with rabbit polyclonal anti-β actin (Novus Biologicals; 1 µg/ml, overnight, 4° C.) followed by HRP-labeled anti-rabbit IgG (1: 5,000; GE Healthcare). Densitometric assessment of band intensities was performed using ImageJ software (rsbweb.nih.gov)

Caspase 9 and Caspase 3/7 Activity Assay

Caspase 9 and caspase 3/7 activation was measured by luminescent assays (Caspase-Glo 9 and caspase-Glo 3/7, Promega, Madison, Wis.), in cells treated with the Aβ peptides in DMEM without FBS. Briefly, 10,000 cells/well were plated in 96 wells plates and incubated for 24 hours with the freshly solubilized Aβ peptides. Caspase-Glo reagent was added to the cell cultures resulting in cell lysis, followed by caspase cleavage of the substrate and generation of a luminescent signal produced by the luciferase reaction. After 40 minutes incubation, the amount of caspase activity was evaluated in a plate-reading luminometer (Synergy HT Multi-Mode Microplate Reader, Biotek, Winooski, Vt.) as described in (Fossati et al., 2012b). To inhibit non-specific background activity, the proteasome inhibitor MG-132 was added to the Caspase-Glo reagent before the experiment as indicated by the manufacturer. In all cases results are expressed as fold-change compared to untreated control cells.

Immunocytochemical Evaluation of Active Caspase 3

SHSY-5Y and Glioma cells were plated on chamber slides as above. Slides were pre-coated with Poly-D-Lysine 30 μg/ml for 2 hours for SHSY-5Y cells. Cells were treated with Aβ peptides in the presence or absence of MTZ (100 or 300 μM), and stained, as above, with a rabbit monoclonal antibody against the activated form of Caspase 3 (Cell Signaling Technology, Danvers, Mass.), followed by Alexa Fluor 488-conjugated anti-rabbit IgG (Life Technologies; 1:200 in PBST with 5 mg/ml BSA; 1 h, RT). Nuclei were counterstained in blue with DAPI. Images were acquired using a Nikon Eclipse Ti inverted microscope with a 20× objective, and NIS Elements software.

Mitochondrial $H_2O_2$ Production

Production of $H_2O_2$ from isolated mitochondria was measured using Amplex Red Hydrogen Peroxide/Peroxidase Assay (Life Technologies). Cells were treated with Aβ peptides, in the presence or absence of MTZ. After 16 hours of treatment, the mitochondrial fraction was separated from nuclear and cytoplasmic fractions as previously described (Fossati et al., 2013). Protein concentration in the mitochondrial fraction was measured by BCA assay (Thermo Scientific, Rockford, Ill.), in order to include the same amount of mitochondria in each sample. Functional mitochondrial fractions were distributed in a 96 well plate with Reaction Buffer and Amplex Red solution following the manufacturer's specifications. The plate was incubated in the dark at room temperature for 30 minutes before colorimetric evaluation of the Amplex Red reaction at 560 nm.

Cellular ROS Measurement

SH-SY5Y and glioma cells were seeded at a density of $10^4$ cells/well on 96-well plates and challenged with Aβ in the presence or absence of MTZ for 16 h. For the last 30 minutes, the cells were incubated in the experimental medium at 37° C. with 5 μM CellROX Deep Red (Life Technologies) and 1 μg/ml Hoechst Stain (Immunochemistry Technologies, Bloomington, Minn.), as described by the manufacturer, followed by washes. Fluorescence was measured using a FlexStation 3 Multi-Mode Microplate Reader (Molecular Devices, Sunnyvale, Calif.).

Hippocampal Injections with Aβ Peptide

Six months old C57BL/6 mice were anesthetized with a mixture of ketamine and xylazine (120 and 10 mg/Kg respectively) i.p. and fixed to a stereotaxic frame (David Kopf Instruments, Tujunga, CaliforniaKopf). The body temperature was maintained stable with the use of a heating pad (Harvard Apparatus, Holliston, Mass.) for the total time of the surgery. A volume of 1 μl of a 10 μM fresh solution of Aβ40-Q22—chosen for its propensity to form toxic oligomers, and not fibrils, in the first few hours after solubilization—(Fossati et al., 2010) in PBS, or the vehicle for control mice, was injected in the hippocampus (Coordinates: AP=−2.7, L=−3.0 and H=−4.0, according to the Atlas of Paxinos and Franklin) at a flow rate of 0.1 μl/min. The needle (Hamilton 701 RN 10 μl syringe, RN needle 30/2"/3S) was left in place for two minutes and then slowly withdrawn. In the cases in which MTZ treatment was administered, mice were injected intraperitoneally with a solution of MTZ (20 mg/kg) 1 h before the Aβ40-Q22 intrahippocampal injection. At the selected time after injections, the animals were sacrificed by trans-cardiac perfusion (medium flow pump, Fisher Scientific 13-876-2, 10 ml/min flow rate) with PBS for 2 minutes followed by 4% paraphormaldehyde for 5 minutes. Brains were then removed from the skull and postfixed in 4% paraphormaldehyde for 2 h at 4° C. Cryoprotection was achieved with a solution of sucrose 15% for a day, later changed to a solution of sucrose 30% for 2 days. Brains were then washed in PBS, assembled in a plastic mold with Tissue-Tek O.C.T. compound (Fisher Scientific), and frozen with a mixture of liquid nitrogen and isopentanol. Serial cryostat sections of 8 μm thickness were collected on positively charged microscope slides (Fisher Scientific) and stored at −80° C. until further immunohistochemical analysis.

Immunohistochemistry

For immunohistochemical staining, slices were warmed to RT for 5' prior to use, rinsed in PBS and blocked with Mouse on Mouse (MOM) blocking reagent (2 drops in 2.5 ml of PBS, Vector Laboratories, Burlingame, Calif.) for 20 minutes. Incubation with the rabbit monoclonal antibody against active caspase-3 (Cell Signaling Technology) was performed overnight at 4° C. in PBS containing 0.1% triton X-100 and 5 mg/ml BSA. The day after, the sections were washed three times with PBS and incubated in Alexa Fluor 488- or 633-conjugated anti-rabbit IgG (Life Technologies; 1:200 in PBST with 5 mg/ml BSA; 1 h at RT), followed by primary anti-Aβ 6E10 (1:200 in PBS+MOM for 2 hours at RT), and by secondary Alexa Fluor 568 anti-mouse IgG. Finally, the slices were washed and the DNA counterstained with TO-PRO (Life Technologies) 1:1000 for 10 min, or with NeuN green neuronal staining (1:100 in PBS for 1 hour, Millipore, Temecula, Calif.). For staining of active microglial cells, tissue sections were incubated with anti IBA1 goat antibody (Abcam, Cambridge, Mass.) 1:200 in PBS containing 0.1% Triton and 5 mg/ml BSA for 1 hour, followed by Alexa Fluor 488 anti-goat IgG (1 hour). After washing, slides were mounted with an aqueous mounting medium (Vector Laboratories). Images were acquired in a Zeiss LSM 510 confocal microscope using 40× or 100× oil lens and processed using Image J and Adobe Photoshop. Images were acquired maintaining constant exposure for all samples across single experiments. For quantifications, stained brain slices corresponding to the injection site area of 3 or more animals were quantified with Image J. The total area of NeuN, caspase 3, Aβ and IBA1 positive cells was quantified and compared between different treatments.

Statistical Analysis

ANOVA with Tukey post hoc tests for comparison of multiple groups and unpaired t test for comparison of 2 groups were performed using GraphPad Prism (GraphPad, La Jolla, Calif.). Values of $P \leq 0.05$ were considered significant.

Results

MTZ Prevents Neuronal and Glial Aβ-Mediated Apoptosis without Affecting Peptide Aggregation.

Treatment with different familial or sporadic variants of Aβ has been shown to induce apoptosis in multiple brain cell types, including neuronal and glial cells (Bashir et al., 2014; Fossati et al., 2013; Modi et al., 2014). Neuronal SHSY-5Y cells, M059K glioma cells and Normal Human Astrocytes were challenged with WT-Aβ42 (10 μM), and the Dutch mutant of A1340 (Aβ40-Q22, 50 μM). While A1340 is typically less toxic for neuronal cells compared to Aβ42, the Aβ40-Q22 variant is known have a high propensity to form toxic oligomers after very short aggregation times (Cruz et al., 2005; Fossati et al., 2010; Fossati et al., 2012a), and to affect synaptic structure in AD mouse models (Price et al., 2014). Both Aβ42 and Aβ40-Q22 caused an increase of 2 to 3 times in the level of apoptosis, measured as amount of fragmented DNA by Cell death ELISA$^{PLUS}$, for all the cell types analyzed (FIG. 1A). The CAI MTZ was able to significantly reduce the number of fragmented nucleosomes after challenge with Aβ42 and Aβ40-Q22 in both neuronal and glial cells. The effect of 300 μM MTZ was so substantial it completely prevented the Aβ-mediated increase in fragmented nucleosomes for all the cell types challenged with Aβ42, and for both neuronal and glioma cells treated with Aβ40-Q22. MTZ at 100 μM concentration was also significantly effective at reducing DNA fragmentation, and completely reverted the apoptotic phenotype caused by the Aβ peptides in glioma cells.

In order to rule out the possibility that the protective effect of MTZ could be due to a decrease in Aβ aggregation propensity in the presence of the drug, the formation of different aggregation species was tested in vitro in the presence or absence of MTZ. When the peptides were aggregated for up to 3 days at the same concentration and in the same media used for the cell experiments in the presence of 100 or 300 μM MTZ, no significant difference in fibrillization was found, as evaluated by Thioflavin T fluorescence (FIG. 1B). Furthermore, the aggregation species yielded by both Aβ42 and Aβ40-Q22 in the presence or absence of the CAI at the respective time points did not differ as evaluated by electrophoretic separation of the aggregated peptides in native gels and immunoreaction with anti-Aβ antibodies (FIG. 1C).

Cytochrome C Release, Caspase 9 and Caspase 3 Activation are Prevented by MTZ Through the Inhibition of Mitochondrial $H_2O_2$ Production.

Figure 4A:
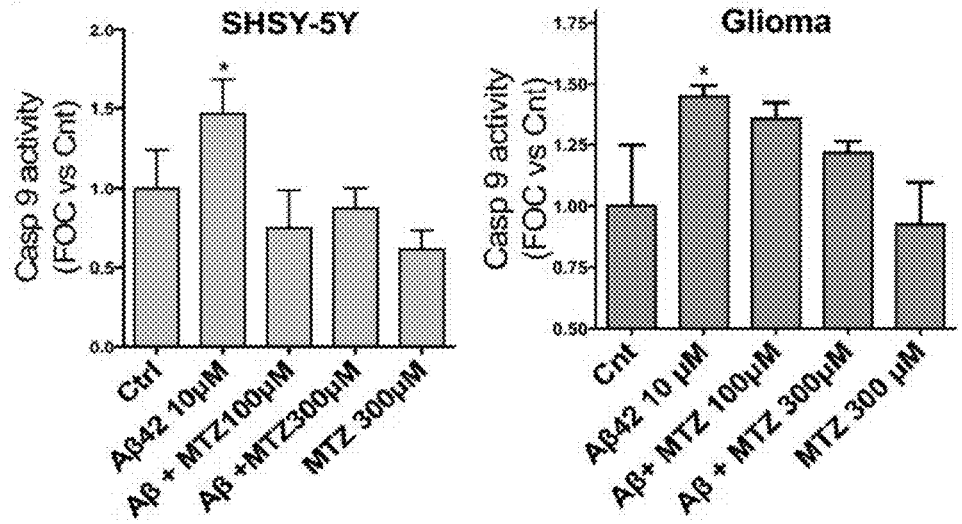

It is currently recognized that mitochondrial dysfunction is an early event in AD patients and in AD mice models, preceding and inducing the activation of caspases and the neurodegenerative process (Atamna and Frey, 2007; Balietti et al., 2013; Calkins et al., 2011; Du et al., 2010). The inventors have previously shown how Aβ genetic variants trigger common mitochondria-mediated cell death pathways within different time frames, correlating with the aggregation properties of each peptide (Fossati et al., 2010; Fossati et al., 2012b; Fossati et al., 2013). Since CytC release is a common pathological event linking mitochondrial dysfunction to apoptotic cell death, the inventors asked whether MTZ was able to inhibit Aβ-induced CytC release in neuronal and glial cells. CytC staining, visible as chain-like structures representing mitochondrial localization of the molecule in healthy cells, was diffused in the cytoplasm after cell incubation with Aβ42 10 μM for 24 hours. This indicates release of the molecule from the mitochondrial inter-membrane space, a typical point of no return in both the extrinsic and intrinsic apoptotic pathways. In the presence of 100 μM MTZ given together with Aβ, the release of CytC was prevented in both neuronal and glial cells (FIG. 2). The release of CytC in Aβ-treated SHSY-5Y and glioma cells and its inhibition by MTZ were also confirmed by CytC ELISA and Western blot performed in mitochondrial (FIGS. 3A-3B) and cytosolic (FIGS. 3C-3D) fractions as shown in FIG. 3A-3D. Since CytC release is known to be an essential event for the maturation and activation of caspase 9 through formation of the apoptosome (Jiang and Wang, 2000; Kim et al., 2005), the present inventors tested whether caspase 9 activation, typically induced by Aβ, as previously shown (Fossati et al., 2012a; Fossati et al., 2012b; Zussy et al., 2013), could be inhibited by MTZ. As expected, it was found that when both neuronal and glial cells were challenged with 10 μM Aβ42 for 24 hours, caspase 9 activation, measured by luminescence, was significantly increased (about 1.5 times) compared to control cells (FIG. 4A). Caspase 9 over-activation was completely inhibited in the presence of 100 or 300 μM MTZ in neuronal cells, and was significantly reduced in glial cells. MTZ alone in absence of Aβ, used as a control, did not have any effect on caspase 9 activity. Importantly, caspase 3—the executioner caspase, activated by caspase 9, and capable of inducing synaptic dysfunction and Tau tangle formation in the AD brain (D'Amelio et al., 2011; de Calignon et al., 2010)—was also activated after Aβ challenge in neuronal and glial cells, as indicated by the green fluorescence shown after immunostaining of active-caspase 3 in FIG. 4C.

As for caspase 9, active-caspase 3 staining and activity of caspases 3/7 measured by luminescence (FIG. 4D), were greatly suppressed when Aβ was co-incubated with MTZ at both concentrations, suggesting a protective effect of the CAI on the downstream neurotoxic effects of Aβ, known to be mediated by these proteases (Burguillos et al., 2011; D'Amelio et al., 2011). Since caspase activation, as well as neuronal and glial dysfunction, are often induced by over-production of mitochondrial and cellular reactive oxygen species (ROS), the inventors tested weather MTZ affected cellular and mitochondrial Aβ-mediated ROS production.

Figure 4B:
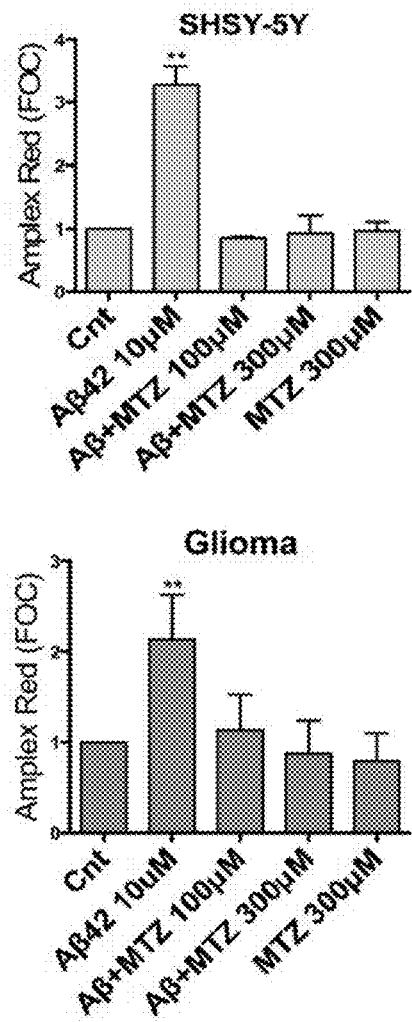

After 24 hours treatment with Aβ42 in the presence or absence of MTZ, the levels of cellular ROS in neuronal SHSY-5Y and glial cells, measured by fluorescence of the ROS indicator CellROX inside the cells, did not significantly change, albeit 25 μM Aβ42 induced a slight increase in neuronal cells (not shown). Intriguingly, when the levels of $H_2O_2$ produced by isolated mitochondria after treatment with Aβ in the presence or absence of MTZ were analyzed, a significant increase in $H_2O_2$ production by the mitochondria of Aβ-challenged cells was found, which was completely reverted by MTZ for both neuronal and glial cells (FIG. 4B). MTZ alone did not have any effect on $H_2O_2$ production in untreated cells. Notably, $H_2O_2$ is the only ROS that can function directly as a second messenger in a physiologically relevant manner (Ding et al., 2008; Forman et al., 2004; Gill and Levine, 2013; Lee et al., 2011), and has been shown to be directly responsible for the release of CytC from the mitochondria as well as for the activation of caspase-3 and neuronal apoptosis in other models of neurodegenerative disease (Saito et al., 2007; Solesio et al., 2013b; Zhou et al., 2014), suggesting that the prevention of mitochondrial $H_2O_2$ production obtained in the presence of the drug may be associated with the ability of MTZ to inhibit CytC release and reduce caspase activation in the present model.

Hippocampal Caspase 3 Activation and Neurodegeneration Caused by Injected Aβ are Inhibited by MTZ.

Figure 5A:
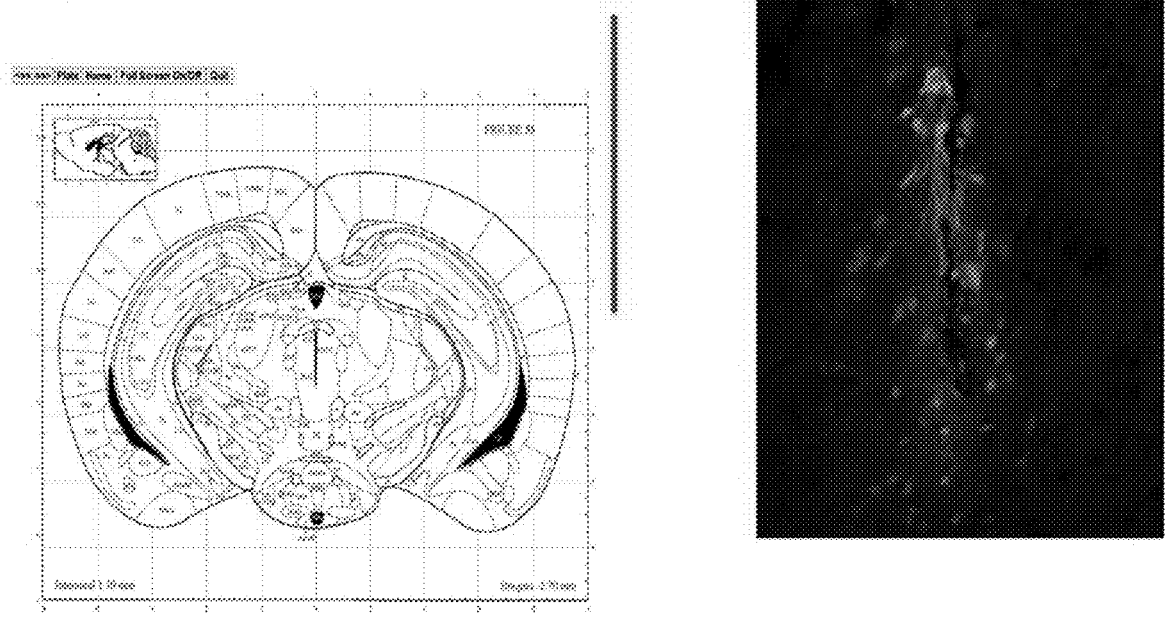
FIGS. 5A-5B. Hippocampal injection of Aβ induces caspase activation in Aβ-positive CA1 cells. Intra-hippocampal Aβ injection in mice was performed as described in Material and Methods. The site of injection is visualized as a red arrow in the Paxinos and Franklin Coordinates Atlas in the left panel (FIG. 5A). Immunohistochemical staining of Aβ was visualized as green fluorescence 1 hour after injection (right panel), and highlights both cellular and parenchymal localization of the peptide around the injection site. Immunohistochemical analysis of the ipsolateral CA1 hippocampal region 4 hours after Aβ injection (FIG. 5B). Red fluorescence represents Aβ, while green fluorescence highlights active caspase 3. Nuclei were stained in blue with To-Pro. Active caspase 3 staining colocalized specifically with CA1 hippocampal cells containing internalized Aβ. Top panels: 40× magnification. Bottom panels: 100× magnification. Results are representative of 5 injected mice.
Figure 5B:
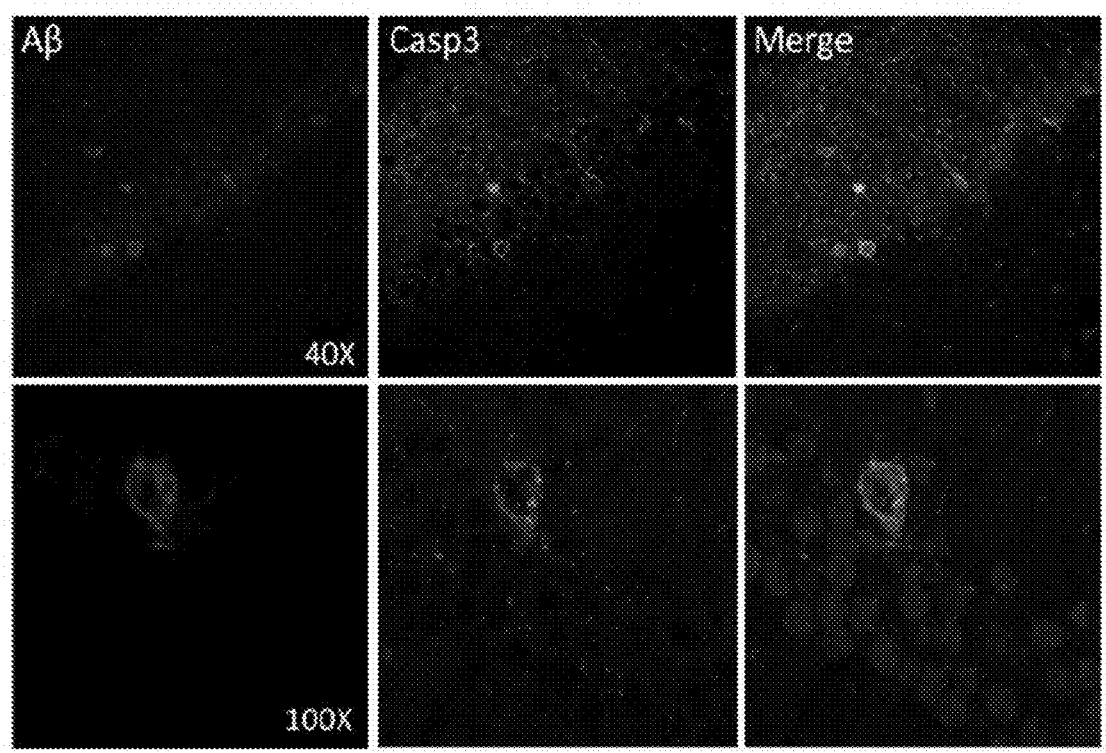
Figure 6:
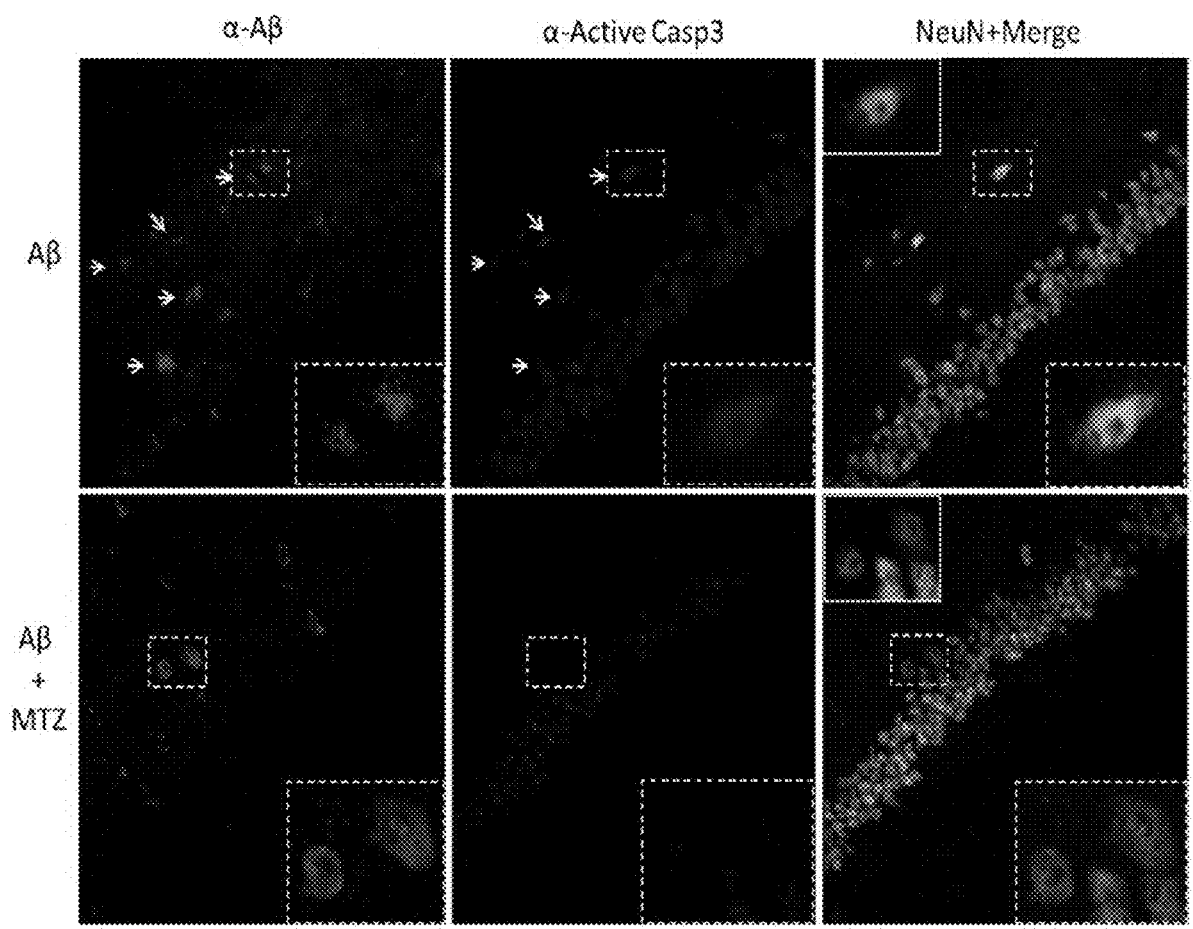
FIG. 6. MTZ inhibits caspase 3 activation in hippocampal neurons presenting internalized Aβ. Aβ was stained in red, active caspase 3 in blue and neurons were visualized in green by NeuN. In absence of MTZ treatment, CA1 neurons with internalized Aβ presented active caspase 3 staining, as in FIG. 4. Arrows highlight cells showing both Aβ and active caspase 3. In mice treated with MTZ, Aβ-positive neurons did not present caspase 3 activation. Inserts delimited by the dashed line represent magnifications of neurons, and show colocalization of caspase 3 with Aβ in absence of MTZ (top panels), or lack of active caspase 3 in Aβ positive neurons for MTZ treated mice (bottom panels). Inserts delimited by the continuous line in the right panels represent NeuN staining of the magnified neurons. Main image: 40× magnification. Inserts: 100×. Results are representative of staining performed in 5 MTZ-treated and 5 untreated mice.
Figure 7:
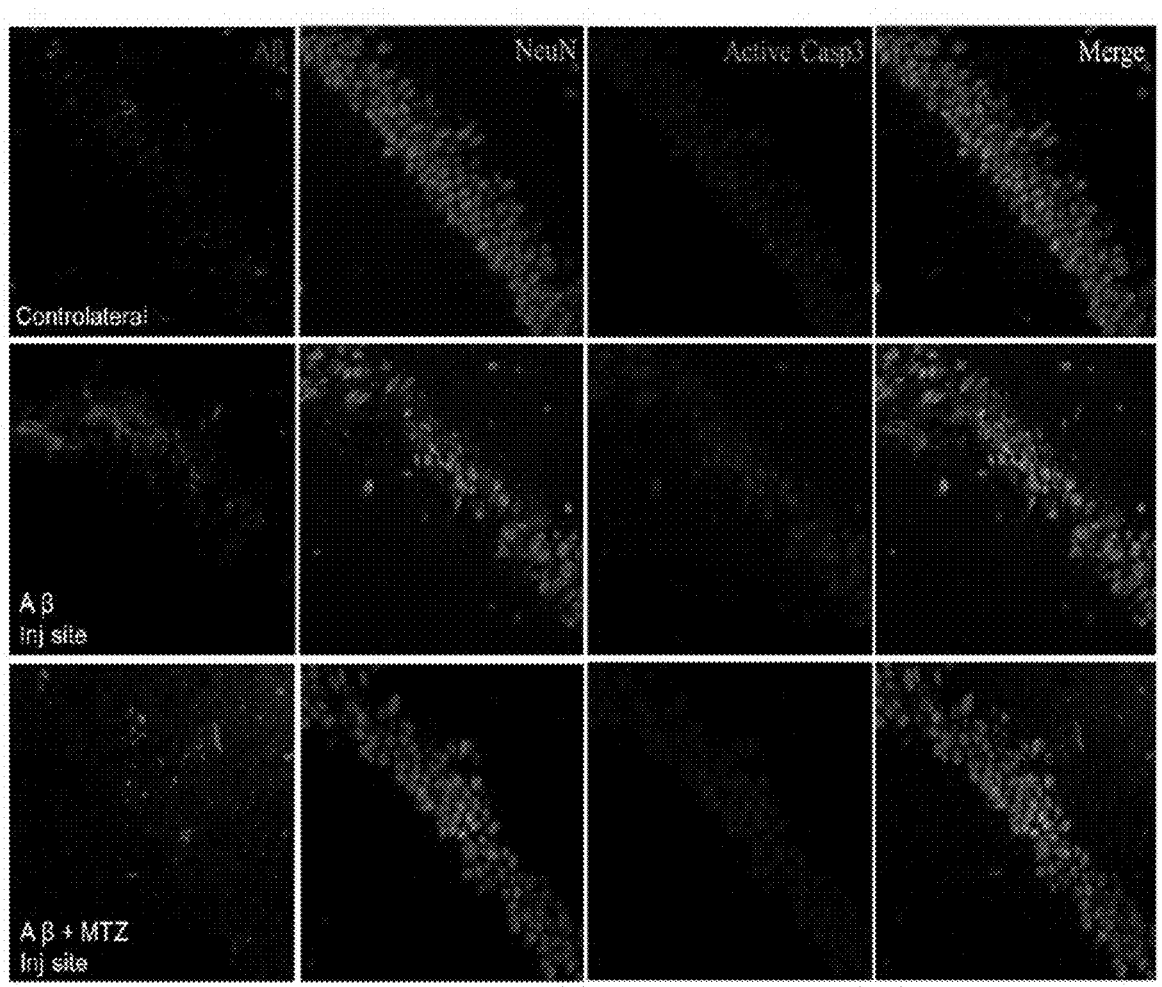
FIG. 7. Effect of MTZ on hippocampal neurodegeneration and caspase 3 activation at the injection site. Immunostaining performed in a region of the hippocampus in close proximity to the injection site (≈100 μm) in mice injected with Aβ in the presence or absence of IP injection of MTZ, and sacrificed after 4 hours. Aβ is stained in red, active caspase 3 in blue, and neurons are stained in green by NeuN. The top panels, used as control, represent the contralateral hippocampus in a mouse injected with Aβ. In the middle panels, neurodegeneration in proximity of the injection site is visualized as loss of NeuN-positive neuronal bodies around the site of Aβ injection compared to the contralateral hemisphere, and is prevented by MTZ (bottom panels). The increase in caspase 3 activation induced by Aβ around the injection site is also inhibited in mice treated with MTZ. N≥4 mice per group.

Injection of oligomeric forms of Aβ in the rodent brain has been shown to provoke long-lasting pathological alterations comparable to the human disease, including caspase activation and neuronal loss (Zussy et al., 2013). Aβ-induced caspase activation was analyzed in vivo using a stereotaxic procedure to deliver Aβ in the hippocampus of wild-type mice, as an in vivo correlate of interstitial Aβ accumulation. FIG. 5A shows the site of injection in the CA3 region of the hippocampus (left panel) and the post-injection localization of the peptide, which was found in the brain parenchyma as well as intracellularly 1 hour after inoculation (right panel). Synthetic Aβ42 is known to form insoluble fibrils very early after solubilization (Chang and Chen, 2014; Fossati et al., 2010), forming in proportion fewer oligomers, which are recognized to be the toxic species responsible for caspase activation and synaptic failure. In light of this, Aβ40-Q22 was chosen, which was shown to form a high level of oligomers after a few hours aggregation, and could persist in oligomeric form for a longer time after injection in the mouse brain compared to Aβ42 (Fossati et al., 2010). In the inventors' model, Aβ40-Q22 specifically induced caspase-3 activation in the hippocampus of mice sacrificed 4 hours after injection. Interestingly, it was observed that caspase 3 was activated specifically only in the neurons containing internalized peptide in the CA1 hippocampal region contiguous to the site of injection (FIG. 5B, 40× magnification in the top panels, 100× in the bottom). Importantly, the activation of caspase-3 induced by Aβ in CA1 neurons was prevented by systemic intra peritoneal (IP) administration of 20 mg/Kg MTZ, as shown in FIG. 6. Neurons stained with NeuN and containing internalized Aβ were positive for active caspase 3 in mice injected with the peptide alone, but were negative for the active caspase when the mice were treated systemically with MTZ 1 hour prior to peptide injection. Furthermore, analyzing the area of the hippocampus immediately adjacent to the CA3 injection site, at a distance from the trace of injection of 100 μm (FIG. 7, top panels), a high amount of intracellular and parenchymal Aβ was observed coexisting with high caspase 3 activation and loss of neuronal NeuN staining, when compared to the corresponding area in the contralateral hippocampus (FIG. 7, middle panels). Loss of NeuN staining has been associated with oxidative stress, neuronal mitochondrial damage and acute neurotoxicity in many reports (Choi et al., 2005; Duffy et al., 2011; Wu et al., 2010), and suggests neurodegeneration in the vicinity of the Aβ injection site. Importantly, in mice treated IP with MTZ one hour before peptide injection (FIG. 7, bottom panels), loss of NeuN immunoreactivity and caspase activation in the vicinity of the injection site were significantly reduced, and the injected hippocampus maintained a structure similar to the non-injected side under confocal imaging. Quantification of NeuN, active caspase 3 and Aβ staining in the vicinity of the injection site, reported in FIG. 9A, confirmed these findings. The present results indicate that MTZ, when administered systemically, can enter the mouse brain and is effective in preventing Aβ-induced caspase activation and neurodegeneration in an acute in vivo model of amyloid toxicity at concentrations consistent with the human doses of CAIs.

MTZ Prevents Caspase 3 Activation in Active Microglial Cells Containing Internalized Aβ.

Figure 8:
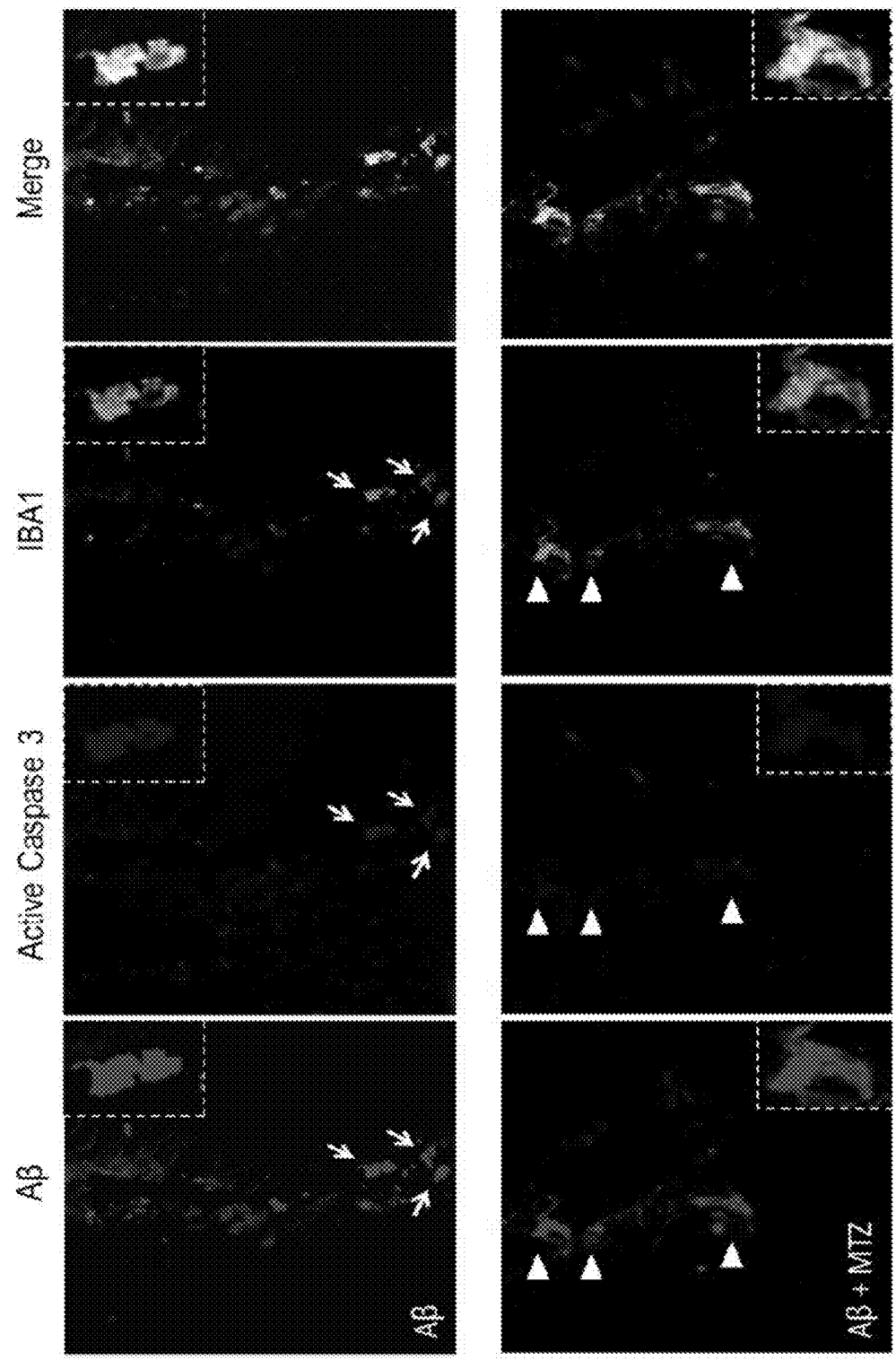
FIG. 8. Effect of MTZ on caspase 3 activation in reactive microglia around the injection site. Staining at the injection site shows Aβ in red, active caspase 3 in blue and reactive microglia, stained by IBA1, in green. Some of the cells internalizing Aβ at the injection site can be identified as active microglia in both MTZ-treated and untreated mice, based on IBA1 reactivity and amoeboid shape. Reactive microglia, positive for IBA1 and presenting internalized Aβ, shows caspase 3 activation in absence of MTZ treatment (top panels, arrows), while IBA1-positive microglia presents a reduced staining for active-caspase 3 in mice injected with MTZ (bottom panels, arrowheads). Notably, the color merge appears white (cells positive for Aβ, IBA1 and active-caspase 3) in Aβ-injected mice, while it's yellow (merge of IBA1 and Aβ) in mice treated with MTZ before peptide injection.

Activated microglial cells, the resident immune cells of the central nervous system, play prominent roles in the pathogenesis of neurodegenerative disorders, including AD. However, uncontrolled and over-activated microglia can trigger neurotoxicity (Burguillos et al., 2011). In the mature brain, microglial cells typically exist in a resting state characterized by a ramified morphology. In response to certain cues such as brain injury or immunological stimuli, they are readily activated and undergo a dramatic transformation from their resting ramified state into an amoeboid morphology (Block et al., 2007). Recent reports indicate that microglial activation is capable of both initiating additional neuronal loss and amplifying ongoing neuronal damage, indicating that microglia might be crucial to the etiology and the progressive nature of neurodegenerative diseases. Microglial activation in cell and animal models of inflammation involves caspase activation, and inhibition of the cascade in microglia prevents neurodegeneration. Accordingly, significant cytoplasmic expression of active caspase-3 was found in microglial cells of postmortem AD brains, compared with controls (Burguillos et al., 2011). Here the presence of active caspase 3 in microglia activated by Aβ injection was analyzed. After injection of Aβ in the presence or absence of MTZ, a similar number of Aβ-positive cells around the injection site presented IBA1 staining, indicative of microglial activation (FIG. 8). While cells positive for both IBA1 and Aβ presented high active-caspase 3 fluorescence in mice injected with only Aβ (FIG. 8, top panels, arrows), active-caspase 3 staining was notably lower in mice that were previously given IP injections of MTZ (FIG. 8, bottom panels, arrowheads), as confirmed by the yellow color of these cells in the merged image, compared to the white color in absence of MTZ. Quantification of the area occupied by active caspase 3, IBA1, and their ratio in microglial cells at the injection site, are reported in FIGS. 9A-9B and confirm a significant decrease of caspase 3 activation in microglia in the presence of MTZ. The ability of MTZ to decrease caspase 3 activation in reactive microglia is indicative of a protective effect of the compound not only towards glial cell death and the toxic effects of an excessive inflammatory reaction, but also against the microglia-mediated amplification of the neurodegeneration process.

Discussion

The data presented herein demonstrate that Aβ-induced neuronal and glial mitochondrial dysfunction, caspase activation and apoptotic cell death can be prevented by the CAI MTZ. The release of CytC and activation of both caspase 9 and the effector caspase 3 caused by Aβ challenge were prevented by MTZ in neuronal and glial cells in culture and in the mouse brain. MTZ was also able to hinder terminal DNA fragmentation—indicative of apoptotic cell death—in both cell types, without affecting the peptides' aggregation patterns. Moreover, it is indicated herein that the primary mechanism of action of MTZ involves the inhibition of mitochondrial $H_2O_2$ production and the subsequent prevention of mitochondrial degeneration and CytC release in both cell types. Importantly, after intra-hippocampal Aβ injection in the mouse brain, which resulted in cellular uptake of the peptide and activation of caspase 3 in neurons and microglia, administration of MTZ was able to prevent neuronal and glial caspase activation as well as hippocampal neuronal loss.

Mitochondrial dysfunction and loss of $\Delta\Psi$ are known as early events in the AD pathology (Balietti et al., 2013; Eckert et al., 2003a; Swerdlow et al., 2010), preceding the activation of caspases and memory loss (Atamna and Frey, 2007; Beal, 2005). Mounting evidence suggests a role for the activation of caspases in the AD brain and proposes that this event may occur through stimulation of death receptor (DR) pathways by Aβ oligomeric species. The inventors' recent work demonstrated that oligomers and protofibrils of WT-Aβ40, as well as its vasculotropic mutants, engaged DRs activating caspase 8 and 9 and inducing mitochondrial dysfunction, with loss of $\Delta\Psi$ and CytC release in cerebral endothelial and neuronal cells in culture (Fossati et al., 2010; Fossati et al., 2012a; Fossati et al., 2012b; Fossati et al., 2013). The possibility of blocking early mitochondrial damage in the brain using CAIs, reducing production of mitochondrial ROS, and the resulting release of CytC and activation of caspases, could represent an effective approach in both prevention and therapy for AD.

The data presented herein provide evidence of a protective effect of a CAI against amyloid challenge in the mouse brain. Carbonic anhydrases (CAs) are a family of enzymes catalyzing the conversion of $CO_2$ to bicarbonate and protons. They have a role in a number of physiological processes such as diuresis, production of body fluids, gluconeogenesis and lipogenesis. Sixteen mammalian isozymes have been discovered, among which CA VA and CA VB are mitochondrial. Several CAIs, among them MTZ, have high activity against mitochondrial CA. Noteworthy, CAIs are safe, have been used chronically for many years against glaucoma, and can easily cross the blood brain barrier. CAIs such as acetazolamide are well tolerated in humans up to a 1000 mg daily dose and are also currently FDA-approved for the prevention of acute mountain sickness and related high-altitude cerebral edema, confirming the efficacy of this and analog sulfonamides in the brain and the safety of their systemic administration (Wright et al., 2008).

The data herein demonstrates that MTZ is effective at inhibiting the overproduction of mitochondrial $H_2O_2$ induced by Aβ. $H_2O_2$ is known to be membrane permeable and to act as a second messenger (Almasalmeh et al., 2014; Ding et al., 2008; Forman et al., 2004; Gill and Levine, 2013; Lee et al., 2011). Generation of $H_2O_2$ was shown to precede loss of $\Delta\Psi$ and CytC release during apoptosis (Luo et al., 2012; Tada-Oikawa et al., 1999), suggesting that the observed effects of MTZ on the inhibition of $H_2O_2$ production induced by Aβ could be instrumental to reduce mitochondrial dysfunction and cell death in AD. The membrane permeable properties of hydrogen peroxide and its ability to escape the cellular environment also explain the present findings showing changes in the release of $H_2O_2$ by mitochondria isolated from Aβ-treated cells, coexisting with the lack of significant changes in cell ROS inside whole cells (after removal of their extracellular media). The ability of MTZ to reduce $H_2O_2$ and prevent loss of mitochondrial $\Delta\Psi$—both associated to the inhibition of CytC release—may be key mechanisms contributing to the prevention of caspase activation and the resulting apoptosis in the present model.

In the data herein, it is shown that MTZ can effectively inhibit $H_2O_2$ production, as well as CytC release and caspase activation not only in neuronal, but also in glial cells, decreasing the levels of active-caspase 3 in IBA-1 positive microglia in the Aβ-injected mouse brain. Although mediated by different sets of receptors, a common deleterious pathway involving oxidative stress induces neuronal death and amplifies microglial activation to drive spreading neurotoxicity (Block et al., 2007). Upon depletion of the cell's antioxidant defense, $H_2O_2$ could act to amplify the pro-inflammatory function of microglia. High levels of intracellular ROS might result in microglial death (predominantly by apoptosis), similar to that which occurs in phagocytes in the periphery. Whereas acute microglial over-activation is deleterious, active microglia might also be involved in neuronal maintenance, repair and possibly protection. Therefore, the ideal therapeutic approach would likely involve attenuation of the microglial response to levels that are no longer deleterious, rather than the elimination of the microglial response altogether (Choi et al., 2005). This seems to be the case in the present model in the presence of MTZ, which preserves microglial activation, as shown by IBA1 staining, while reducing the activation of caspase 3 below the threshold able to cause DNA fragmentation and cell death, as confirmed by the present in vitro data.

Inhibition of caspase activation protected against neuronal loss in several animal models of brain diseases involving activated microglia, including ischaemia/stroke, acute bacterial meningitis, and parkinsonism models (Braun et al., 1999; Burguillos et al., 2011; Cutillas et al., 1999; Schulz et al., 1998), and microglia exposed to the pro-inflammatory agent LPS failed to be toxic to neighboring neurons when caspase 3/7 were inhibited chemically or by siRNA. Thus, a pharmacological approach employing CAIs in the AD brain, achieving simultaneously inhibition of mitochondrial $H_2O_2$ production, CytC release and caspase activation in neuronal and glial cells without inhibiting physiological levels of microglial activation, could have the potential to prevent neurodegeneration both directly, restoring neuronal mitochondrial function, and indirectly, avoiding excessive microglial activation and the derived neurotoxicity. Further studies in transgenic mouse models of AD are currently being performed to clarify the best treatment strategy and the long-term in vivo effects of CAIs in a chronic model of amyloidosis.

Supporting the potential of a future translation of the inventors' approach to human therapy, after allometric scaling the concentration of CAI used in the current studies (20 mg/kg), was consistent with the human use of the drug (the human corresponding dose is 2.6 mg/kg, or 182 mg for a 70 kg person, which is consistent with the FDA approved dose for MTZ of 100 mg every 8 hours). Furthermore, the current chronic use of MTZ in glaucoma patients suggests the general tolerability of any side effects.

Conclusions

The data described herein suggests the molecular mechanism of action of MTZ against Aβ-mediated $H_2O_2$ production and the resulting mitochondrial dysfunction and caspase activation in neuronal and glial cells, demonstrating the efficiency of the compound in an in vivo acute model of amyloid-mediated toxicity. Overall, the present findings support the potential of repurposing MTZ and analog FDA-approved CAIs as new therapeutic strategies for AD and related cerebral amyloidosis.

Example 2. Inhibition of Carbonic Anhydrase Prevents Amyloid β Mitochondrial Toxicity in Neuronal and Endothelial Cells Materials and Methods Reagents Dulbecco's Modified Eagle medium:F12 1:1 (DMEM:F12), F-12 medium, penicillin-streptomycin and fetal bovine serum (FBS) were purchased from Gibco-Invitrogen (Carlsbad, Calif., US); anti-active caspase-3 antibody from Santa Cruz Biotechnology (Dallas, Tex., US); protease inhibitors and cell death detection ELISA plus kit from Roche (Basel, Switzerland); endothelial cell growth medium (EBM-2) and the growth supplements from Lonza (Basel, Switzerland); MTZ, AZT, 1,1,1,3,3,3-hexafluoro-2-propanol (HFIP), dimethyl sulfoxide (DMSO), Triton X-100 solution, bovine serum albumin (BSA), sucrose, mannitol and Tris-HCl, phenylmethylsulfonyl fluoride (PMSF) and p-trifluoromethoxyphenylhydrazone (FCCP) from Sigma-Aldrich, (St. Louis, Mo., US); caspase-Glo 9 assay and Cell Titter-Glo assay from Promega (Madison, Wis., US); Amplex Red hydrogen peroxide/peroxidase assay kit and CM-H2DCFDA (general oxidative stress indicator) from ThermoFisher (Waltham, Mass., US); paraformaldehyde 20% (PFA) from Electron Microscopy Sciences, (Hatfield, Pa., US); Rhod-2 AM, Fluo-4 AM, tetramethylrhodamine methyl ester (TMRM), Hank's Balanced Salt Solution (HBSS), mitotracker red, CellROX deep red reagent, pHrodo green AM and Hoechst 333258 from Thermo Fisher (Waltham, Mass., US) and Alexa Fluor 488 antibody from AbCam (Cambridge, United Kingdom).

Cell Cultures

The dopaminergic neuroblastoma SH-SY5Y cell line was purchased from the American Type Culture Collection (ATCC, Manassas, Va., US) and grown as reported in [74]. Briefly, DMEM:DCFF12, supplemented with 20 units/mL penicillin-streptomycin and 15% (v/v) FBS, was used. Immortalized human brain microvascular endothelial cells, hCMEC/D3 cells [75] (D3), were obtained from Babette Weksler [75] and grown in complete EBM-2 medium, containing all the growth supplements (Hydrocortisone, hFGF-B, VEGF, R3-IGF-1, ascorbic acid, hEGF, GA-1000 and heparin), 20 units/mL penicillin-streptomycin and 5% FBS. Both cell lines were grown in a humidified cell culture incubator, under a 5% $CO_2$ atmosphere and at 37° C.

Drug Preparation

MTZ and AZT were both dissolved in DMSO to stock solutions of 300 mM and kept at −20° C. until the day of the experiment. The drugs were thawed at room temperature and then dissolved in the specific medium used in each experiment to the final concentrations, (100 and 300 μM in the case of MTZ and 10 to 100 μM for AZT).

Aβ Peptides

Synthetic Aβ42 was synthesized using N-tert-butyloxy-carbonyl chemistry by James I. Elliott at Yale University and purified by reverse-phase high-performance liquid chromatography on a Vydac C4 column (Western Analytical, Murrierta, Calif., US) [76] Aβ40-Q22 (the Dutch genetic variant, containing the E22Q substitution) was synthesized by Peptide 2.0 Inc. (Chantilly, Va., US) and purified by HPLC/MS. Purity was >95%. Aβ homologs were dissolved to 1 mM in HFIP, incubated overnight to break down pre-existing β-sheet structures [9], and lyophilized. Peptides were subsequently dissolved in DMSO to a 10 mM concentration, followed by the addition of deionized water to 1 mM concentration and by further dilution into the medium in which the experiments were run, to a final concentration of 10 μM in the case of Aβ42 and to 50 μM in the case of the Aβ40-Q22. Peptide treatments were performed in EBM-2 supplemented with FBS 1% and in DMEM:F12 with no FBS, for the D3 and the SH-SY5Y cell lines, respectively.

Peptide Pre-Aggregation

Peptide pre-aggregation to obtain oligomeric preparations was performed following the protocol published by Dahlgren et al., [77]. Briefly, lyophilized peptides were re-suspended in DMSO to a 5 mM concentration, immediately prior to use. After that, diluted peptides were dissolved in F12 medium with no phenol red or FBS to a final concentration of 100 μM and they were incubated at 4° C. for 24 h, in order to allow the formation of the oligomers. 24 h later, the oligomers were added to the cultures, at the desired concentrations, alone or in co-treatment with the different drugs.

Immunocytochemical Evaluation of Active Caspase 3

SH-SY5Y and D3 cells were plated on 15 mm optical borosilicate poly-L-lysine-coated sterile glass covers (ThermoFisher, Waltham, Mass., US) at a 70% confluence. After 24 hours, cells were treated with the peptides, the drugs or the different combinations of both of them, rinsed in PBS 1×, and fixed with 4% paraformaldehyde for 20 minutes. After that, the coverslips were washed once for 5 minute with PBS 1×, room temperature and twice for 5 minutes with cold PBS 1×. Cells were then permeabilized and blocked for 1 h with BSA 20 mg/mL+Triton 0.3% on PBS and incubated with the anti-active caspase-3 antibody, on PBS containing BSA 5 mg/mL, for 2 h. Next, cells were washed three times for 5 min each with PBS 1× and incubated with the secondary antibody (Alexa Fluor 488 anti-mouse antibody), at a 1:200 dilution in PBS containing BSA 5 mg/mL for an additional hour in the dark. Cells were then washed three times in the dark with 1 mL of PBS 1× and mounted on cover slips (ThermoFisher, Waltham, Mass., US). After mounting, cells were imaged, using a Nikon Eclipse Ti inverted microscope with a 20× objective (Nikon, Chiyoda. Tokyo, Japan).

Caspase 9 Activation

Cells were plated at a confluence of 10.000 cells per well in 96-wells microplate luminescence microtiter (ThermoFisher, Waltham, Mass., US). The day after, cells were treated with the peptides and/or drugs for the experimental times. After that, caspase-Glo 9 assay was performed, following the protocol provided from the manufacturer. Luminescence was measured using a FlexStation 3 Multi-Mode Microplate Reader (Molecular devices, Sunnyvalem Calif., US).

CellROX 10.000 cells of either SH-SY5Y or D3 cells were plated on 96-wells plates. The day after, cells were treated with the peptides and/or the drugs for the established experimental times. CellROX reagent was then added, directly, to the growing media, at a final concentration of 5 μM. 10 μg/mL of Hoescht 333258 was also added to the medium containing the CellROX reagent, in order to dye cell nuclei. Cells were incubated with both CellROX and Hoescht 333258, at 37° C., for 30 min., just before the ending time-point of the treatment. After 30 min., the medium was removed and cells were washed once in PBS 1× at room temperature. Cells were then fixed with 4% PFA on PBS for 15-20 min., at room temperature and washed once again with PBS 1×. Cells were imaged within 2 h, using a FlexStation (Molecular devices, Sunnyvalem Calif., US).

DCFDA

Cells were plated on 96-wells microplate fluorescence microtiter (ThermoFisher, Waltham, Mass., US), and treated with peptides and/or drugs on phenol red free medium, with no serum in the case of the SH-SY5Y cells and 1% serum on the D3. After the treatments, cells were washed once with HBSS. After this, cells were stained in the dark with HBSS containing 10 μM DCFDA (previously dissolved to 1 mM in DMSO) and 10 μM mitotracker red (also dissolved to 1 mM with DMSO) for 30 min at 37° C., in the incubator. Cells were then washed three times with HBSS and they were allowed to recover in complete media, phenol red free, for 1.5 h, in the incubator. Fluorescence was measured using a FlexStation (Molecular devices, Sunnyvalem Calif., US).

AmplexRed

Cells were plated on 6-wells plates and treated with the peptides and/or drugs for the experimental times. Plates were centrifuged for 10 min at 1.000 RPM and washed twice with PBS 1×. After that, 500 μL of homogenization buffer (75 mM sucrose, 225 mM mannitol, 5 mM Tris-HCl pH=7.4, 1 mM PMSF and protease inhibitor cocktail) was added. Cells were scraped in this buffer, collected in glass tubes and grinded exactly 80 times with a pellet pestle, keeping everything always on ice. Cells were then centrifuged at 2.800 RPM for 5 min at 4° C. The supernatant was collected and centrifuged again at 2.800 RPM for 5 min at 4° C. The supernatant was again collected and centrifuged at 10.500 RPM for another 5 min at 4° C. After this, the supernatant was discarded and the pellet was re-suspended in 100 μL of homogenization buffer. The samples were centrifuged again at 10.500 RPM for 10 min at 4° C., the supernatant was discarded and the pellets (mitochondrial fractions) were re-suspended on 50 μL of homogenization buffer. A protein concentration assay on mitochondrial protein was performed, using the Pierce BCA Protein Assay Kit (ThermoFisher, Waltham, Mass., US) and following the instructions provided by the manufacturer. After that, mitochondrial fractions containing equal amounts of mitochondrial proteins were placed on 96-wells microplate absorbance microtiter (ThermoFisher, Waltham, Mass., US) and the AmplexRed assay was ran, following the instructions provided by the manufacturer. Absorbance was measured by using a FlexStation (Molecular Devices, Sunnyvalem Calif., US).

Cell Death ELISA Assay 20.000 cells per well were plated on 24-wells plates. The day after, cells were treated with peptides and/or drugs, following the experimental conditions. After that, the extent of apoptosis caused by the different peptides, as well as the hypothetic protective effect of the drugs, was assessed by quantifying the formation of nucleosomes, by using the Cell Death ELISA plus kit, following the manufacturer instructions.

Mitochondrial and Cytoplasmic Calcium Assay

This assay was performed as published in [60]. Briefly, cells were plated on 25 mm optical borosilicate poly-L-lysine-coated sterile glass covers, (ThermoFisher, Waltham, Mass., US) at a 70% confluence. 24 hours later, cells were loaded with 5 µM Rhod-2 AM or 2.5 µM Fluo-4 AM on HBSS for 45 minutes. Then, cells were washed twice with HBSS and incubated for another additional 15 minutes on fresh HBSS, without Rhod-2 AM or Fluo-4 AM. After that, HBSS was replaced again by fresh HBSS, glasses were mounted on microscopy chambers and experiments were conducted, after adding the pre-aggregated peptides and/or the drugs. Cells were mounted on Sykes-Moores chambers (BellCo, Vineland, N.J., US) and imaged every 15 seconds for 45 min, at a 20× magnification, using a Nikon fluorescent microscope (Chiyoda, Tokyo, Japan). Images were processed using NIS-Elements and ImageJ software. Due to the rapidity of this experiment, the peptide was pre-aggregated as described above to obtain oligomers before being added to the cells.

TMRM Assay

The assay was performed following the protocol showed in [78]. Briefly, cells were plated on 25 mm optical borosilicate poly-L-lysine-coated sterile glass covers (ThermoFisher, Waltham, Mass., US) at a 70% confluence. The day after, cells were washed twice with HBSS and charged with 600 nM TMRM on HBSS. Cells were then incubated for 20 min in the incubator, at 37° C. and washed again with HBSS. After that, the medium was replaced by HBSS containing 150 nM of tetramethylrhodamine methyl ester (TMRM), in order to maintain the equilibrium distribution of the fluorophore. Cells were then mounted on Sykes-Moores chambers (BellCo, Vineland, N.J., US) and treated with the different drugs and/or peptides. An image was taken at minute 0 and at minute 45, after adding the drugs and/or peptides. In this experiment, the peptide was pre-aggregated as above before adding it to the cells.

pH Measurement

Cells were plated on 96-wells microplate fluorescence microtiter (ThermoFisher, Waltham, Mass., US). The day after, cells were treated with the different drugs and/or peptides. After this, intracellular pH measurement was performed by using the pHrodo red AM kit, following the indications provided by the manufacturer.

ATP Measurement

Steady state levels of ATP were estimated using the Cell Titter-Glo, according to manufacturer's instructions. Briefly, $5 \times 10^3$ cells per well of both D3 and SHSY cells were plated on 96-wells plates. The day after, cells were treated with either 10 µM Q22 or 50 µM Ab42 peptides, respectively. Peptides were added alone or in combination with increasing concentrations of MTZ (100 and 300 µM) or AZT (30 and 300 µM). Controls were treated with either DMSO or 5 µM oligomycin. After 3 hours of treatment, the plates containing the cells were equilibrated to room temperature for 30 minutes prior to addition of the luciferin/luciferase/cell lysis mixture. Absolute luminescence from quadruplicate experiments was recorded using a SpectraMax plate reader (Molecular Devices, Sunnyvalem Calif., US).

Grip Strength Measurement

The grip strength test was used to measure neuromuscular function and specifically assesses maximal muscle/grip force of the forelimbs (only) or both the fore and hind limbs combined. Motor performance was assessed by the horizontal grasping force applied by the rodent to a specialized stainless steel grid that is connected to a sensitive, electronic force sensor (Bioseb In Vivo Research Instruments). For forelimb (only) measurement, the mouse was gently lowered over a ~6×10 cm wire grid, keeping the torso horizontal and allowing only its forepaws to attach to the top portion of the grid. With the base of the tail held gently but firmly between thumb and forefinger, the mouse was pulled gently back away from the grid, ensuring that the torso remains horizontal, until the animal loses grip of the grid. For combined fore and hindlimb measurement, the procedure was identical to the forelimb-only procedure except that mouse was lowered to allow both fore and hind paws to attach to the grid before any measurements were taken. Animals were placed back into their home cage after forelimb or combined limb assessment, with a minimum of 30 period between tests on the same animal.

The peak force or maximal grip strength value of the mouse was recorded in grams of force as set and displayed on the Bioseb apparatus. To ensure maximal reliability, each measurement of interest (e.g., forelimb or combined) was repeated consecutively for each mouse to obtain 5-6 replicates. Measurements were taken by an experienced experimenter who ensured that animals were comfortable being handled, placed at a consistent location on the grid and were neither biting or releasing their grip during each replicate. A truncated mean (mean of replicates after the smallest and largest readings were removed) was calculated for each subject. Animals are weighed on the day of testing and the computed grip strength values were normalized against body weight.

Barnes Maze Spatial Memory Testing

The Barnes Maze was used to provide an index of spatial learning and memory. The task capitalizes on the motivation of mice to seek refuge from loud, open and brightly-lit spaces. Mice were trained across a series of trials to successfully navigate to a hidden escape chamber using information provided by distal spatial cues. The Barnes Maze consists of a relatively large (36" in diameter), circular platform with a beige textured surface that is elevated 36" from the floor (San Diego Instruments, San Diego USA). The platform has twenty 2" diameter holes that are equally spaced around the periphery of the platform (1" from the edge). A grey plastic escape box (~10 cm×8.5 cm×4 cm) is located under only one of the holes, the location of which is constant for each subject but variable across subjects and counterbalanced across groups. The surface of the Barnes maze is brightly-lit (500-600 lux), illuminated by an overhead lamp (60-100 W) placed approximated 30" above the center of the platform. Visible distal cues were placed around the room and remained constant throughout the testing period. An overhead video camera and specialized software (Noldus Ethovision 11.5) was used to track the locomotor trajectories of the mice. Mice were trained for six consecutive daily testing sessions (2 trials/day for 5 days, and probe test on day 6).

On each testing day, mice were brought to the testing room for a minimum of 30 mins prior to testing in order to acclimate to transport and testing room conditions. On the first day of testing, each mouse was gently removed from its home cage by the base of its tail and placed in the center of the platform and kept within an inverted 500 ml beaker for 1 min. A white noise generator (San Diego Instruments) was turned on (~90-100 dB) when the mouse was placed onto the maze. After the 1-min period, the beaker was slowly moved (over the course of 1 min) to the target hole with the mouse freely moving but confined underneath. Care was taken not to catch the tail or paws of the mouse while moving the beaker. The mouse was then permitted, or was gently guided by the experimenter using the beaker, to enter the escape box and was given 2 min inside before being transported back to its home cage within the escape box. The white noise was turned off as soon as the mouse entered the escape box. The platform and start box were cleaned thoroughly with 30% ethanol and allowed to dry fully before each trial. To ensure that distal spatial cues rather than local intramaze cues were being used to help guide navigation to the escape box, the maze was rotated after each training trial and the escape box re-positioned to always be in the identical spatial location within the room.

After the initial beaker trial, each mouse was given 2 training trials per day. During training trials, mice were placed in the center of the platform within an plastic 6"l×6"w×8"h start box. The white noise generator was turned on and, after 10-15 s delay, the start box was lifted. The mouse was permitted a maximum of 3 min to find the designated hole and escape box. When a mouse entered the escape box the white noise was turned off and they were given approximately 1 additional min inside the box before being transferred back to the home cage. If the mouse did not find the escape hole within the 3 min limit, it was slowly guided to the target hole under the inverted beaker (as described above), and given 1 min inside the box before being transferred back to the home cage. A 90-120 min inter-trial interval separated the two training trials on each daily session.

Twenty four hours after (Day 6) the fifth training session, a 3-min probe trial was given, conducted identically as the training trials but where the escape box had been removed. This probe was used to examine search behavior patterns and to help control for possible strategies that use local cues from the escape box.

Spatial learning and memory was inferred based on the latency, distance and number of errors (other holes visited) that was required for the mouse to successfully navigate to the escape box. All parameters were derived from automated detection and tracking of the videos for each trial (Noldus Ethovision 11.5) and independently assessed by an experienced observer.

Statistical Analysis

Statistical significance of differences between groups was determined by Student's test or two-tailed Student's test. Moreover, in experiments containing more than two groups, the statistical significance was determined by ANOVA with turkey post hoc test. For the statistical analysis and the graphical representation, Origins Lab (Northampton, Mass., USA) software and GraphPad Prism (GraphPad, La Jolla, Calif.) were used. Values of $P \leq 0.05$ were considered significant.

Results

Aβ-Induced Apoptosis and Caspase Activation is Prevented by CAIs.

Apoptotic cell death is a well-known contributor to neurovascular degeneration in AD (reviewed in [36, 37]). Caspase activation and Cytochrome C (CytC) release play key roles in the apoptotic process. It has been previously demonstrated the protective effect of MTZ against apoptotic cell death in models of Aβ-induced toxicity [26]. Herein it is shown that the protective effect observed for MTZ on caspase activation, CytC release and apoptosis, was also achieved using a different CAI, AZT.

It has been confirmed that Aβ-induced caspase 3, caspase 9 activation and DNA fragmentation (FIG. 10A-10D), as well as CytC release (FIG. 11A-11B), were inhibited by MTZ starting at 100 μM concentration. The effect of AZT on the same cell death pathways was then analyzed. Interestingly, ATZ was able to exert a protective effect on caspase 3 and 9 activation, CytC release and apoptosis at concentrations 10 times lower than MTZ (starting at 10 μM) (FIGS. 10A-10D and FIGS. 11A-11B). ATZ had an effect similar to that shown in the inventors' previous work [26] for MTZ, completely reverting caspase activation and CytC release induced by Aβ. Mitochondrial membrane depolarization in response to Aβ and its inhibition in the presence of ATZ and an inactive analog of ATZ was measured by TMRM in SH-SY5Y neuronal cells (FIG. 10D), and it was found that the inactive ATZ analog had a similar effect on membrane depolarization as ATZ.

Aβ Challenge Causes Mitochondrial Membrane Depolarization and Increase in Mitochondrial $H_2O_2$ Production, Both Counteracted by AZT and MTZ.

Figure 10A:
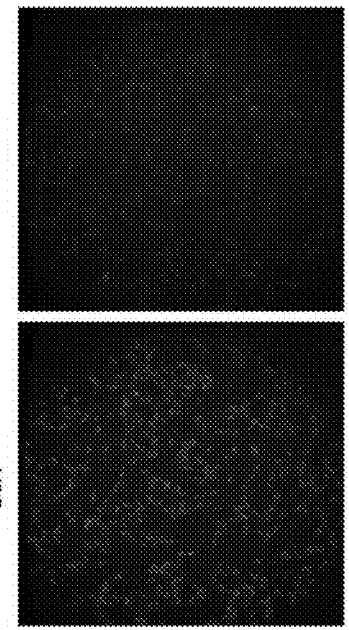
FIGS. 10A-10D. Mitochondrial membrane depolarization in response to Aβ-induced toxicity is prevented by CAIs. Graphs showing mitochondrial membrane depolarization in (FIG. 10A) SH-SY5Y cells and (FIG. 10B) D3 cells. The effect is counteracted by the CAIs in both cases.
Figure 10B:
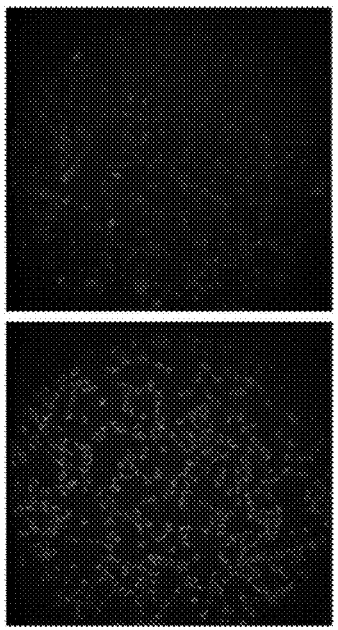
Figure 10C:
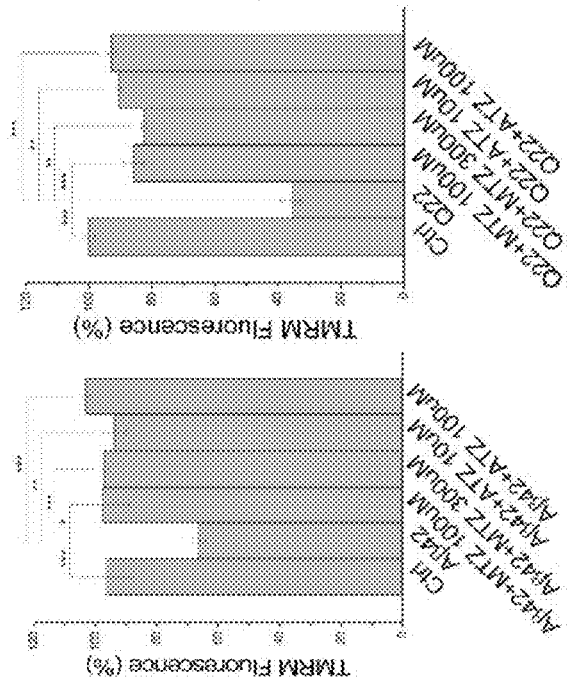
Figure 10D:
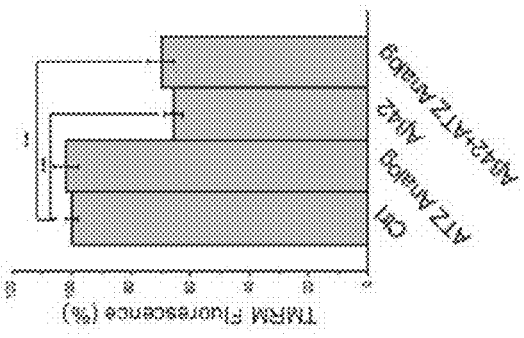
Figure 12A:
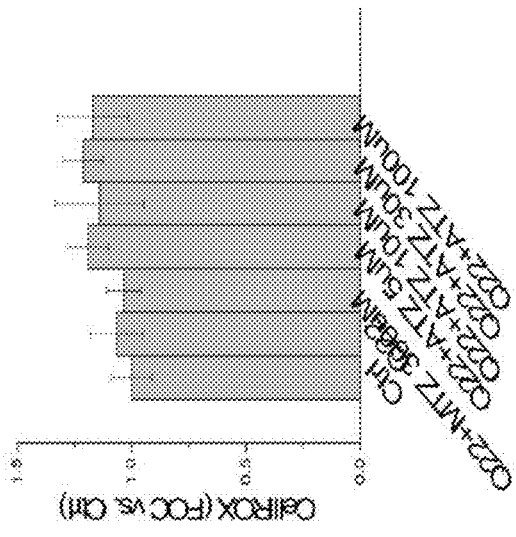
FIGS. 12A-12D. Effect of Aβ-induced toxicity in other cellular ROS. Oxidative stress within the cell in (FIG. 12A) SH-SY5Y and (FIG. 12B) D3 cells were not affected by the Aβ. The same effect was observed when the total levels of ROS within the cells in (FIG. 12C) SH-SY5Y and (FIG. 12D) D3 cell cultures were studied.
Figure 12B:
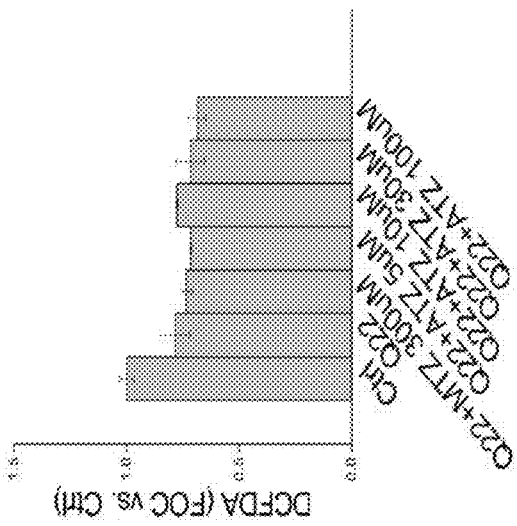
Figure 12C:
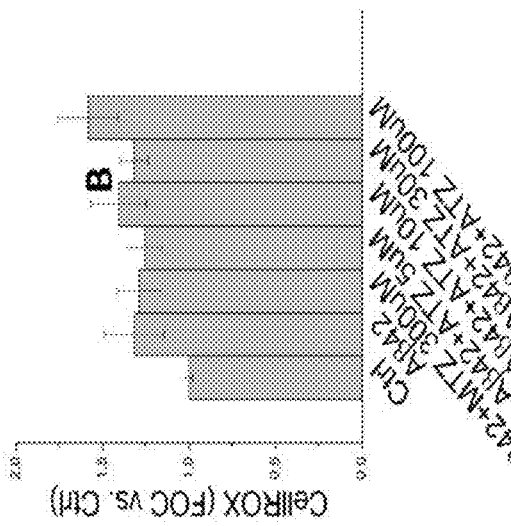
Figure 12D:
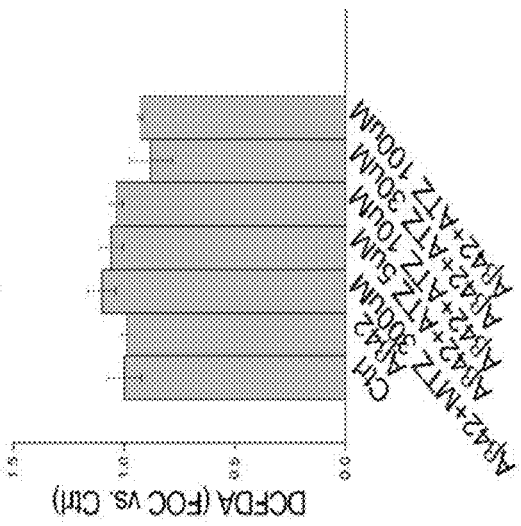

To clarify the molecular mechanisms responsible for the effect of CAIs on the prevention of mitochondrial CytC release and the resulting activation of caspase 9, multiple mechanisms responsible for maintaining mitochondrial function and heath were analyzed. Preserving the proper mitochondrial membrane potential is an essential factor for cell survival and energetic function. Indeed, mitochondrial membrane depolarization is known to precede and facilitate apoptotic cell death [38]. The data herein suggests that aggregated forms of Aβ peptides induce a depolarizing effect on the mitochondrial membrane of neuronal and ECs already after 45 minutes of treatment (FIG. 10A-10C). This effect was especially dramatic in the case of microvascular ECs, where membrane depolarization ($\Delta\Psi$), measured by TMRM, was reduced more than 60% by Aβ (FIG. 12A-12B). Both MTZ and AZT, at any of the used concentrations, were able to rescue $\Delta\Psi$ to values similar to those observed under control conditions. The concentrations of 100 μM was used as starting point for MTZ due to the inventors' previous data indicating an effect of this or higher doses on prevention of cell death [23, 39]. The same effect was observed when the total levels of ROS within the cells were studied in SH-SY5Y (FIG. 12C) and D3 (FIG. 12D) cell cultures. In line with the cell death experiments shown in FIG. 10A-10D, ATZ, when added to the peptides, was able to prevent loss of $\Delta\Psi$, showing membrane potential at the levels of control cells, already at 10 μM concentration. When 40 μM FCCP were added after treatment with drugs and peptides, mitochondria were further depolarized, showing that $\Delta\Psi$ was maintained, at least in part, in all the experimental conditions.

Figure 11A:
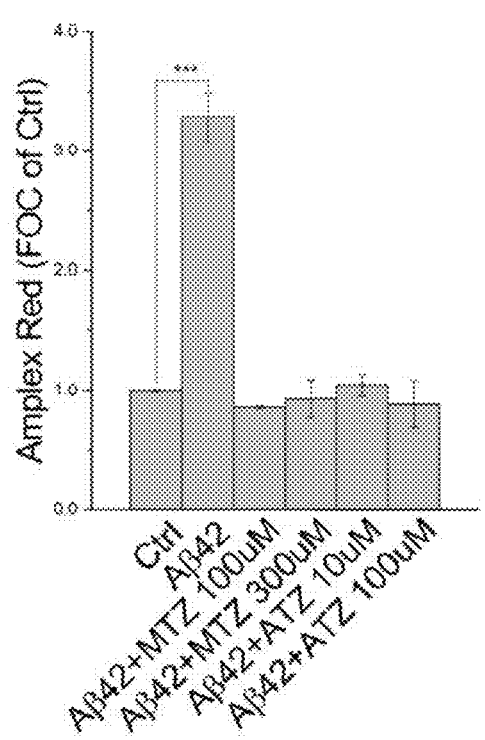
FIGS. 11A-11B. Increase of mitochondrial $H_2O_2$ generation in response to Aβ and inhibition in the presence of CAIs. Data showing relative amount of mitochondrial $H_2O_2$, expressed as FOC of Ctrl, in (FIG. 11A) SH-SY5Y cells and in (FIG. 11B) D3 cells, and the inhibition by MTZ and ATZ. Note the reversibility of the process when CAIs were added, especially in the cause of the dopaminergic neurons.
Figure 11B:
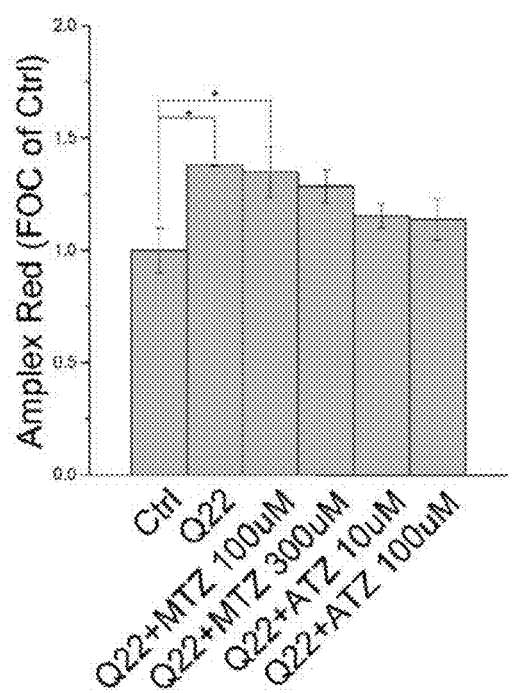
Figure 13A:
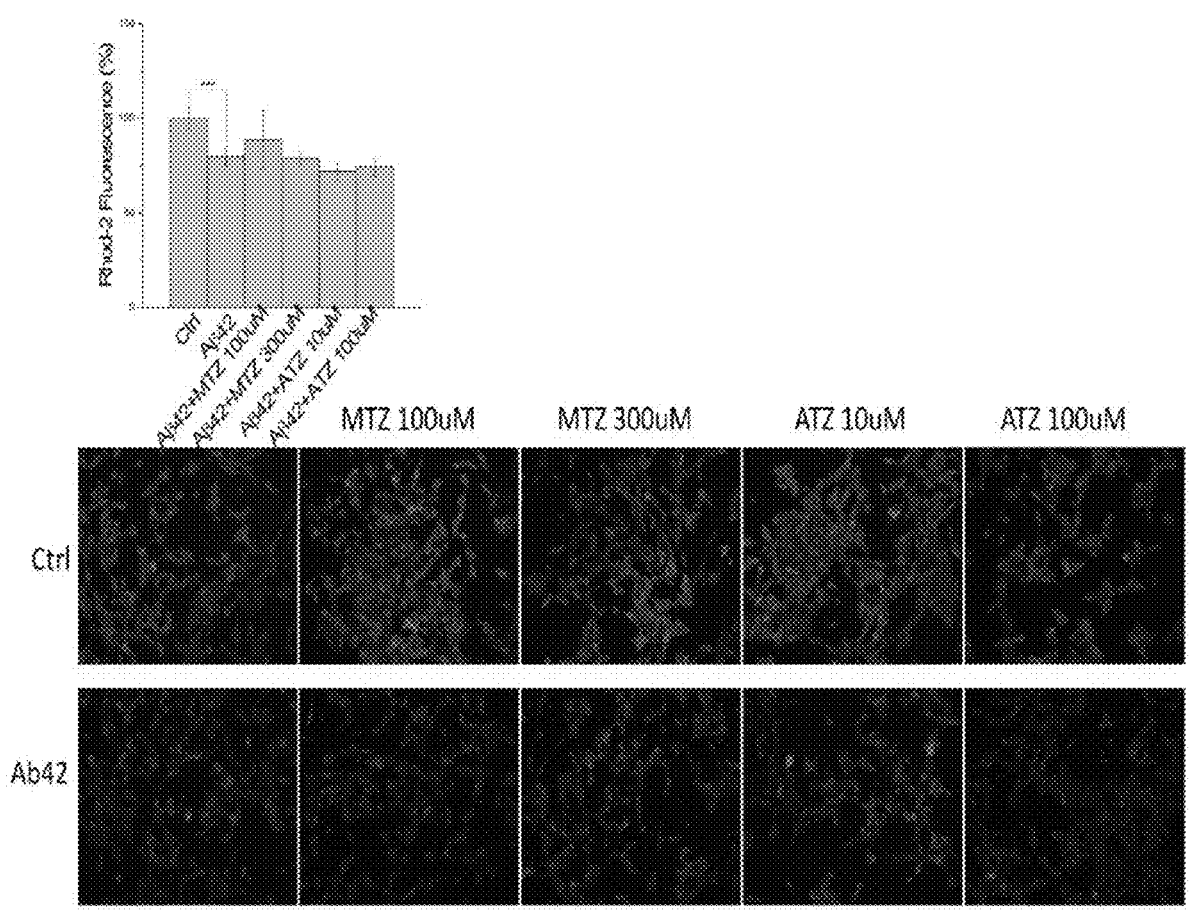
Figure 13B:
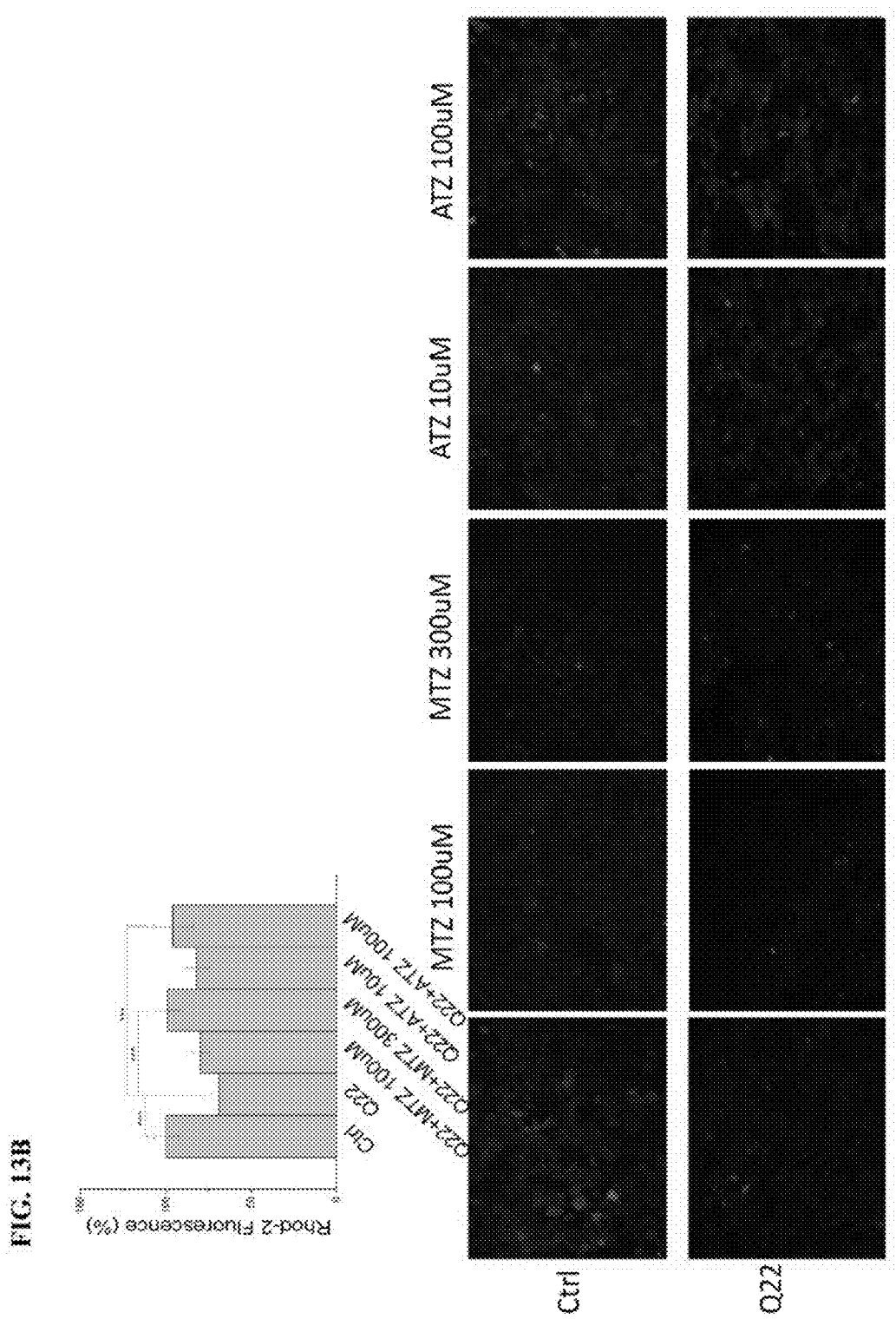
Figure 13C:
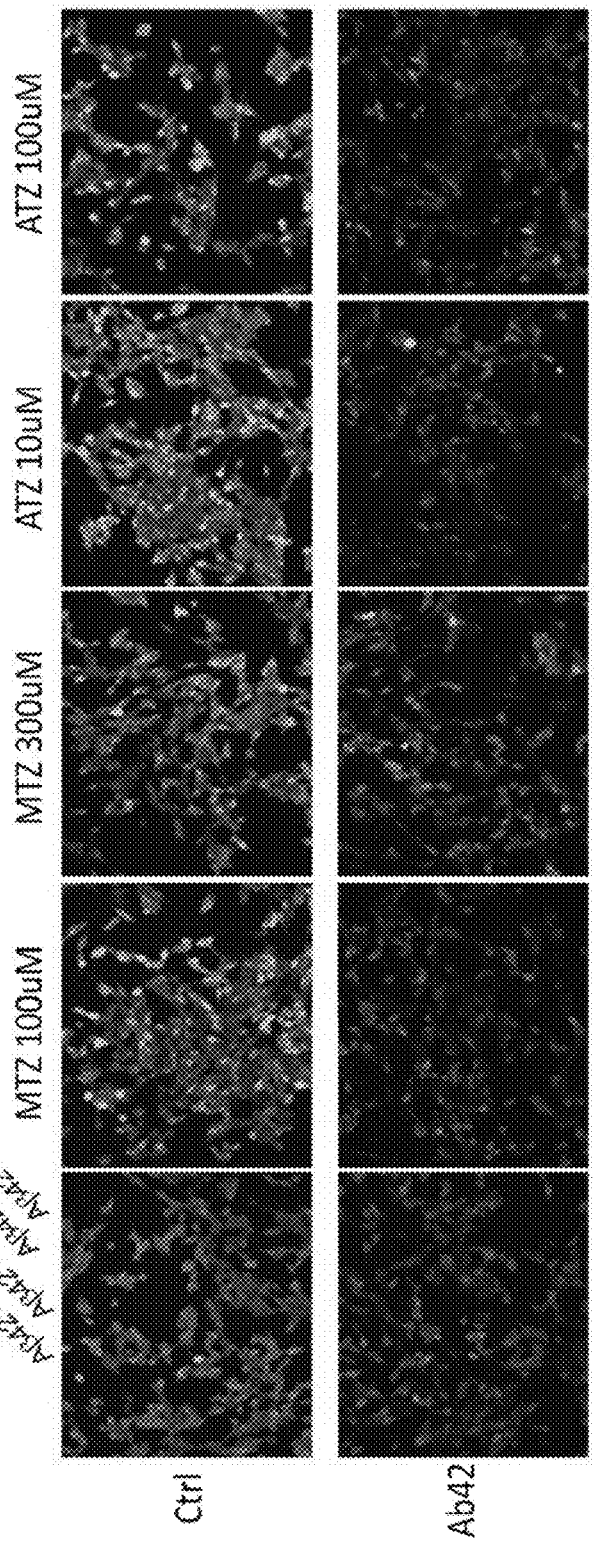
Figure 13F:
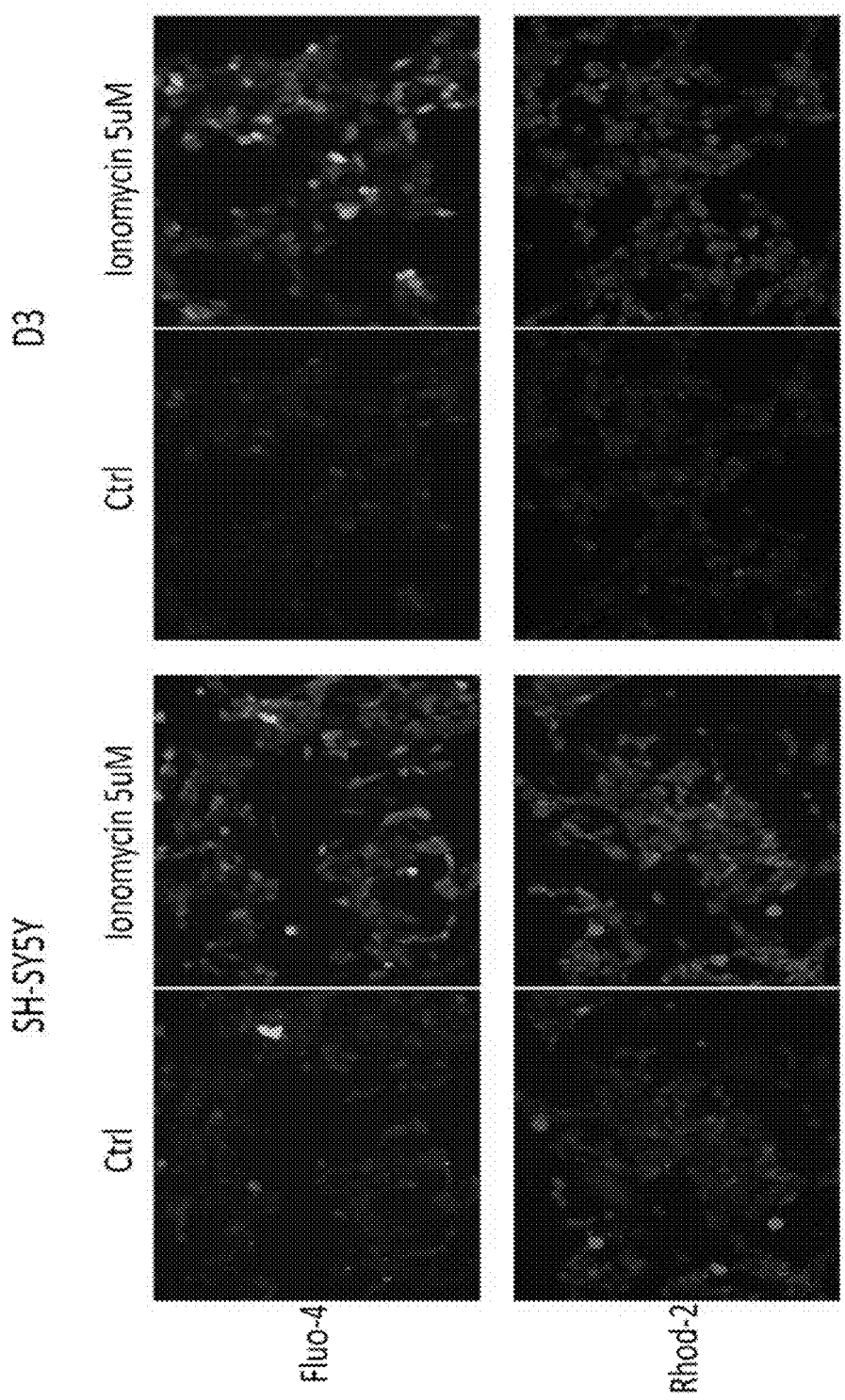
Figure 14A:
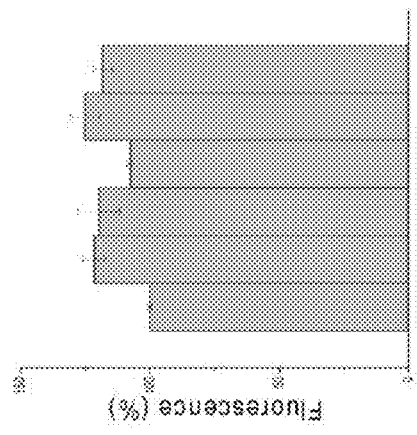
FIGS. 14A-14D. Intracellular pH is not affected neither by Aβ not by CAIs. Intracellular measurement of the pH after 3 h of treatment with the pre-aggregated peptide in (FIG. 14A) SH-SY5Y and (FIG. 14B) D3 cell cultures. Same measurement after 16 h of treatment with the Aβ with no pre-aggregation, in (FIG. 14C) SH-SY5Y and (FIG. 14D) D3 cells.
Figure 14B:
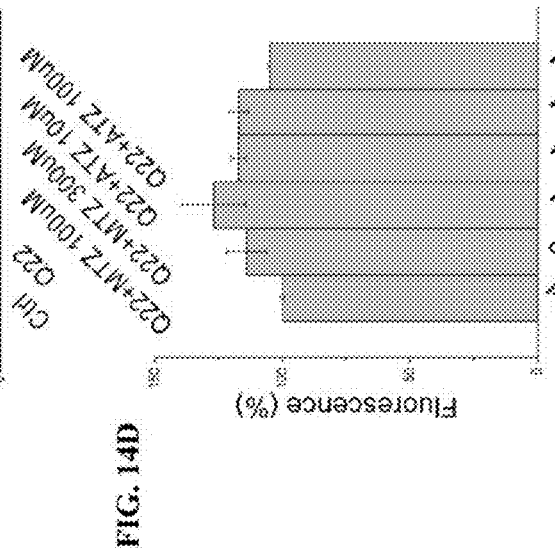
Figure 14C:
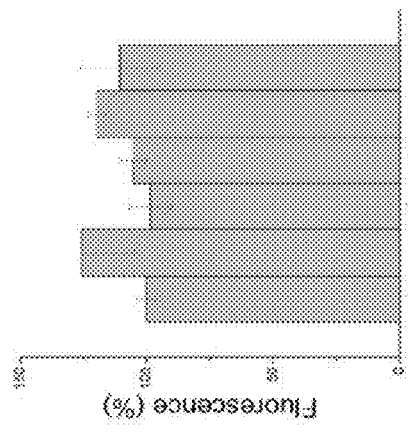
Figure 14D:
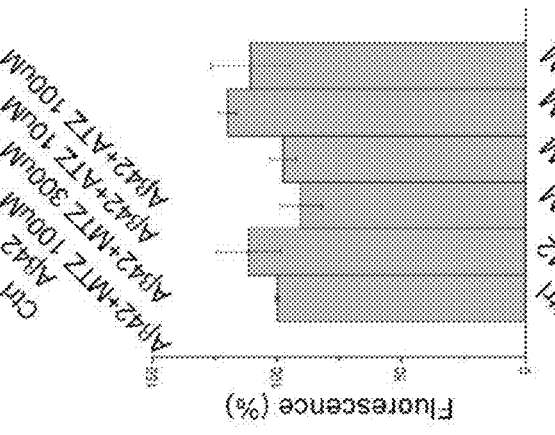

Excessive production of $H_2O_2$ by the mitochondria is a classical signal of mitochondrial dysfunction and mediator of cell death [40]. $H_2O_2$ is a membrane permeable second messenger, as well as a potent precursor of other ROS generation [41]. The levels of $H_2O_2$ produced by mitochondria isolated from neuronal and ECs were studied after cell treatment with the peptides in the presence or absence of the CAIs. It was found that Aβ induced a significant increase in the rate of generation of $H_2O_2$ (3 fold-increase in neuronal cells and about 1.5 fold-increase in ECs), measured by Amplex Red (FIG. 11A-11B). ATZ, albeit used at lower concentrations than MTZ, had a more dramatic effect on the inhibition of $H_2O_2$ production in ECs, while in neuronal cells both drugs at the proposed concentrations completely reverted the effect of Aβ. The mitochondrial calcium concentration in SH-SY5Y cells (FIG. 13A) and in D3 cells (FIG. 13B) and cytoplasmic calcium concentration in the same cell models (FIG. 13C and FIG. 13D, respectively) showed that the protective effects of MTZ and ATZ were not primarily mediated by calcium flux, as neuronal cells didn't show changes in calcium concentration in presence of Aβ or Aβ+CAIs. When the cells were pre-treated with the Aβ peptide, both mitochondrial and cytoplasmic calcium concentration remained the same compared to treating at the same time with CAIs and Aβ (FIG. 13E). Ionomycin treatment in both mitochondrial and cytoplasmic calcium concentration after the treatments showed additional protective effects (FIG. 13F).

Other Cellular ROS and Mitochondrial Calcium Homeostasis are not Affected by Amyloid-Induced Toxicity.

The cellular oxidative state and the presence of other ROS were measured by using both CellROX and DCFDA fluorescent probes. While the CellROX probe allowed measurement of the general oxidative stress within live cells, the second one is a specific indicator of the levels of hydroxyl, peroxyl and other ROS within live cells. After Aβ challenge, no significant changes in CellROX or DCFDA fluorescence were observed in the experimental model (FIG. 14A-14D). The drugs, added together with the peptides, also did not affect CellROX and DCFDA signal within cells. The length of incubation with Aβ did not affect the cellular oxidative state or presence of other ROS (compare FIGS. 14A-14B at 3 hours incubation with FIGS. 14C-14D at 16 hours incubation).

Fluctuations in mitochondrial free calcium levels are usually linked to mitochondrial dysfunction and cell death [42]. Using specific fluorescent dyes, the mitochondrial and cytoplasmic levels of free calcium were studied. It was found that both peptides decreased mitochondrial free calcium levels (FIGS. 15A-15B). Interestingly, when the same parameter was studied in cytoplasm, a similar effect to that observed in mitochondria was found (although the decrease was not significant in ECs). CAIs, given together with the peptide for 45 minutes, did not have any effect on the decrease in mitochondrial and cytoplasmic $Ca^{2+}$ in neuronal cells, while in ECs, the highest doses of MZT and AZT were able to counteract the effect exerted by the peptide, Ionomycin (5 μM) was added to the cells at the end of the experiments. Ionomycin, a well-known ionophore, which induces unspecific calcium loading independent of carriers, caused an increase in mitochondrial and cytoplasmic calcium levels in both D3 and SH-SY5Y cells, confirming that the cells, even after treatment, maintained the ability to load calcium (FIG. 13F).

To exclude any experimental factors affecting the observed fluorescence, the cells were subjected to different washing and treatment times, and a decrease in the levels of free calcium in both mitochondrial and cytoplasmic compartments after Aβ challenge was consistently observed. Pretreatment with the drugs for 3 hours before peptide addition did not produce any difference in $Ca^{2+}$ influx compared to simultaneous addition of peptides and drugs. Moreover, the drugs alone did not induce changes in the mitochondrial/cytoplasmic $Ca^{2+}$ levels.

Carbonic Anhydrase Inhibition does not Affect Intracellular pH or ATP Generation.

Carbonic anhydrase catalyzes the interconversion of $CO_2$ and $H_2O$ to $HCO^-_3$ and protons, through a reversible reaction [43]. For this reason, upon enzyme inhibition the intracellular levels of $HCO^-_3$ may vary. Because bicarbonate is one of the most important components of the pH buffering system of the human body, changes on its concentration could produce dramatic variations in the intracellular pH. In fact, one of the main consequences of the over dosage of MTZ and AZT in humans is the imbalance in the serum electrolyte levels, and the resultant change in blood pH. Small increases in the pH of the solutions where MTZ is solved are also linked to increases in its solubility [44], and may induce changes in the bioavailable concentration of MTZ, and probably of AZT, which would introduce more complexity in this study. Therefore, possible changes in the intracellular pH upon cell treatment with the CAIs were monitored.

Under the present experimental conditions, intracellular pH values, measured after adding MTZ or AZT (100 μM and 300 μM and 30 μM and 100 μM respectively) for 3 and 12 hours, in the presence and in the absence of the peptide, did not show any significant changes. Pre-aggregation of Aβ prior to cell challenge also did not have any effect on cellular pH.

In order to examine a possible effect of carbonic anhydrase inhibition on proton flux across the inner mitochondrial membrane, cellular ATP levels in permeabilized cells were measured using luciferin-luciferase (CellTiter-Glo, Promega). Dissimilar results were obtained in SH-SY5Y and D3 cells. Treatment of SH-SY5Y cells with Aβ induced a slight decrease in ATP levels (p=0.05). These levels remained unchanged upon treatment with MTZ or AZT in combination with the peptide. As a control, treatment with ATP synthase inhibitor oligomycin induced a 34% decrease (p<0.0001). In contrast, treatment of D3 cells with the Q22 peptide induced a 21.6% increase in steady state ATP levels (p=0.001). This increase was unaffected by co-treatment with either MTZ or AZT. Interestingly, oligomycin treatment also induced an increase in ATP luminescence (32.4%, p=0.0002). Despite cell type differences likely due to different coupling properties, CAIs did not induce changes in ATP production under Aβ challenge, suggesting that energy production and proton flux are not involved in the drugs' mechanism of action, which is primarily driven by the prevention of mitochondrial ΔΨ changes and by the reduction in mitochondrial $H_2O_2$ release.

Carbonic Anhydrase Inhibitors have a Protective Effect on Aβ-Induced Apoptosis in Epithelial and Neuronal Cells.

Figure 16A:
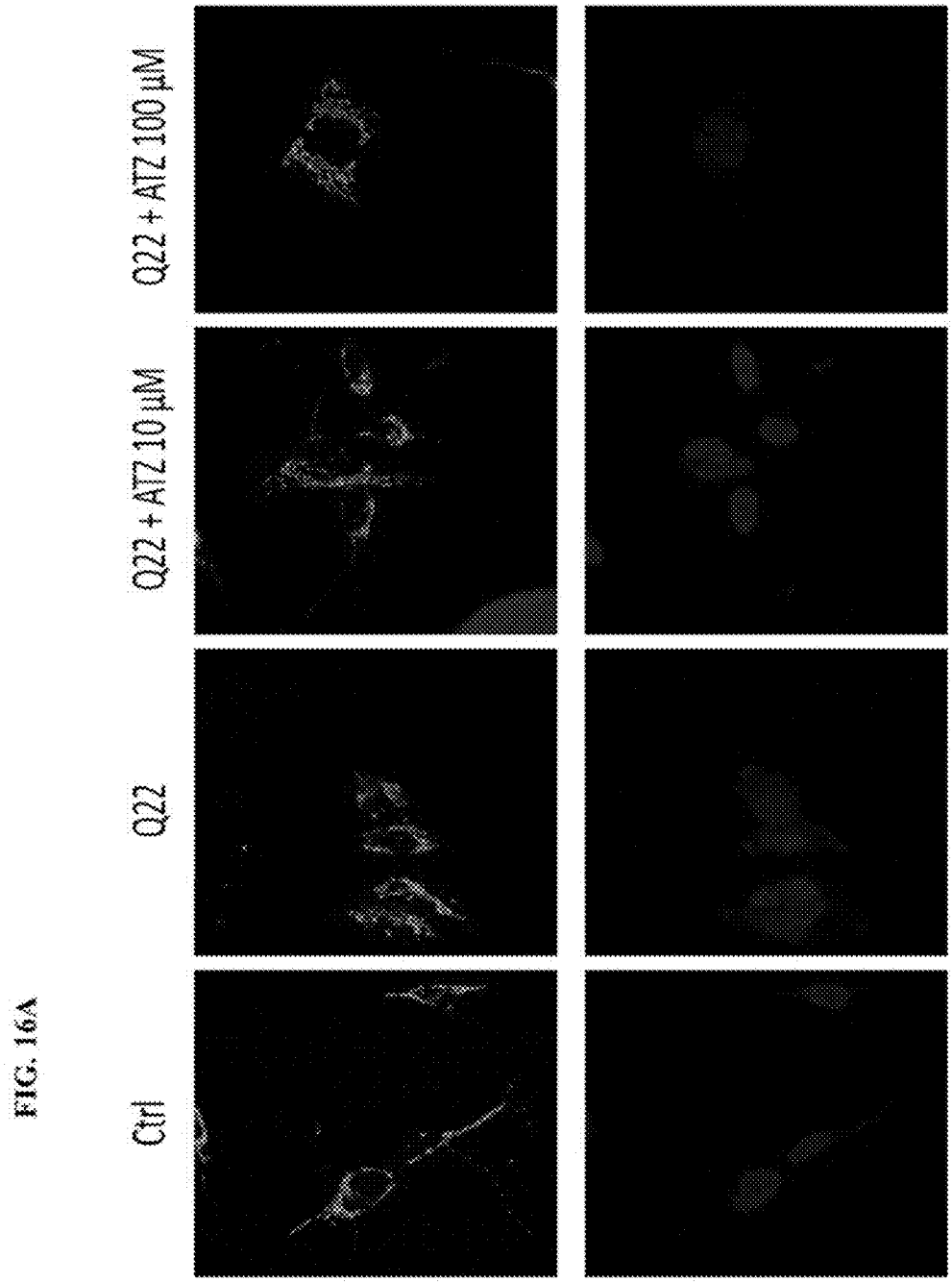
FIGS. 16A-16D. Protective effect of CAIs on Aβ-induced apoptosis. Effect of CAIs on preventing CytC release in (FIG. 16A) SH-SY5Y and (FIG. 16B) D3 cells. Protective effect of MTZ and AZT on the caspase 9 activation in (FIG. 16C) SH-SY5Y and (FIG. 16D) D3 cell cultures. In all panels, CytC release is shown as diffuse cytoplasmic green staining, compared to chain like staining of CytC in intact mitochondria of Control cells and cells treated with ATZ. Blue represents nuclei stained with Dapi. Nuclear chromatin condensation indicative of apoptosis (smaller and brighter nuclei) is also visible in cells subjected to Aβ challenge, and is prevented by ATZ. Similar effects are obtained in neuronal and glial cells.
Figure 16B:
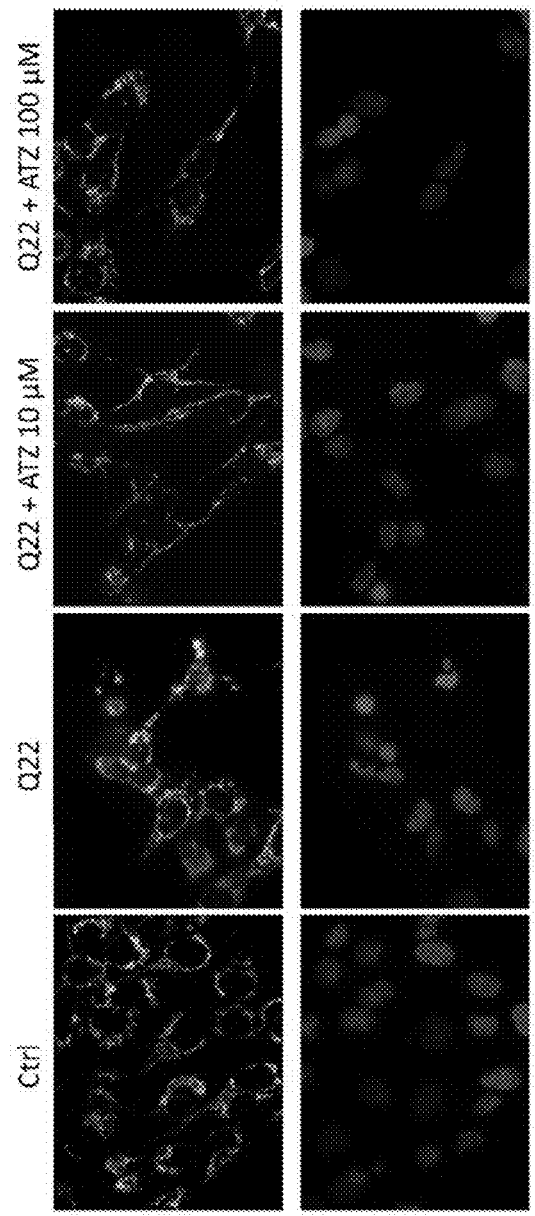
Figure 16C:
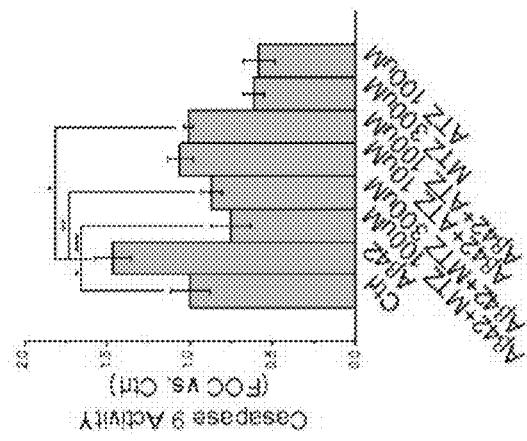
Figure 16D:
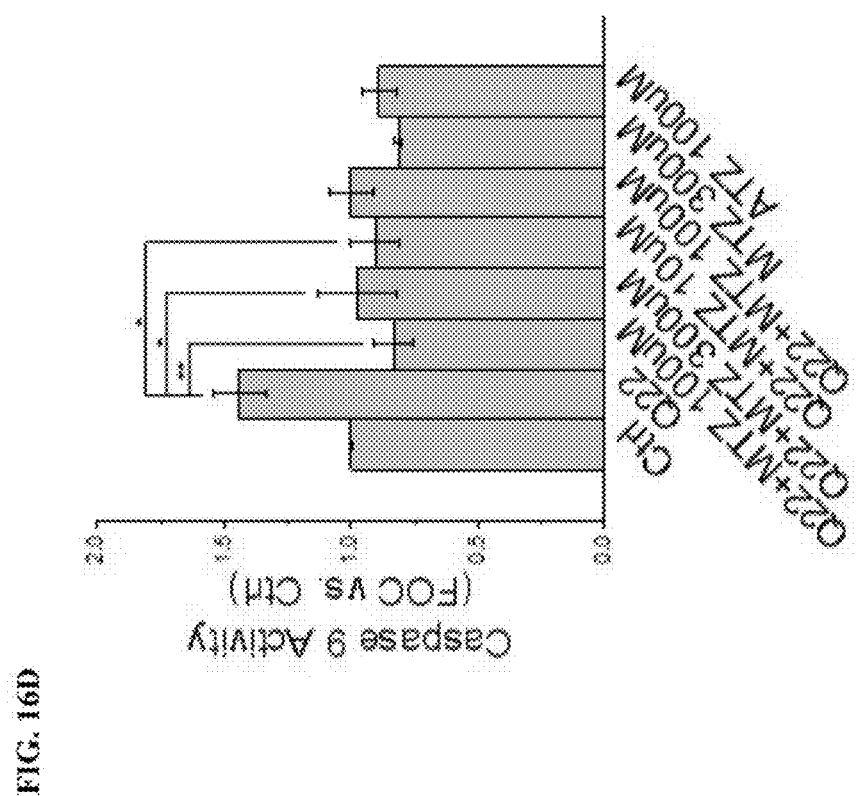

CAIs were capable of preventing CytC release in SH-SY5Y (FIG. 16A) and D3 cells (FIG. 16B). Both MTZ and ATZ showed a protective effect on the caspase 9 activation in SH-SY5Y (FIG. 16C) and D3 (FIG. 16D) cell cultures. In all panels of FIG. 16, CytC release was shown as diffuse cytoplasmic green staining, compared to chain-like staining of CytC in intact mitochondria of Control cells and cells treated with ATZ. Blue represents nuclei stained with DAPI. Nuclear chromatin condensation indicative of apoptosis (smaller and brighter nuclei) was also visible in cells subjected to Aβ challenge, and was prevented by ATZ (FIGS. 16A-16B). Similar effects are obtained in neuronal and glial cells. ATZ was effective at concentrations 10 times lower than MTZ.

Apoptotic Cell Death in Response to Aβ was Prevented by ATZ and Analog CAIs in Neuronal, Endothelial and Glial Cells.

Apoptosis in response to Aβ and its inhibition in the presence of CAIs was measured by Cell death ELISA plus (Roche) in SH-SY5Y neuronal cells (FIG. 17A), D3 endothelial cells (FIG. 17B) and glial cells (FIG. 17C). As shown in FIGS. 17A-17C, apoptosis was prevented by the CAIs methazolamide (MTZ) and acetazolamide (ATZ), showing that the CAIs inhibit endothelial, vascular and glial cell death.

Effect of ATZ and MTZ on Hippocampal Amyloid Pathology and Caspase 3 Activation in TgSwDi Mice.

Immunostaining was performed in control (Cnt) mice and TgSwDI (Swedish-Dutch-Iowa mice, a model of vascular and parenchymal amyloidosis) in the presence or absence of MTZ or ATZ (FIG. 18A). Mice were treated with the drugs incorporated in their diet starting at 5-6 months of age and sacrificed at 9 months. Aβ is stained in red, active caspase 3 in green, and nuclei are stained in blue by DAPI. Colocalization of caspase 3 and Aβ resulted in a yellow staining. The top left panel represents the control WT mouse. In the top-right panel, the hippocampus of a 9 months old TgSwDI mouse showed extensive Aβ deposition in vessels and diffused parenchimal plaques. Caspase 3 activation was evident in vessels and neuronal and glial cells presenting aβ deposition (yellow). Caspase activation was prevented by ATZ (bottom left panel). In mice treated with MTZ, a reduced deposition of Aβ can be also observed. MTZ and ATZ also had a normalizing effect on the increase of freezing shown by TgSwDI mice in contextual fear conditioning (FIG. 18B). The increase in caspase 3 activation induced by Aβ was inhibited in mice treated with MTZ and ATZ. Moreover, mice treated with MTZ in particular, showed a reduction in Aβ deposition compared to TgSwDI mice, likely due to the known increase in CBF by CAIs. A short-term treatment (3 months) with CAIs also improved freezing in fear conditioning and latency (trial 7-10 shown) in the Barnes maze (FIG. 18B-18C). These results indicate a reduction of neurotoxicity and neurodegeneration by the CAIs.

Methazolamide Prevented DNA Fragmentation and CytC Release in Neuronal, Endothelial and Glial Cells.

Figure 19A:
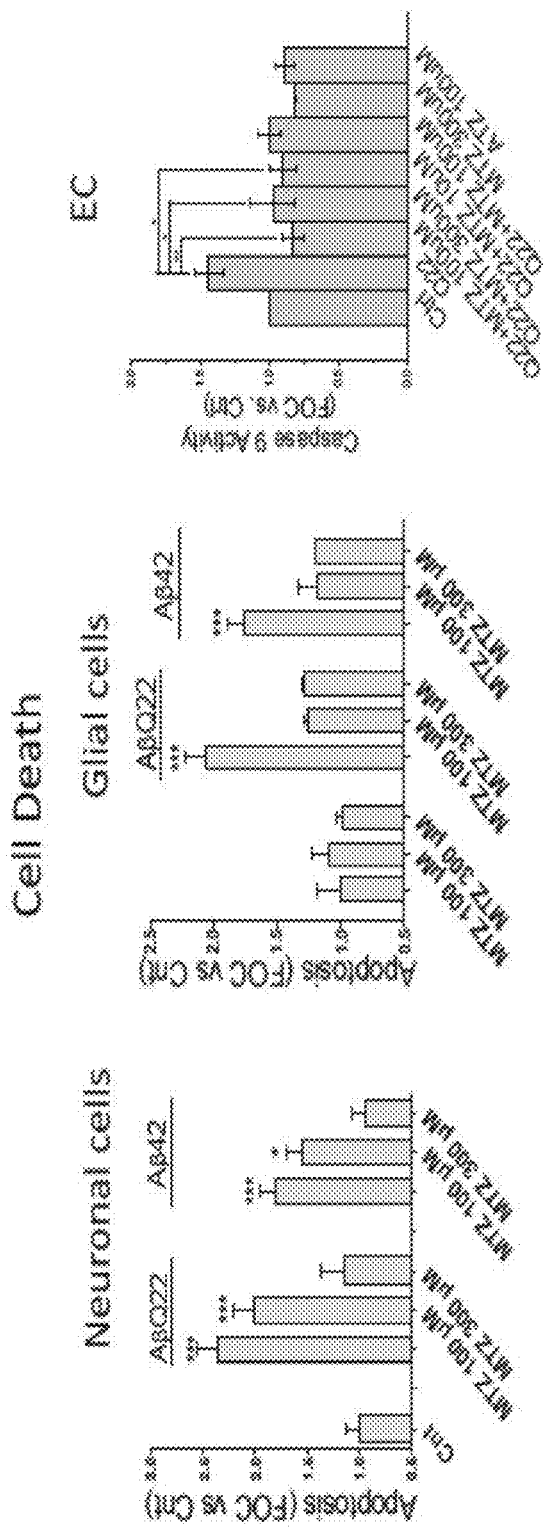
FIGS. 19A-19B. Methazolamide prevents DNA fragmentation and CytC release in neuronal, endothelial and glial cells. Neuronal, glioma cells and human cerebral microvascular EC were challenged with 50 μM Aβ40-Q22 or 10 μM Aβ42, in the presence or absence of MTZ or ATZ (FIG. 19A). Apoptosis was evaluated by Cell Death Detection ELISAplus (1 day in SHSY-5Y and EC; 3 days in glioma-Neuronal SHSY-5Y (left panel) and Glioma cells (right panel) were challenged with 10 μM Aβ42 for 24 hours) (FIG. 19B). Green fluorescence highlights CytC staining; chain-like appearance of CytC represents mitochondrial localization, whereas more diffuse green staining indicates release into the cytoplasm. Magnification 40×. Cnt=control cells in absence of peptide and MTZ.
Figure 19B:
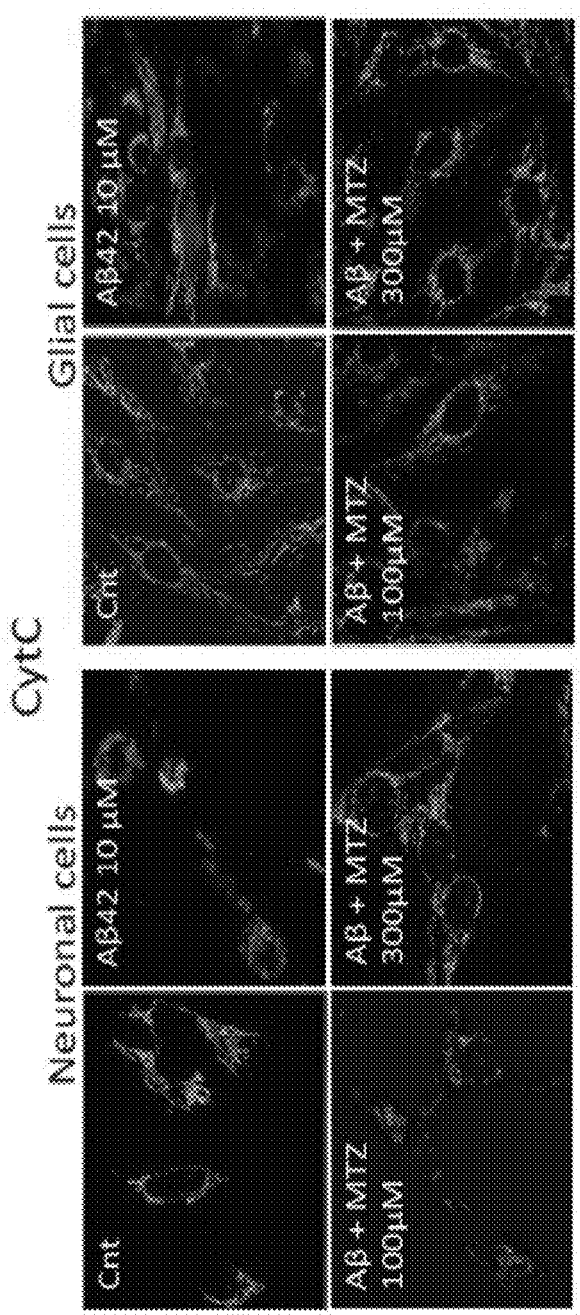

Neuronal, glioma cells and human cerebral microvascular endothelial cells (EC) were challenged with 50 µM Aβ40-Q22 or 10 µM Aβ42, in the presence or absence of MTZ or ATZ (FIG. 19A). Apoptosis was evaluated by Cell Death Detection ELISAplus (1 day in SHSY-5Y and EC; 3 days in glioma). Neuronal SHSY-5Y (left panel) and Glioma cells (right panel) were challenged with 10 µM Aβ42 for 24 hours (FIG. 19B). Green fluorescence highlighted CytC staining; chain-like appearance of CytC represents mitochondrial localization, whereas more diffuse green staining indicated release into the cytoplasm. Magnification 40×. Cnt=control cells in absence of peptide and MTZ. Therefore, MTZ prevented release of CytC and the resulting activation of apoptosis pathways, showing effective inhibition of neurovascular mitochondrial dysfunction.

Effect of CAIs on Aβ-Mediated Loss of mitochondrial Membrane Potential, Caspase Activation and $H_2O_2$ Production.

Mitochondrial membrane potential was measured by TMRM in neuronal and endothelial cells after treatment with Aβ in the presence or absence of MTZ or ATZ (FIG. 20A). Mitochondria were isolated after cell treatment with Aβ in the presence or absence of MTZ or ATZ, and mitochondrial $H_2O_2$ production was quantified using Amplex Red Hydrogen Peroxidase/Peroxidase Assay (FIG. 20B). Results are expressed as fold change in $H_2O_2$ production compared with no-peptide controls (Cnt). Caspase 9 activity in neuronal and glial cells was measured by luminescence (FIG. 20C). MTZ inhibited the activation of caspase 9 induced by incubation with 10 µM Aβ42 for 24 hours in both cell types. CAIs are shown here to inhibit release of mitochondrial ROS and the resulting caspase activation.

Apoptosis in SHS-5Y and CDE D3 Cells with and without Treatment with ATZ.

Figure 21:
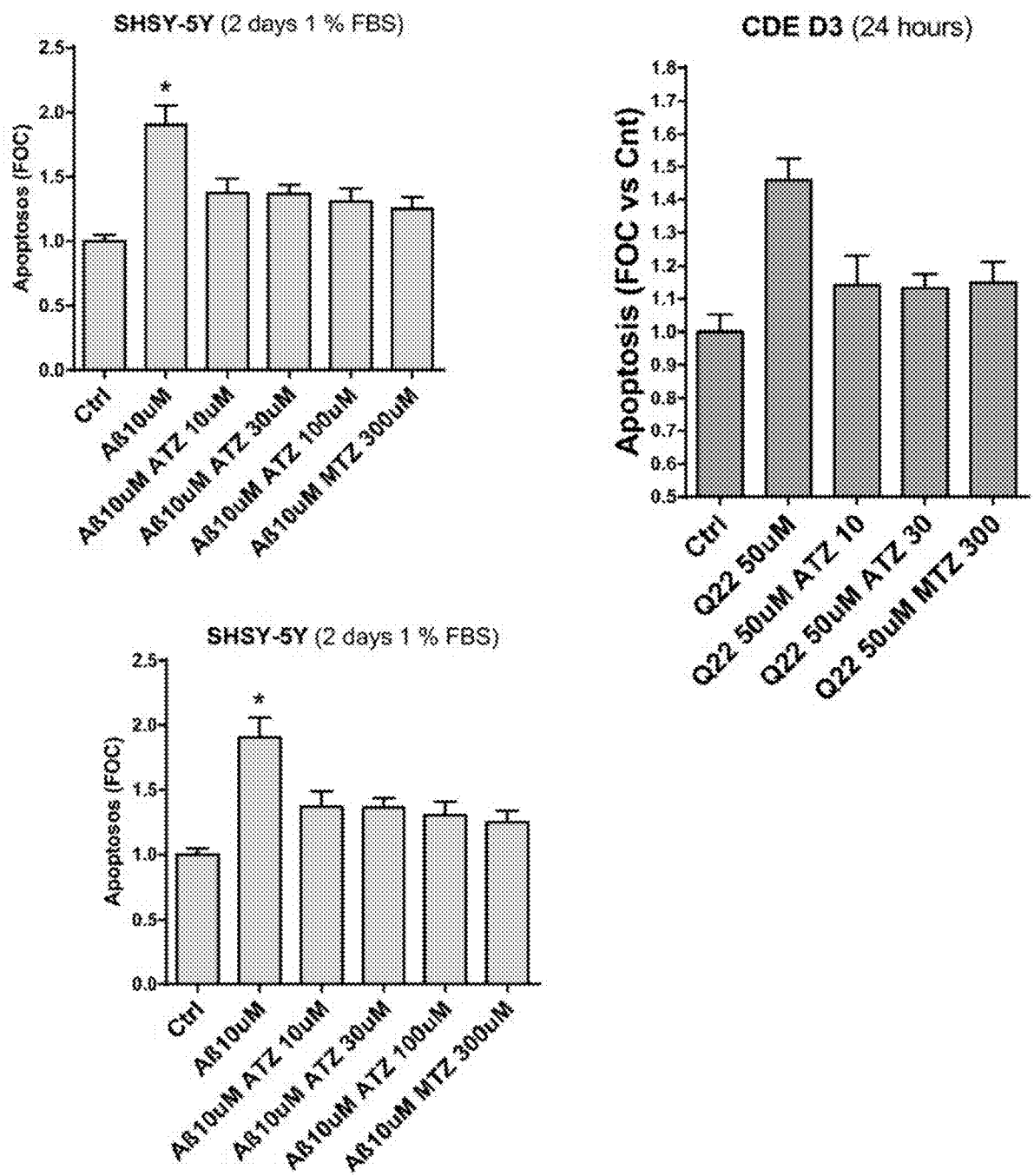
FIG. 21. Graphs showing apoptosis in SHS-5Y and CDE D3 cells with and without treatment with AZT.

CAIs inhibited apoptosis in both SH-SY5Y neuronal cells and D3 endothelial cells treated with Aβ in the presence or absence of MTZ or ATZ (FIG. 21), suggesting prevention of amyloid-mediated brain cell death.

Example 3: Inhibition of Carbonic Anhydrase Prevents Amyloid β Mitochondrial Toxicity in Neuronal and Endothelial Cells Materials and Methods Cell Cultures The dopaminergic neuroblastoma SH-SY5Y cell line was purchased from the American Type Culture Collection (ATCC, Manassas, Va., US) and grown as reported in [74]. Briefly, DMEM:DCFF12, supplemented with 20 units/mL penicillin-streptomycin and 15% (v/v) FBS, was used. Immortalized human brain microvascular endothelial cells, hCMEC/D3 cells [75] (D3), were obtained from Babette Weksler [75] and grown in complete EBM-2 medium, containing all the growth supplements (Hydrocortisone, hFGF-B, VEGF, R3-IGF-1, ascorbic acid, hEGF, GA-1000 and heparin), 20 units/mL penicillin-streptomycin and 5% FBS. Both cell lines were grown in a humidified cell culture incubator, under a 5% $CO_2$ atmosphere and at 37° C.

Drug Preparation

MTZ and AZT were both dissolved in DMSO to stock solutions of 300 mM and kept at −20° C. until the day of the experiment. The drugs were thawed at room temperature and then dissolved in the specific medium used in each experiment to the final concentrations, (100 and 300 µM in the case of MTZ and 10 to 100 µM for AZT).

Aβ Peptides

Synthetic Aβ42 was synthesized using N-tert-butyloxycarbonyl chemistry by James I. Elliott at Yale University and purified by reverse-phase high-performance liquid chromatography on a Vydac C4 column (Western Analytical, Murrierta, Calif., US) [76] Aβ40-Q22 (the Dutch genetic variant, containing the E22Q substitution) was synthesized by Peptide 2.0 Inc. (Chantilly, Va., US) and purified by HPLC/MS. Purity was >95%. Aβ homologs were dissolved to 1 mM in HFIP, incubated overnight to break down pre-existing β-sheet structures [9], and lyophilized. Peptides were subsequently dissolved in DMSO to a 10 mM concentration, followed by the addition of deionized water to 1 mM concentration and by further dilution into the medium in which the experiments were run, to a final concentration of 10 µM in the case of Aβ42 and to 50 µM in the case of the Aβ40-Q22. Peptide treatments were performed in EBM-2 supplemented with FBS 1% and in DMEM:F12 with no FBS, for the D3 and the SH-SY5Y cell lines, respectively.

Peptide Pre-Aggregation

Peptide pre-aggregation to obtain oligomeric preparations was performed following the protocol published by Dahlgren et al., [77]. Briefly, lyophilized peptides were resuspended in DMSO to a 5 mM concentration, immediately prior to use. After that, diluted peptides were dissolved in F12 medium with no phenol red or FBS to a final concentration of 100 µM and they were incubated at 4° C. for 24 h, in order to allow the formation of the oligomers. 24 h later, the oligomers were added to the cultures, at the desired concentrations, alone or in co-treatment with the different drugs.

Cell Death ELISA

The extent of apoptosis caused by Aβ in the presence or absence of MTZ was assessed by quantitation of nucleosome formation using Cell Death ELISA$^{plus}$ (Roche Applied Science, Indianapolis, Ind.). Briefly, after incubation with the peptides, plates were centrifuged in a Beckman J-6B centrifuge (10 min; 1,000 rpm), cells lysed, and DNA-histone complexes (nucleosomes) quantitated by Cell Death ELISA, as previously described (Fossati et al., 2010).

Thioflavin T Binding Assay

Binding of the different Aβ peptides to Thioflavin-T was monitored by fluorescence evaluation, as described (Fossati et al., 2010; Walsh et al., 1999). Briefly, after peptide aggregation at 50 µM concentration in culture media in the presence or absence of MTZ, 6 µl aliquots from each of the time-points were added to 184 µl of 50 mM Tris-HCl buffer, pH 8.5, and 10 µl of 0.1 mM Thioflavin-T (Sigma). Fluorescence was recorded for 300 s in a LS-50B luminescence spectrometer (Perkin Elmer, Waltham, Mass.) with excitation and emission wavelengths of 435 and 490 nm (slit width 10 nm), respectively, as described (Solito et al., 2009; Viana et al., 2009).

Immunocytochemical Evaluation of Cytochrome C Release

Both SH-SY5Y cells and Glioma cells were plated on glass chamber slides (Thermo Fisher Scientific, Rochester, N.Y.). Slides were pre-coated with poly-D-lysine for SH-SY5Y cells. After seeding, cells were allowed to attach for 1 day prior to treatment with Aβ in the presence or absence of MTZ for 24 hours. Cells were then washed with PBS, fixed with 4% paraformaldehyde (10 min, RT) and blocked for 1 hour with 20 mg/ml BSA in PBS containing 0.3% Triton X-100 (PBST). Slides were further incubated with mouse monoclonal anti-CytC antibody (BD Biosciences; 1:200 in PBST containing 5 mg/ml BSA; 2 h, RT) followed by Alexa Fluor 488-conjugated anti-mouse IgG (Life Technologies, Grand Island, N.Y.) 1:200 in PBST with 5 mg/ml BSA for 1 h at RT, as previously described (Fossati et al., 2013). Fluorescence signals were visualized in a Zeiss LSM 510 laser scanning confocal/Confocor2 microscope using a 40×DIC oil immersion objective and LSM 510 software; acquired images were imported into ImageJ (National Institute of Health; http://rsbweb.nih.gov/ij/).

ELISA and Western Blot Assessment of CytC in Mitochondrial and Cytoplasmic Subcellular Fractions Subcellular distribution of CytC in amyloid-challenged SH-SY5Y and glioma cells was determined in mitochondrial and cytoplasmic protein extracts prepared using Mitochondria Isolation Kit (MITOISO2, Sigma) following the manufacturer's specifications. Briefly, after amyloid challenge in the presence and absence of Methazolamide, as above, cells were collected by trypsinization, resuspended in 10 mM HEPES, pH 7.5, containing 200 mM mannitol, 70 mM sucrose, 1 mM EGTA added of Protease Inhibitor Cocktail, and homogenized with the aid of a Dounce glass homogenizer. Cell homogenates were centrifuged to remove unbroken cells and nuclei (600×g, 5 min, 4° C.) and supernatants further centrifuged at 11,000×g (5 min, 4° C.) to subfractionate mitochondria. Supernatants, representing the cytosolic fractions as well as mitochondrial fractions were analyzed by CytC ELISA and WB.

Solid Phase ELISA

The concentration of CytC in cytosolic and mitochondrial fractions was quantitated by solid phase sandwich ELISA (Quantikine ELISA, human Cytochrome C Immunoassay, R&D Systems) as described by the manufacturer. Prior to the assay, fractions containing cytoplasmic proteins were concentrated on Vivaspin 500 centrifugal concentrators (GE HealthCare, molecular weight cut off 5000), mitochondrial pellets were resuspended in Cell Lysis Buffer provided with the kit, and total protein of the respective fractions was evaluated by BCA protein assay (Thermo Fisher Scientific/Pierce). Samples and human CytC standards were diluted in Calibrator Diluent and incubated with microtiter wells pre-coated with a monoclonal antibody specific for human CytC. After washing away unbound proteins, wells were further incubated with an HRP-linked monoclonal antibody anti-human CytC, color developed with tetramethylbenzinine peroxidase substrate, and evaluated through quantitation of the Absorbance at 450 nm. The CytC concentration of the different samples was interpolated from the standard curve with the aid of GraphPad Prism and normalized to the protein content of the respective subcellular fractions.

Cell Death ELISA Assay 20,000 cells per well were plated on 24-wells plates. The day after, cells were treated with peptides and/or drugs, following the experimental conditions. After that, the extent of apoptosis caused by the different peptides, as well as the hypothetic protective effect of the drugs, was assessed by quantifying the formation of nucleosomes, by using the Cell Death ELISA plus kit, following the manufacturer instructions.

Caspase 9 and Caspase 3/7 Activity Assay

Caspase 9 and caspase 3/7 activation was measured by luminescent assays (Caspase-Glo 9 and caspase-Glo 3/7, Promega, Madison, Wis.), in cells treated with the Aβ peptides in DMEM without FBS. Briefly, 10,000 cells/well were plated in 96 wells plates and incubated for 24 hours with the freshly solubilized Aβ peptides. Caspase-Glo reagent was added to the cell cultures resulting in cell lysis, followed by caspase cleavage of the substrate and generation of a luminescent signal produced by the luciferase reaction. After 40 minutes incubation, the amount of caspase activity was evaluated in a plate-reading luminometer (Synergy HT Multi-Mode Microplate Reader, Biotek, Winooski, Vt.) as described in (Fossati et al., 2012b). To inhibit non-specific background activity, the proteasome inhibitor MG-132 was added to the Caspase-Glo reagent before the experiment as indicated by the manufacturer. In all cases results are expressed as fold-change compared to untreated control cells.

Immunohistochemistry

The animals were sacrificed by trans-cardiac perfusion (medium flow pump, Fisher Scientific 13-876-2, 10 ml/min flow rate) with PBS for 2 minutes followed by 4% paraphormaldehyde for 5 minutes. Brains were then removed from the skull and postfixed in 4% paraformaldehyde for 2 h at 4° C. Cryoprotection was achieved with a solution of sucrose 15% for a day, later changed to a solution of sucrose 30% for 2 days. Brains were then washed in PBS, assembled in a plastic mold with Tissue-Tek O.C.T. compound (Fisher Scientific), and frozen with a mixture of liquid nitrogen and isopenthanol. Serial cryostat sections of 8 µm thickness were collected on positively charged microscope slides (Fisher Scientific) and stored at −80° C. until further immunohistochemical analysis.

For immunohistochemical staining, slices were warmed to RT for 5' prior to use, rinsed in PBS and blocked with Mouse on Mouse (MOM) blocking reagent (2 drops in 2.5 ml of PBS, Vector Laboratories, Burlingame, Calif.) for 20 minutes. Incubation with the rabbit monoclonal antibody against active caspase-3 (Cell Signaling Technology) was performed overnight at 4° C. in PBS containing 0.1% triton X-100 and 5 mg/ml BSA. The day after, the sections were washed three times with PBS and incubated in Alexa Fluor 488- or 633-conjugated anti-rabbit IgG (Life Technologies; 1:200 in PBST with 5 mg/ml BSA; 1 h at RT), followed by primary anti-Aβ 6E10 (1:200 in PBS+MOM for 2 hours at RT), and by secondary Alexa Fluor 568 anti-mouse IgG. Finally, the slices were washed and the DNA counterstained with TO-PRO (Life Technologies) 1:1000 for 10 min, or with NeuN green neuronal staining (1:100 in PBS for 1 hour, Millipore, Temecula, Calif.). For staining of active microglial cells, tissue sections were incubated with anti IBA1 goat antibody (Abcam, Cambridge, Mass.) 1:200 in PBS containing 0.1% Triton and 5 mg/ml BSA for 1 hour, followed by Alexa Fluor 488 anti-goat IgG (1 hour). For astrocytes, brain slices were stained with GFAP antibody (Fisher Scientific 1:200).

Total fibrillar Aβ burden (parenchymal and vascular) and CAA burden (Aβ burden in the vasculature) were evaluated separately in sections stained with Thioflavin-S, using methods described previously (Scholtzova et al., J Neurosci 2009, 29: 1846-1854).

After washing, slides were mounted with an aqueous mounting medium (Vector Laboratories). Images were acquired in a Zeiss LSM 510 confocal microscope using 40× or 100× oil lens and processed using Image J and Adobe Photoshop. Images were acquired maintaining constant exposure for all samples across single experiments. For quantifications, stained brain slices corresponding to the injection site area of 3 or more animals were quantified with Image J. The total area of NeuN, caspase 3, Aβ and IBA1 positive cells was quantified and compared between different treatments.

Statistical Analysis

ANOVA with Tukey post hoc tests for comparison of multiple groups and unpaired t test for comparison of 2 groups were performed using GraphPad Prism (GraphPad, La Jolla, Calif.). Values of P≤0.05 were considered significant.

Immunocytochemical Evaluation of Mitochondrial CytC Release

Both EC and SH-SY5Y cells were plated on to glass chamber slides (Thermo Fisher Scientific), pre-coated with either collagen-I or poly-d-lysine (for ECs and SH-SY5Y cells respectively). After seeding, cells were allowed to attach for 1 day before treatment with the different peptides for 1-3 days, as above. Cells were washed with ice-cold PBS, fixed with 4% paraformaldehyde (10 min at room temperature) and blocked for 1 h with 20 mg/ml BSA in PBST (PBS containing 0.3% Triton X-100). Slides were further incubated with mouse anti-CytC monoclonal antibody (BD Biosciences; 1:200 dilution in PBST containing 5 mg/ml BSA; 2 h at room temperature) followed by Alexa Fluor® 488-conjugated anti-(mouse IgG) antibody (Invitrogen; 1:200 in PBST with 5 mg/ml BSA; 1 h at room temperature). Fluorescence signals were visualized in a Nikon Eclipse E 800 deconvolution microscope using NIS Elements software (Nikon Instruments) for image acquisition and processing, and AutoQuant (Media Cybernetics) for 3D deconvolution.

Inhibition of CytC Release by Methazolamide

The effect of methazolamide in preventing the Aβ-induced release of CytC from the mitochondria into the cytoplasm was evaluated in EC and SH-SY5Y cultures. After peptide incubation in the presence and absence of methazolamide (Sigma), release of CytC was visualized by immunofluorescence microscopy and WB analysis, and corroborated by confocal assessment of CytC in conjunction with the mitochondrial marker MitoTracker®.

Body Weight Analysis

Figure 25A:
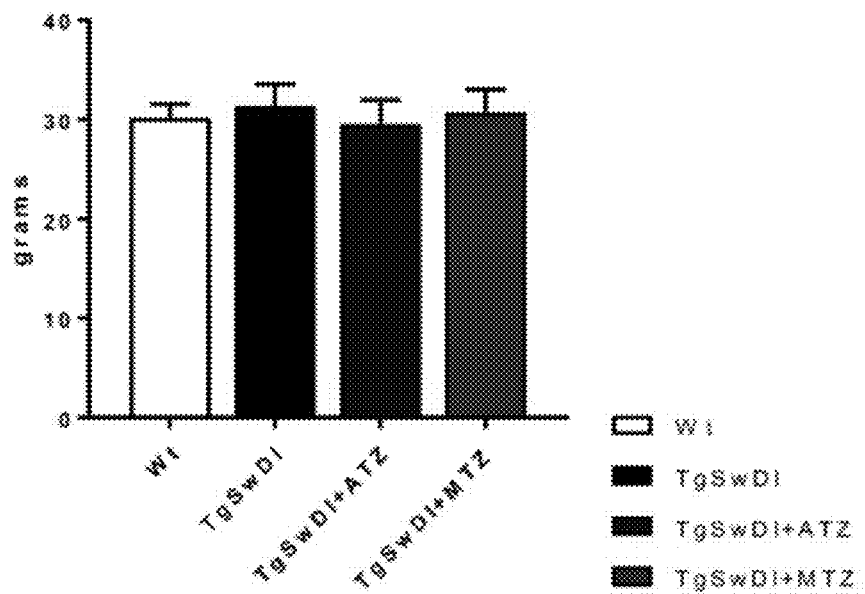
FIGS. 25A-25E. Behavioral testing of TgSwDI Mice treated with MTZ and ATZ for 8 months and tested at 15 months. Mice were treated with the drugs incorporated in their diet (at 100 ppm by TestDiets) starting at 6-7 months of age and tested at 15 months. Both MTZ and ATZ were given at 15-20 mg/kg/day (incorporated in the diet). There were no significant differences in body weight between WT and TgSwDI mice, or between TgSwDI and TgSwDI treated with the CAIs for 8 months (mice were tested at 15 months), suggesting that the drugs are well tolerated and do not cause weight loss (FIG. 25A). There were no weight differences in either females or males when groups are separated by gender (FIG. 25B). There were no differences in the death rates (between 2 months and 16 months) in TgSwDI mice and TgSwDI animals treated with the CAIs for the last 8 months, suggesting that the drugs are not toxic and can be tolerated for long term treatment (FIG. 25C). WT mice have lower death rates than TgSwDI mice. There were no significant differences in forelimbs grip strength (FIG. 25D) or all limbs grip strength (FIG. 25E) between 15-16 months-old TgSwDI mice and age-matched TgSwDI treated with the CAIs for 8 months. WT mice consistently had more strength than TgSwDI mice. There were no strength differences in either females or males when groups are separated by gender (not shown).
Figure 25B:
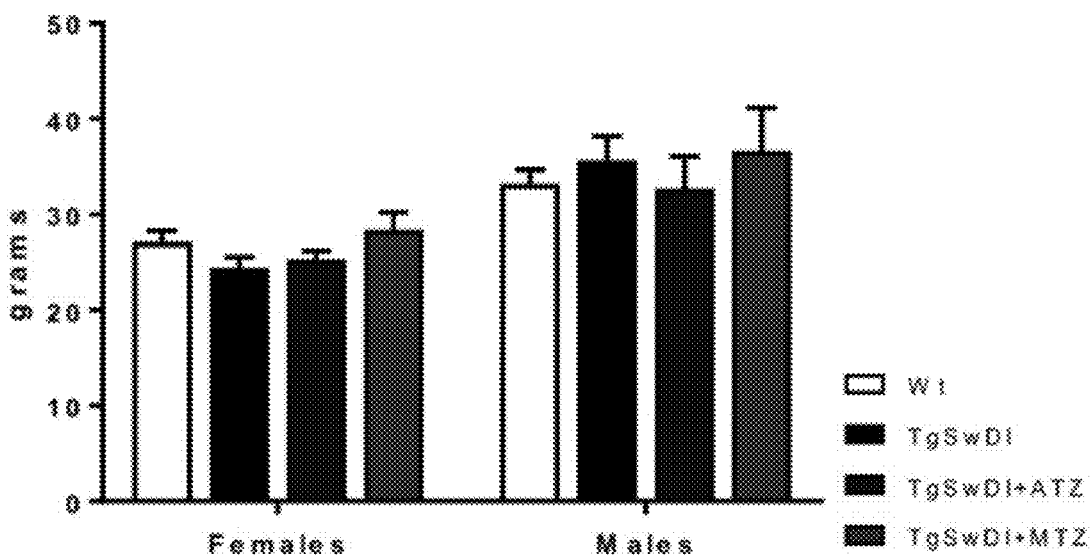

Mice were weighted before initiation of the MTZ and ATZ diet regiments and bi-weekly after. At the end of the 8 months of treatment, the 15 months-old mice were weighted before behavioral analysis. Graph shows weights at the end of the experiment. No differences in weight in the different treatment groups were observed (FIG. 25B).

Death Rate Analysis

Figure 25C:
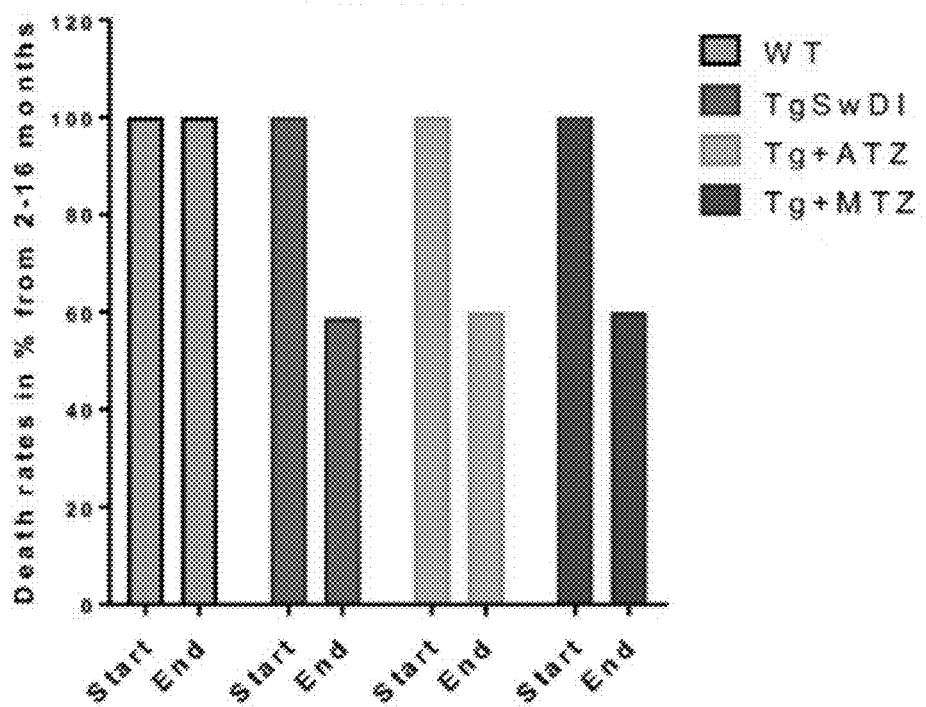

Mice in each treatment group (WT, Tg, Tg+MTZ, Tg+ATZ) were counted before the beginning of the treatment, at month 2, and at sacrifice (month 16). The number of mice left at sacrifice, compared to the initial number, is expressed in percentage (FIG. 25C).

Grip Strength Measurement and Barnes Spatial Memory Testing were Performed as Described in Example 2, Above.

Results

Cytochrome C Release, Caspase 9 and Caspase 3 Activation are Prevented by CAIs.

Figure 22A:
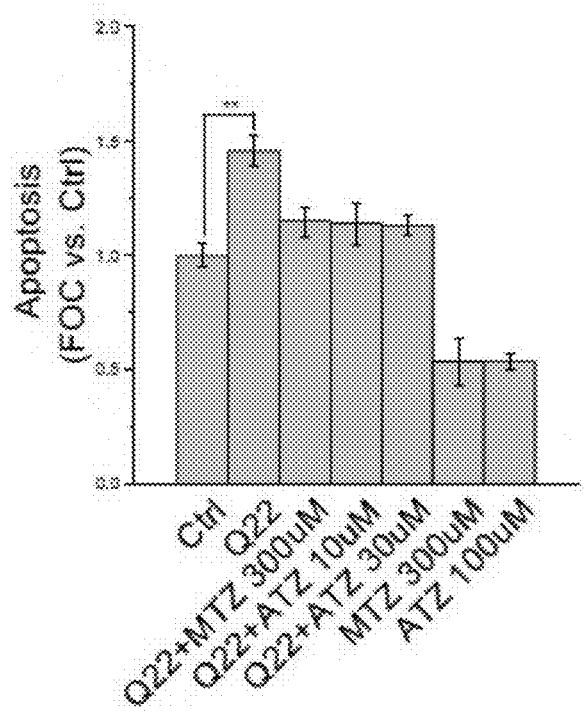
FIGS. 22A-22B. CAIs reduce cerebral microvascular endothelial cell (EC) and neuronal cell (NC) caspase activation and cell death. CAIs prevented the increase in caspase 9 activation and the induction of apoptotic cell death by amyloid peptides in endothelial and neuronal cells. The vasculotropic Aβ Q22 mutant was used to challenge cerebral microvascular endothelial cells, and the prevalently parenchymal Aβ42 was used to challenge neuronal SHSY-5Y cells. Apoptosis in neuronal SHSY-5Y cells (FIG. 22A) and cerebral microvascular endothelial cells (FIG. 22B) was determined by detecting the presence of fragmented nucleosomes by Cell Death Detection ELISA$^{plus}$ is after 1 day in the presence of peptides in D3 cerebral microvascular endothelial cells (FIG. 22B) and SHSY-5Y cells (FIG. 22A). Results are expressed as fold change compared with no-peptide controls (Cnt). Data are representative of at least three independent experiments performed in duplicate. Bars represent means+/−S.D. *P<0.05, P<0.001, *P<0.0001 compared to Cnt cells in absence of peptides and MTZ or ATZ.
Figure 22B:
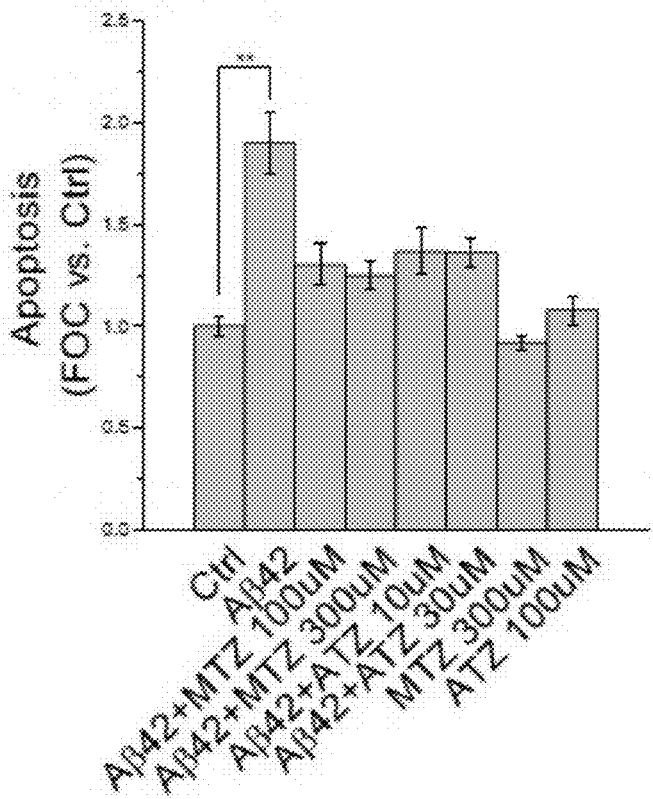

The data presented herein show that CAIs prevented the increase in caspase 9 activation and the induction of apoptotic cell death by amyloid peptides in endothelial (EC) and neuronal cells (NC). The vasculotropic Aβ Q22 mutant was used for vascular cells, and the prevalently parenchymal Aβ42 was used to challenge neuronal cells. Apoptosis in neuronal SHSY-5Y cells (FIG. 22A) and cerebral microvascular endothelial cells (FIG. 22B) was measured as described herein.

Figure 23A:
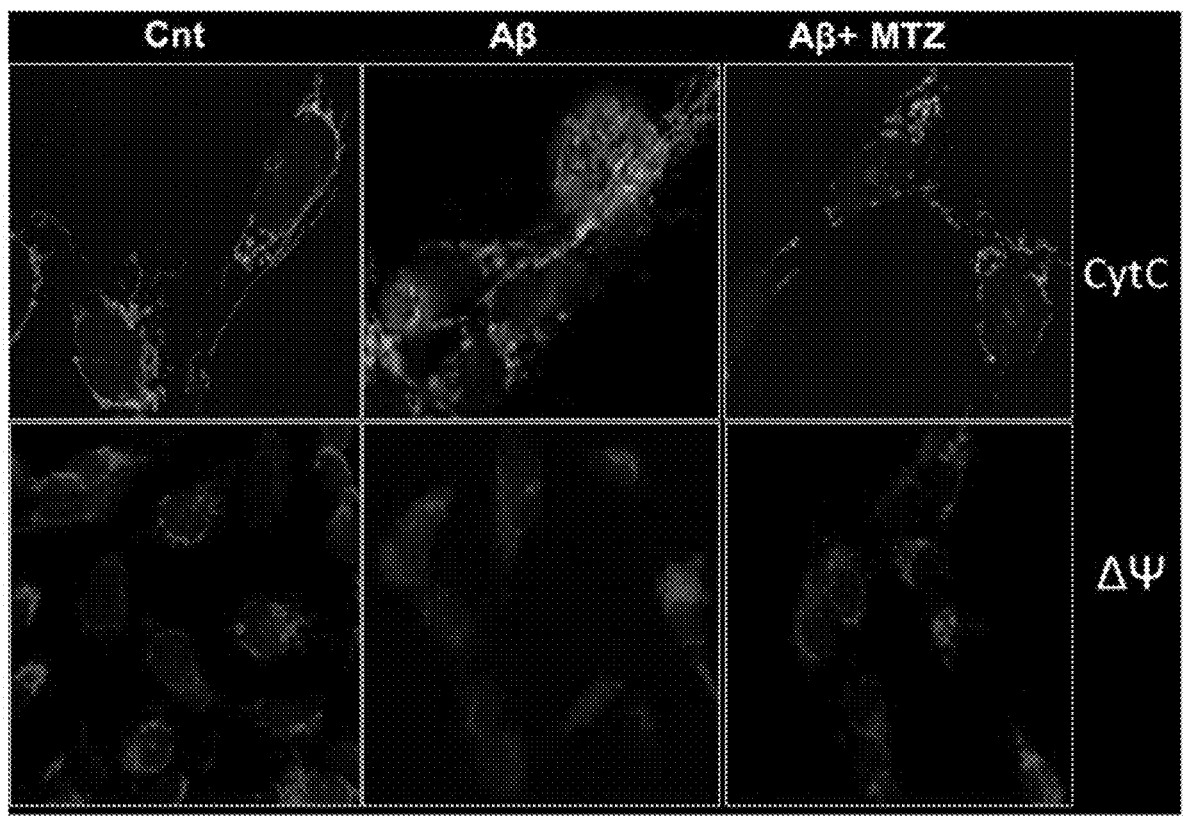
FIGS. 23A-23B. CAIs inhibit Aβ-induced Cytochrome C (CytC) release and loss of mitochondrial potential. Shown are the results of immunocytochemistry experiments. Microvascular ECs (as well as NCs and glial cells) were challenged for 24 h with 25 μM Aβ40-Q22 mutant (Q22) or 10 μM Aβ40/42 wild-type (WT). CytC was stained in green, and nuclei were stained in blue with DAPI (FIG. 23A). CytC was released from the mitochondria (chain-like structures), in cells treated with Aβ. This CytC release was shown by diffuse staining in cells treated with Aβ. In contrast, CytC was retained in the mitochondria in cells treated with Aβ+MTZ. The same was found for ATZ (not shown). Loss of mitochondrial membrane potential in cells treated with Aβ results in lack of mitochondrial internalization of the red dye and was prevented by MTZ and ATZ. Release of CytC, quantified by determining the % of cells with diffuse green staining, was prevented by MTZ (M) (FIG. 23B).

Aβ-induced CytC release was prevented by CAIs. Cytochrome C release and loss of mitochondrial potential were inhibited by CAIs as shown by immunocytochemistry experiments. Microvascular ECs (as well as NCs and glial cells) were challenged for 24 h with Aβ40-Q22 mutant (Q22) 25 µM or Aβ40/42 WT 10 µM. In FIG. 23A, Cytochrome C was stained in green, and nuclei were stained in blue with DAPI. CytC was released from the mitochondria (chain-like structures), triggering apoptosis, in cells treated with Aβ. This CytC release was shown by diffuse staining in cells treated with Aβ. In contrast, CytC was retained in the mitochondria in cells treated with Aβ+MTZ. The same was found for ATZ.

Figure 23B:
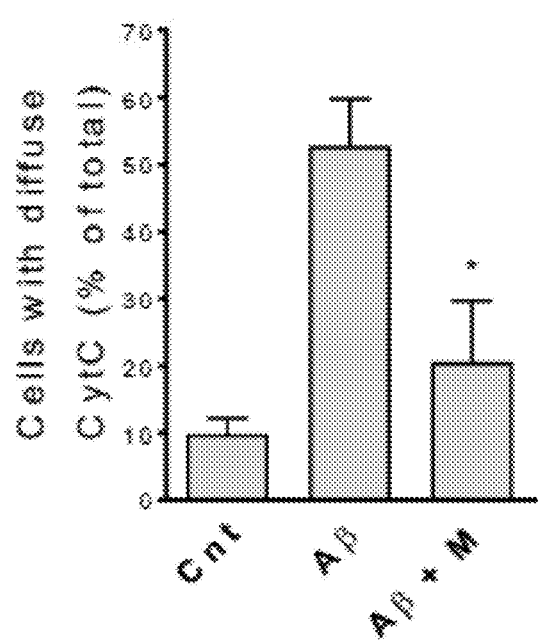

Loss of mitochondrial membrane potential was depicted in red in cells treated with Aβ (lack of mitochondrial internalization of the red dye which is dependent on membrane potential), and is prevented by MTZ and ATZ. See methods in Fossati et al., 2013. FIG. 23B shows that the release of CytC, quantified as number of cells with diffuse green staining, was prevented by MTZ (M). The number of cells with diffused CytC was counted and reported as % of total cells.

Methazolamide Prevents Caspase 3 Activation in Hippocampal Neurons.

Figure 24:
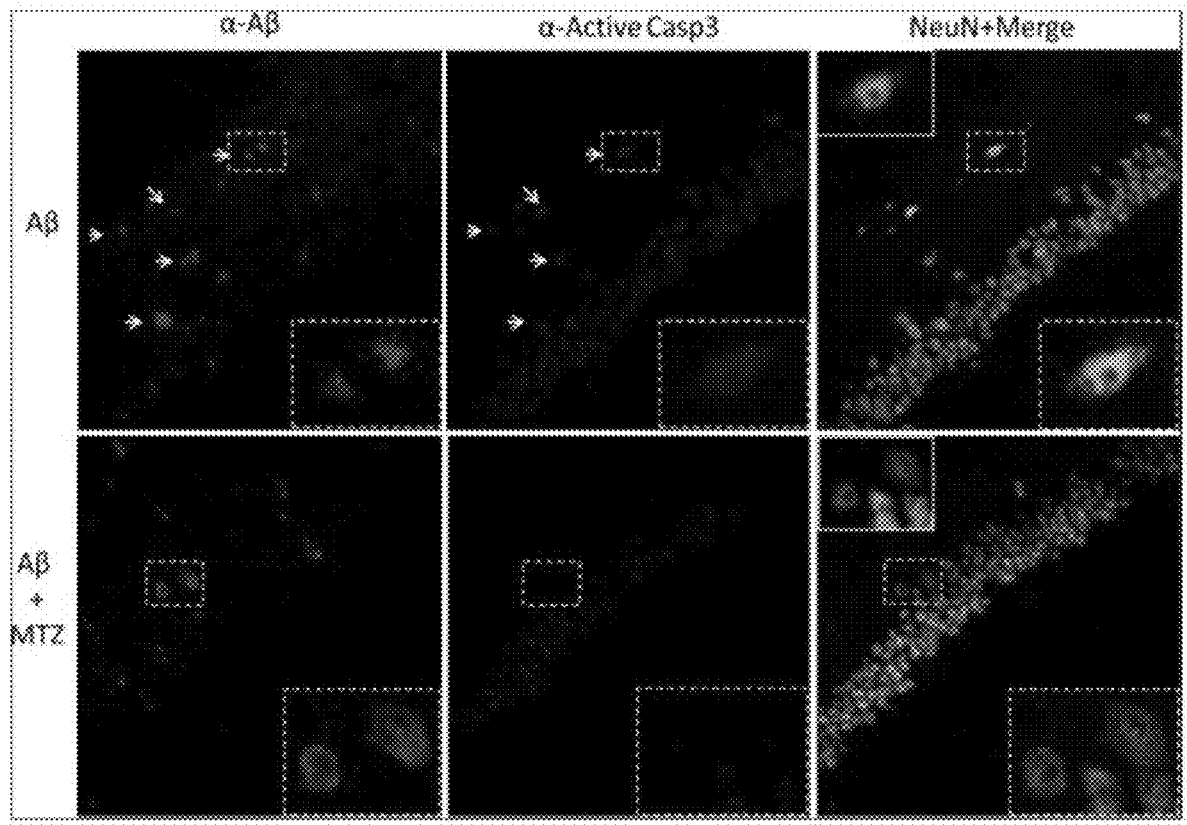
FIG. 24. MTZ prevents caspase 3 activation in hippocampal neurons. Cells with internalized Aβ (red) presented active caspase 3 (blue), in mice injected with Aβ only, while cells containing Aβ did not show activated caspase 3 in the mice injected with MTZ (intraperitoneal) 1 hour before cerebral Aβ injection. Green cells stained with NeuN represent neurons.

As shown in FIG. 24, cells with internalized Aβ (red) presented active caspase 3 (blue), in mice injected with Aβ only, while cells containing Aβ did not show activated caspase 3 in the mice injected with MTZ (intraperitoneal; IP) 1 hour before cerebral Aβ injection. Green cells stained with NeuN represent neurons.

Behavioral Testing of TgSwDI Mice Treated with MTZ and ATZ for 8 Months and Tested at 15 Months Shows Neutral Effects of CAI Treatment on Body Weight, Death Rate, and Grip Strength.

Figure 25D:
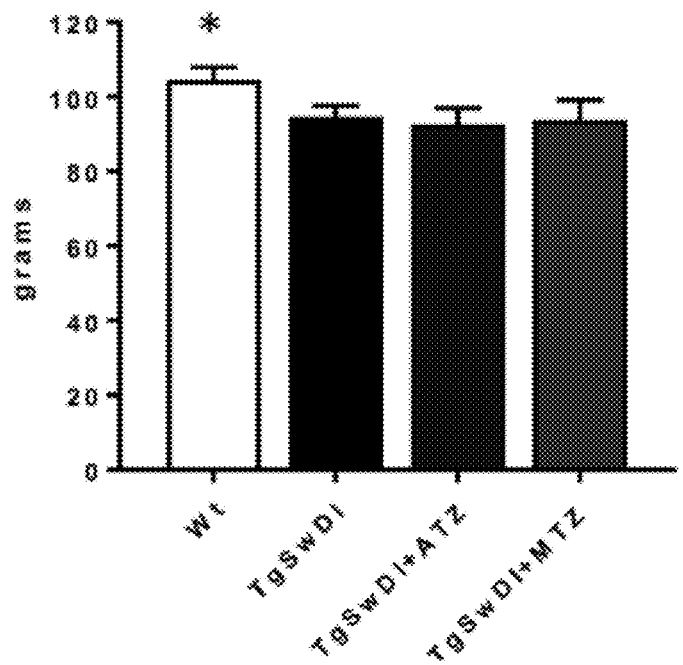
Figure 25E:
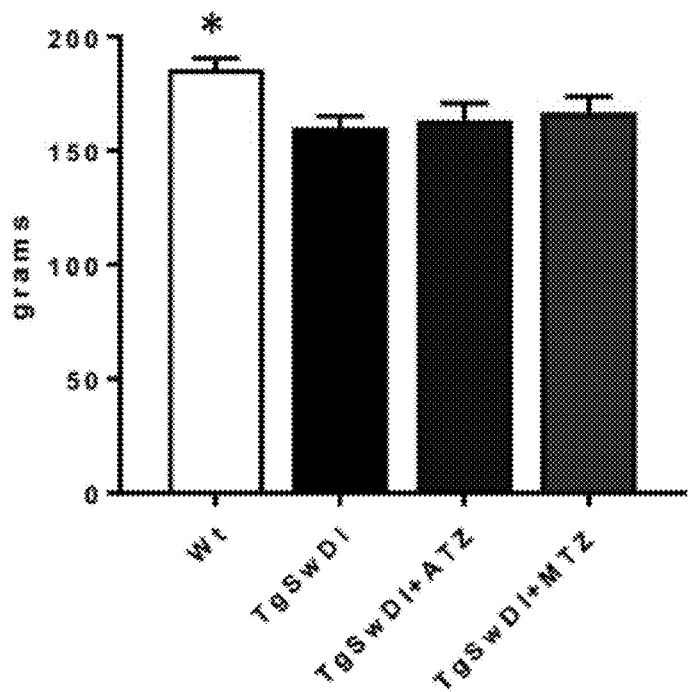

Mice were treated with the drugs incorporated in their diet starting at 6-7 months of age and tested at 15 months. There were no significant differences in body weight between WT and TgSwDI mice, or between TgSwDI and TgSwDI treated with the CAIs for 8 months (mice were tested at 15 months), suggesting that the drugs are well tolerated and do not cause weight loss (FIG. 25A). There were no weight differences in either females or males when groups are separated by gender (FIG. 25B). There were no differences in the death rates (between 2 months and 16 months) in TgSwDI mice and TgSwDI animals treated with the CAIs for the last 8 months, suggesting that the drugs are not toxic and are tolerated for long term treatment (FIG. 25C). WT mice have lower death rates than TgSwDI mice. There were no significant differences in forelimbs grip strength (FIG. 25D) or all limbs grip strength (FIG. 25E) between 15-16 months-old TgSwDI mice and age-matched TgSwDI treated with the CAIs for 8 months. WT mice consistently had more strength than TgSwDI mice. There were no strength differences in either females or males when groups are separated by gender (not shown). Given that there were no differences in body weight, death rate, or grip strength in mice treated with the CAIs, the CAIs do not affect these behavioral parameters.

Behavioral Testing of TgSwDI Mice Treated with MTZ and ATZ for 7 Months and Tested at 15 Months Shows Beneficial Effects of CAI Treatment on Barnes Maze Testing of Spatial Memory.

Figure 26A:
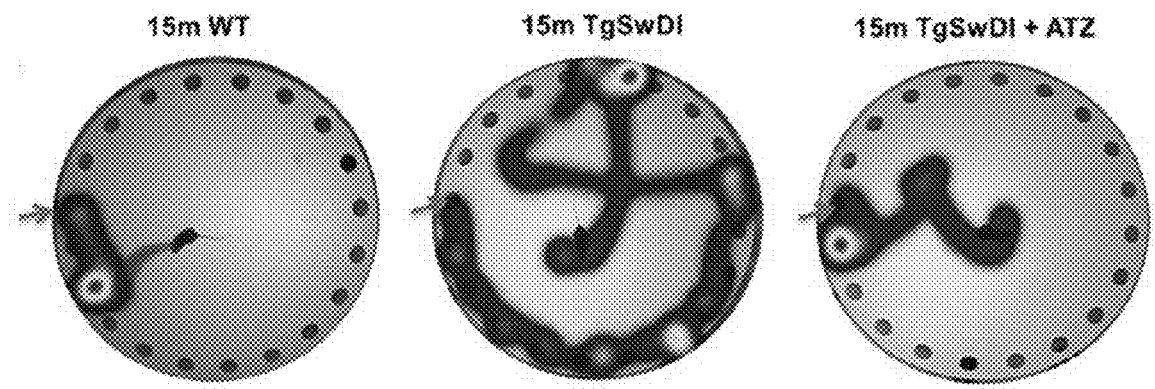
Figure 26B:
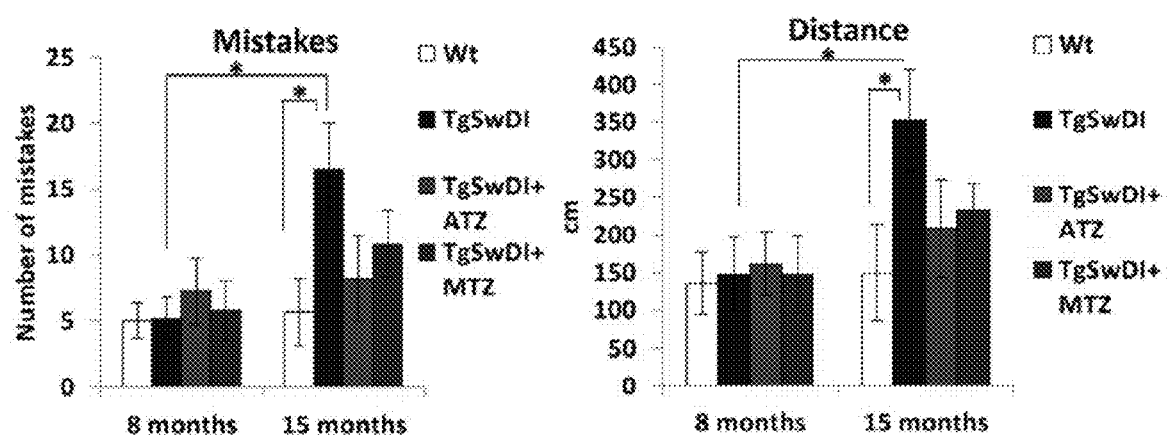

Spatial memory was assessed by Barnes Maze in younger (8-9 months) and older (15-16 months) Tg-SwDI and C57/B6 control mice. The presented data are from a probe test session in which navigation to the escape hole location (green arrows) was assessed following 10 prior training trials. FIG. 26A shows heat maps illustrating the navigation patterns of representative (median performance) 15-16-month old C57/B6 (n=10), Tg-SwDI (n=19), Tg-SwDI+MTZ (n=12), and Tg-SwDI mice+ATZ (n=9). FIG. 26B shows the mean (+SEM) of the total number of mistakes (left) and distance traveled (right) prior to trial completion. Data were averaged across roughly equivalent numbers of males and females in each group as there were no significant effects of gender. *15-16-month old Tg-SwDI mice were significantly impaired relative to younger Tg-SwDI mice ($p<0.05$) as well as to older C57/B6 controls ($p<0.05$). A 300-sec probe trial, conducted 1 h after the final training trial, was identical to the training trials except that all 12 holes were blocked. The mouse was therefore unable to escape the maze during the probe trial. Distance and mistakes for TgSwDI treated with MTZ and ATZ in the diet for 8 months was not significantly higher than WT mice, suggesting a protective effect of the drugs against loss of spatial memory. FIGS. 26 C-26D show the results of Barnes Maze testing in TgSwDI mice treated with MTZ and ATZ for 8 months and tested at 15-16 months. FIG. 26C shows the distance traveled in trial 10 (last trial), representing memory loss on the maze, was higher in TgSwDI mice than WT. FIG. 26D shows that the distance for TgSwDI mice treated with MTZ and ATZ was not significantly higher than WT mice, suggesting that both MTZ and ATZ restore memory to levels similar to the controls.

Staining of Aβ and GFAP in 16 Month-Old Mice (Treated for 8 Months with MTZ or ATZ) Shows Protective Effects of MTZ and ATZ Treatment.

Figure 27A:
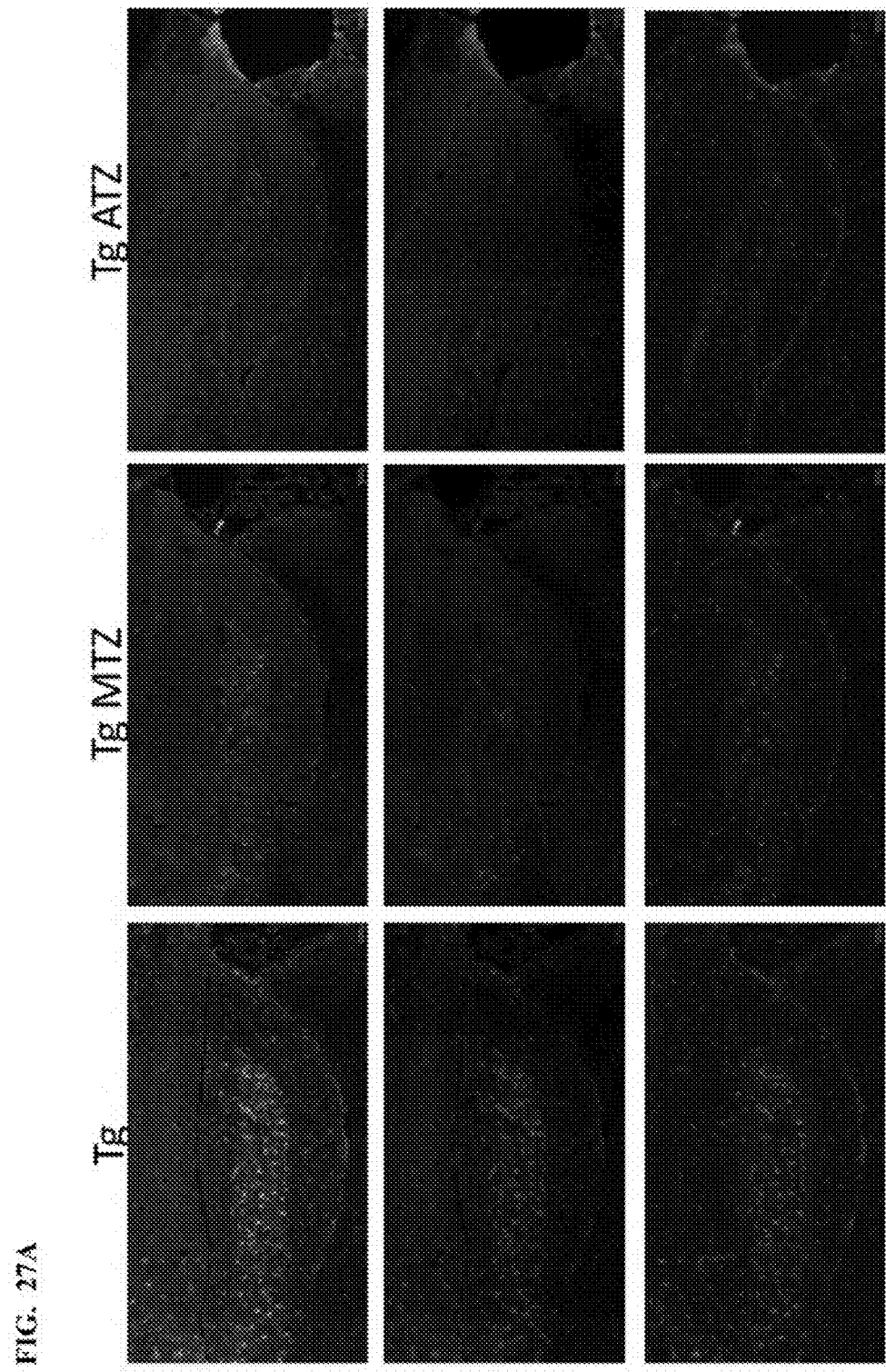
FIGS. 27A-27D. Staining of Aβ and GFAP in 16 month-old mice (treated for 8 months). Amyloid beta (Aβ) staining was represented in red, GFAP (glial fibrillary acidic protein) was in green, and Dapi was in Blue. The dentate gyrus (hippocampus), with co-localized GFAP and Aβ staining in TgSwDI mice (16 months), indicated the presence of Aβ inside glial cells, and gliosis in the TgSwDI mice brains (FIG. 27A). In TgSwDI mice treated with MTZ or ATZ, Aβ staining was not co-localized within glial cells, and both Aβ and GFAP were reduced, suggesting reduced glial toxicity and decreased amyloid deposition in the brains of CAI-treated TgSwDI animals. The same staining were performed in the mouse cortex (FIG. 27B). Similarly to the hippocampus, gliosis (green) and strong amyloid staining (red) were observed in glial cells (colocalization of Aβ with GFAP=yellow) in TgSwDI mice and a significant reduction of both GFAP and Aβ, as well as their colocalization, in TgSwDI mice treated with MTZ or ATZ. The entire hippocampus was stained as in FIGS. 27A-27B in treated and untreated mice (FIG. 27C). The results were similar to FIG. 27A (colocalization in TgSwDI mice, but not in treated TgSwDI mice). In addition, a clear reduction of amyloidosis in the CAIs-treated mice was observed. Both Amyloid and GFAP staining were reduced in the thalamic region of TgSwDI mice treated with the 2 CAIs, compared to untreated TgSwDI mice (FIG. 27D). In this region, colocalization of amyloid deposits and glial cells were not observed, but both decreased gliosis (green) and amyloidosis (red) in mice treated with MTZ and ATZ was observed.
Figure 27B:
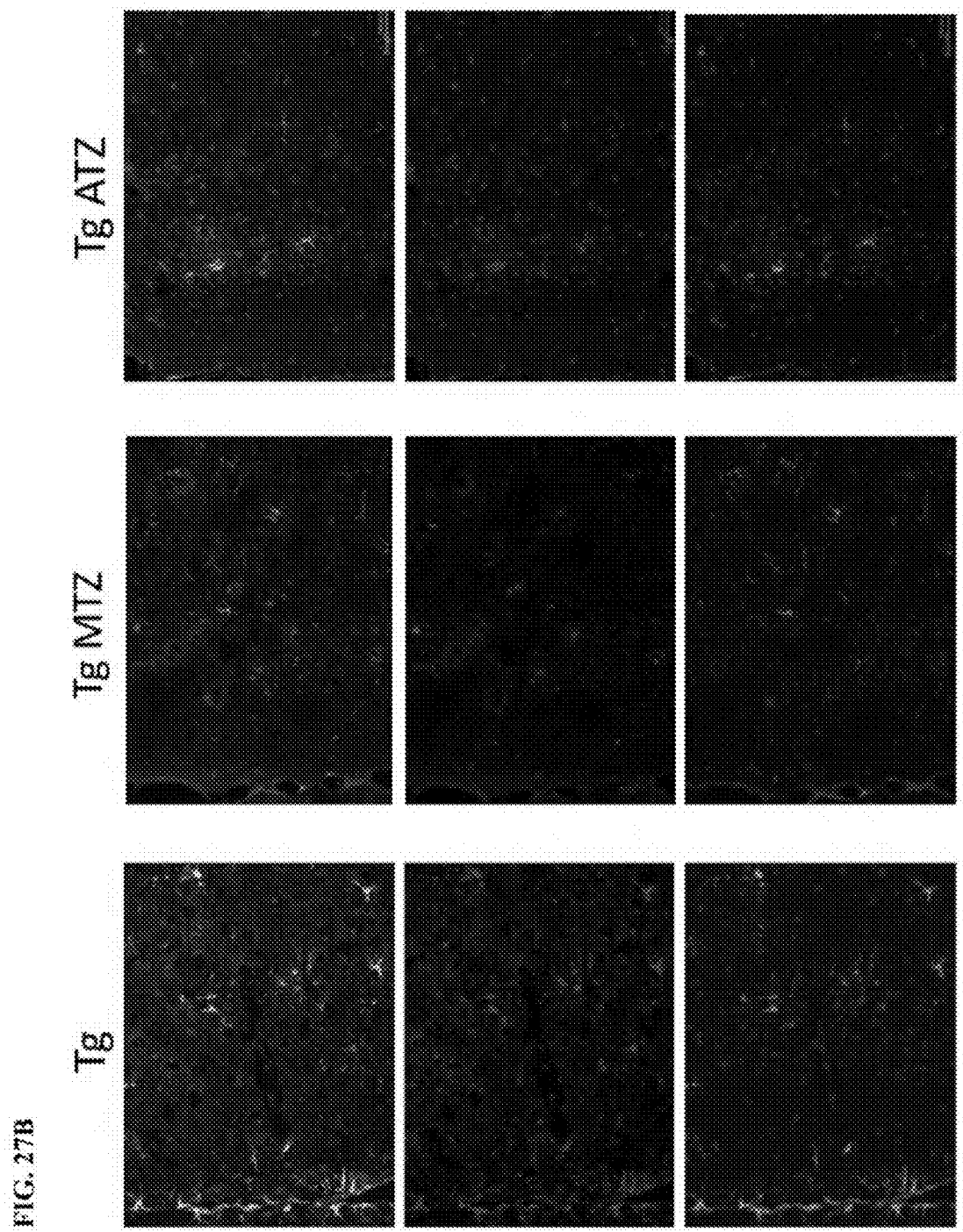
Figure 27C:
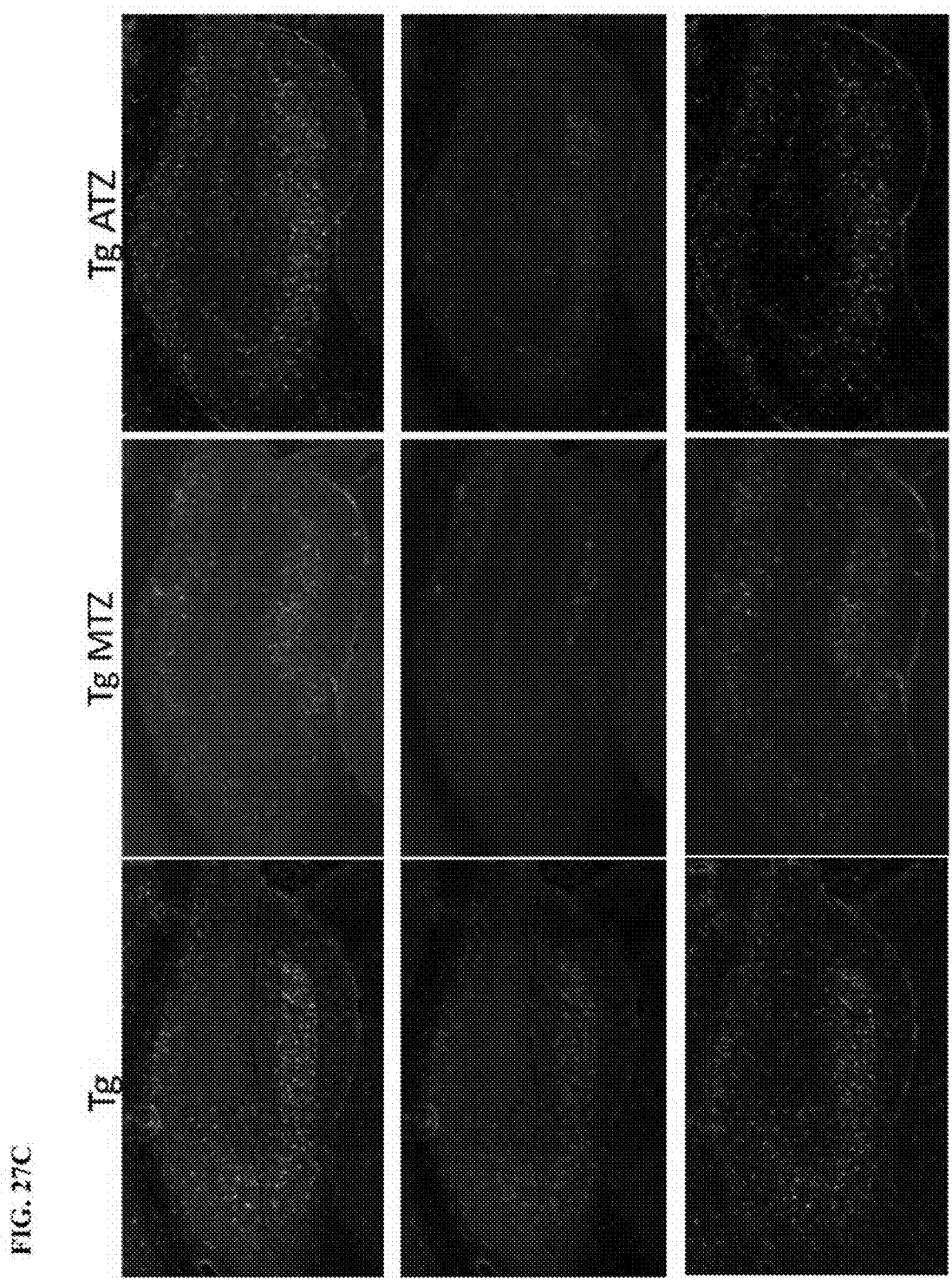
Figure 27D:
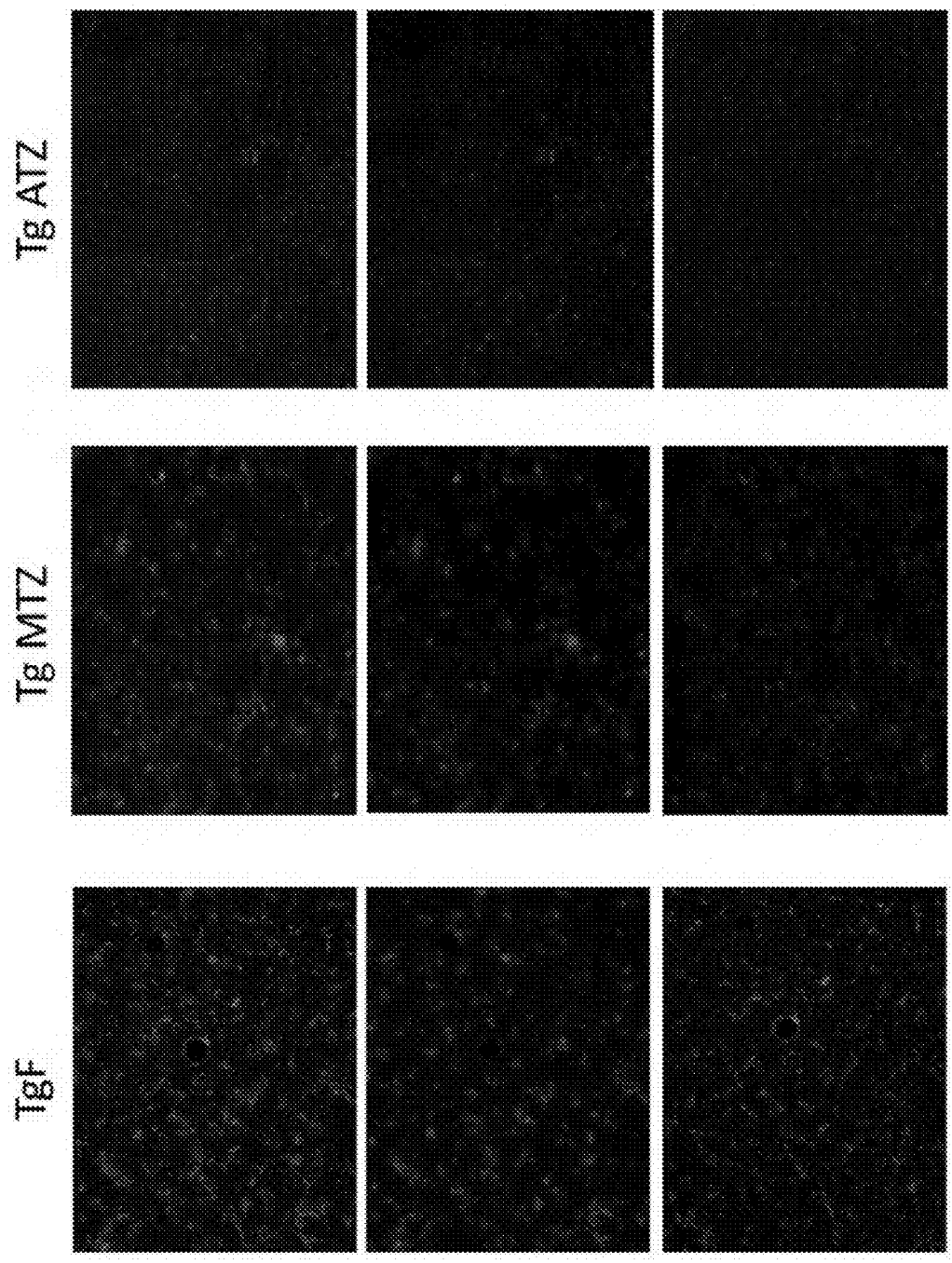

The protective effects of MTZ or ATZ treatment was assessed by immunohistochemistry assays in younger (8-9 months) and older (15-16 months) Tg-SwDI and C57/B6 control mice. In these experiments, amyloid beta (Aβ) staining was represented in red, GFAP (glial fibrillary acidic protein) was in green, and DAPI was in Blue. FIG. 27A depicts the dentate gyrus (hippocampus), with co-localized GFAP and Aβ staining in TgSwDI mice (16 months), indicated the presence of Aβ inside glial cells, and gliosis in the TgSwDI mice brains. In TgSwDI mice treated with MTZ or ATZ, Abeta staining was not co-localized within glial cells, and both Aβ and GFAP were reduced, suggesting reduced glial toxicity and decreased amyloid deposition in the brains of CAI-treated TgSwDI animals. FIG. 27B depicts the same stainings in the mouse cortex. Similarly to the hippocampus, gliosis (green) and strong amyloid staining (red) were observed in glial cells (colocalization of Abeta with GFAP=yellow) in TgSwDI mice and a significant reduction of both GFAP and Aβ, as well as their colocalization, in TgSwDI mice treated with MTZ or ATZ. FIG. 27C shows the entire hippocampus in treated and untreated mice, with the same stainings as FIGS. 27A-27B. The results were similar to FIG. 27A (colocalization in TgSwDI mice, but not in treated TgSwDI mice). In addition, a clear reduction of amyloidosis in the CAIs-treated mice was observed. FIG. 27D shows that both Amyloid and GFAP staining were reduced in the thalamic region of TgSwDI mice treated with the 2 CAIs, compared to untreated TgSwDI mice. In this region, colocalization of amyloid deposits and glial cells were not observed, but both decreased gliosis (green) and amyloidosis (red) in mice treated with MTZ and ATZ was observed.

Thioflavin Staining in TgSwDI and WT Mice Brain Sections Shows Beneficial Effects of MTZ or ATZ Treatment in Immunohistochemical Analyses of Brain Slices.

Figure 28A:
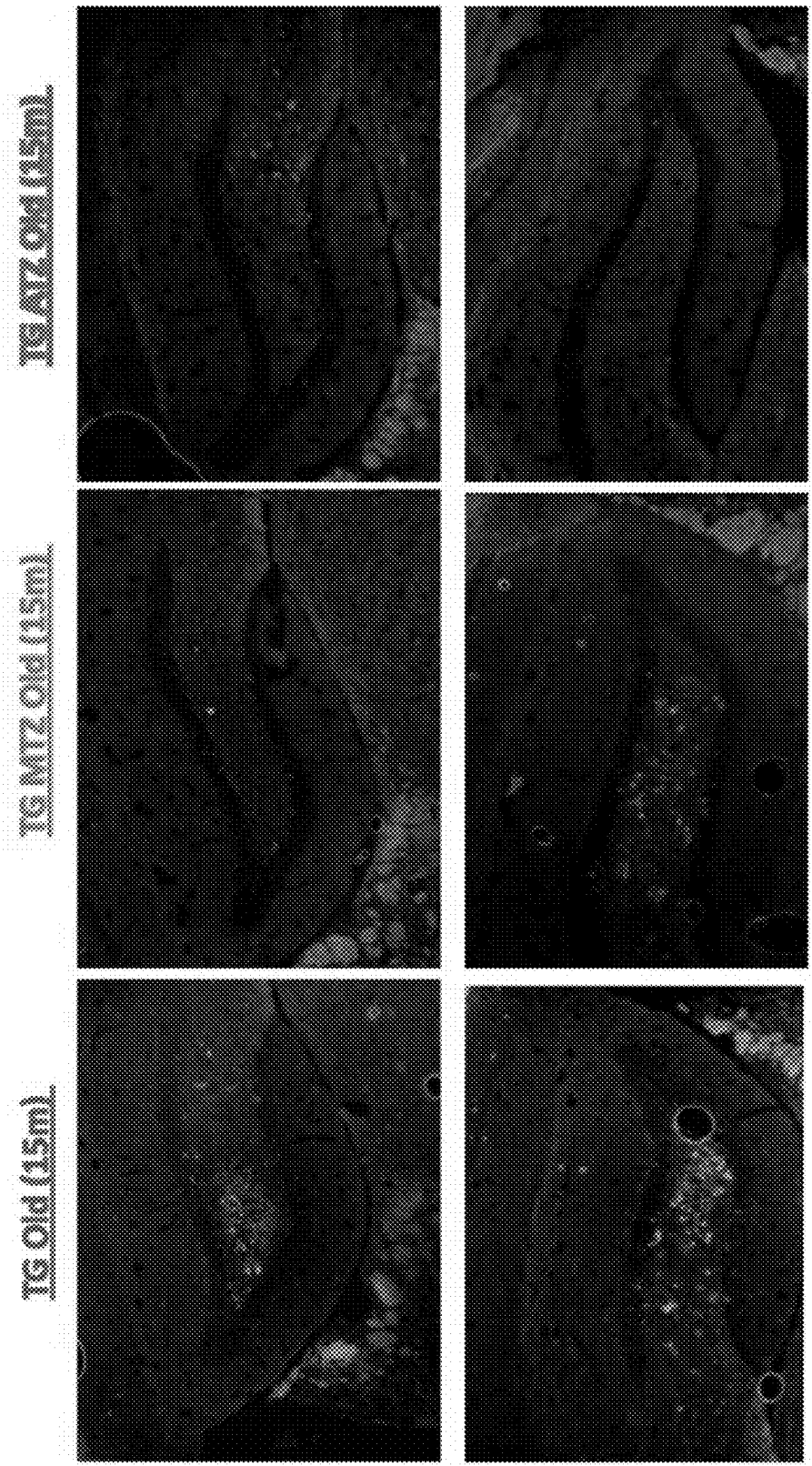
FIGS. 28A-28D. Thioflavin staining in TgSwDI and WT mice brain sections. Both MTZ and ATZ were given at 15-20 mg/kg/day (incorporated in the diet). Drugs were incorporated in the mouse diet at 100 ppm by TestDiets. Thioflavin S staining was performed to detect amyloid deposits in 16 months old TgSwDI mice, in the presence or absence of the CAIs. Amyloid load (bright green fluorescence in FIGS. 28A-28D) was reduced in the brain of mice treated with both MTZ and ATZ, consistently with a positive effect of the drugs on activating cerebral blood flow and clearance of waste products from the brain. Based on these data, MTZ and ATZ can have a double positive effect in AD: reducing mitochondrial dysfunction and apoptotic cell death (as shown and discussed in previous data), as well as reducing amyloid deposition, likely though the CAIs' known vasoactive effects, which increase clearance in the brain.
Figure 28B:
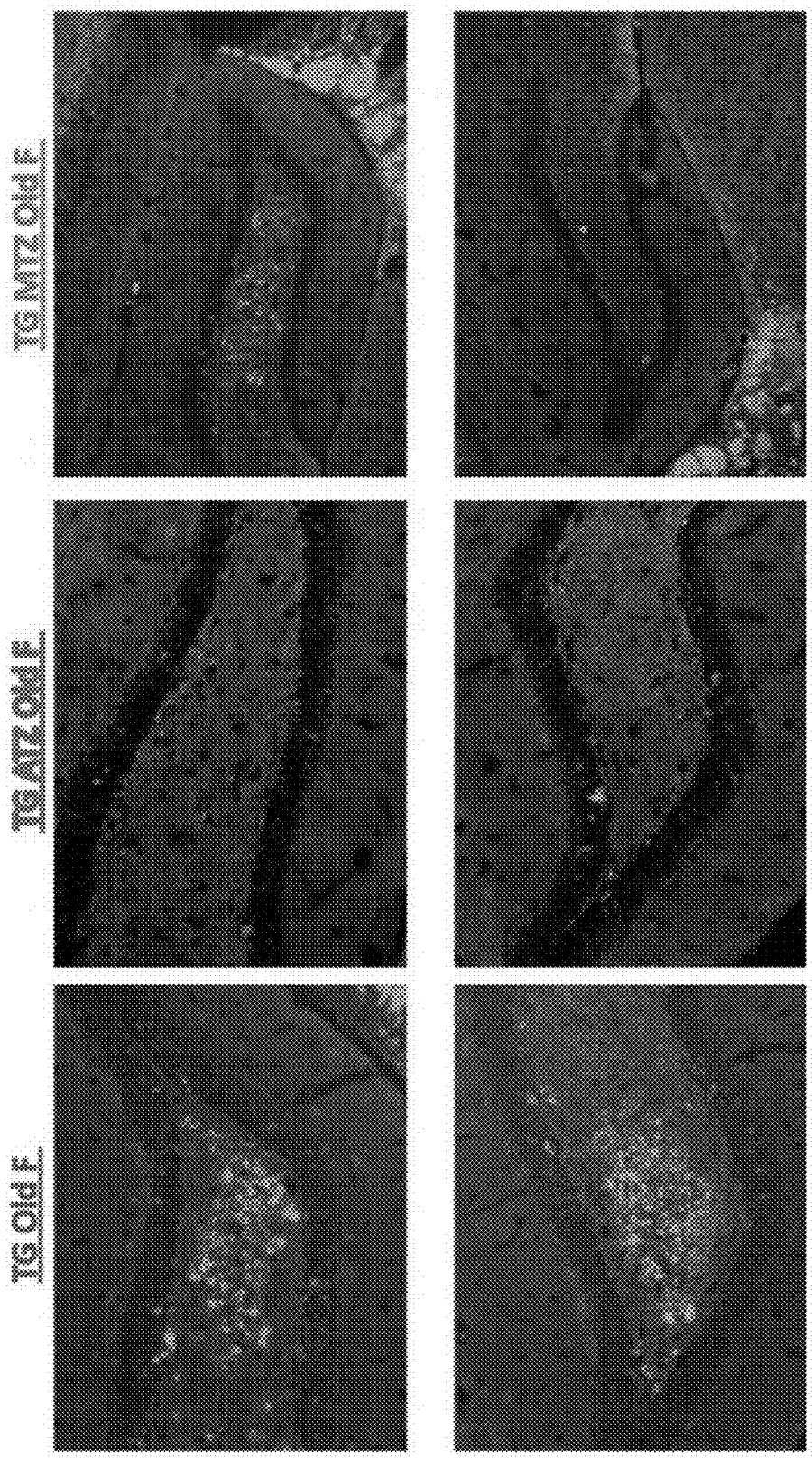
Figure 28C:
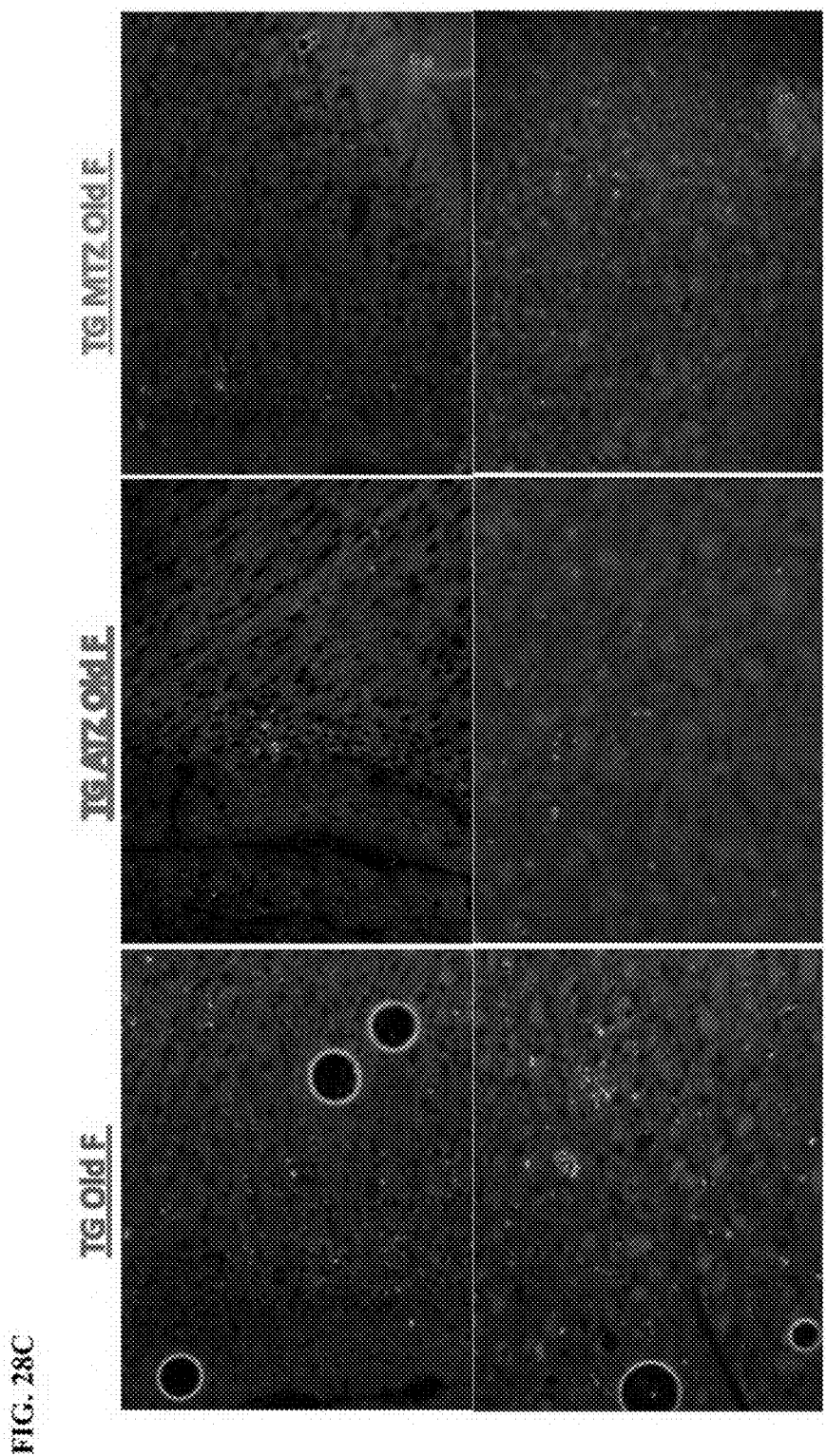
Figure 28D:
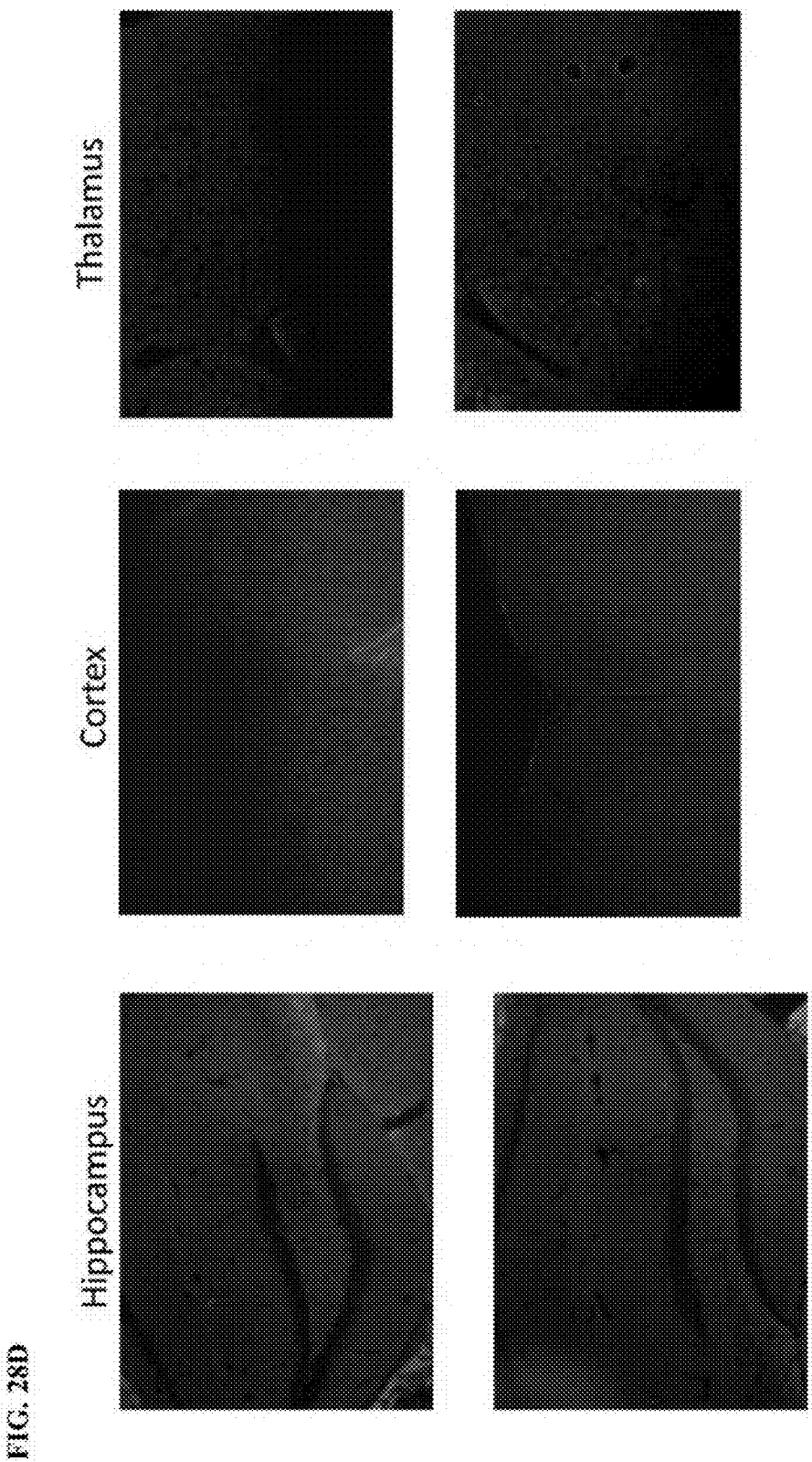

Thioflavin S staining was performed to detect amyloid deposits in 16 months old TgSwDI mice, in the presence or absence of the CAIs. Amyloid load (bright green fluorescence in FIGS. 28A-28D was reduced in the brain of mice treated with both MTZ and ATZ, consistently with a positive effect of the drugs on activating cerebral blood flow and clearance of waste products from the brain, as well as with improved glia-mediated elimination of amyloid. Based on these data, MTZ and ATZ can have a double positive effect in AD: reducing mitochondrial dysfunction and apoptotic cell death in multiple cell types including neurons, endothelial and glial cells (as shown and discussed in previous data), as well as reducing amyloid deposition, likely though the CAIs' known vasoactive effects, which increase clearance in the brain, and possibly improving the health of glial cells (reduced caspase activation), making them more efficient at eliminating amyloid deposits. FIGS. 28A-28B represent an area of the hippocampus including the dentate gyrus at respectively 10× (FIG. 28A) and 20× (FIG. 28B) magnification, in 16 months old TgSwDI. Thioflavin S bright green fluorescence stained amyloid deposits. There was an effect of the drugs on amyloid deposition, with both Methazolamide (MTZ) and acetazolamide (ATZ) inducing a decrease in the hippocampal deposition of Amyloid beta (Aβ). Mice were subjected to the drug regimen (incorporated in their diet as described in Methods) for 8 months. FIG. 28C represents the accumulation of amyloid deposits stained by Thioflavin S in the cortex (top panels) and in the thalamic region (bottom panels), in 16 months old mice subjected to drug treatment as above. ATZ and MTZ also reduced deposition in these brain areas. FIG. 28D shows Thioflavin S staining in age-matched Wild Type (WT) mice as a negative control. No amyloid deposition was observed in the WT brain, either in the hippocampus, the cortex, or the thalamus.
Immunofluorescence Deconvolution Microscopy Detection of CytC after 1 day incubation with the most toxic of the Aβ peptides, Aβ-Iowa(isoD), in the presence of methazolamide was performed as described above. Treatment with Aβ resulted not only in release of CytC, but also in a less intense more diffuse MitoTracker® staining indicative of the poor localization of the oxidized dye to the organelles, which is dependent on mitochondrial membrane potential.

Co-incubation with methazolamide (starting at 100 μM) not only preserved the subcellular localization of CytC, but restored the mitochondrial membrane potential as visualized by the localization of MitoTracker® to the organelles.
Discussion AD is a complex, multi-causal disease, affecting nearly 44 million people worldwide [45]. Mitochondrial dysfunctions have been deeply described in this disease [1-3, 5, 46, 47], being an early step in AD progression, preceding the cognitive impairment. However, the specific biochemical pathways leading to these mitochondrial dysfunctions and apoptotic cell death have not yet been elucidated. Based on the data provided herein, it is likely that the mitochondrial carbonic anhydrase enzyme is an active, previously unrecognized, key actor in this process. The present data show a clear mitochondrial membrane depolarization, as well as an increase in the $H_2O_2$ generation, in response to Aβ-induced toxicity. Both effects are inhibited or reverted by MTZ and AZT, two different members of the CAI family. The data also show that the two CAIs inhibit apoptotic cell death in neuronal, endothelial and glial cells. MTZ and ATZ also inhibit caspase 9 and 3 activation, CytC release and loss of mitochondrial membrane potential induced by Aβ.

The Aβ peptide is a well-known inducer of different types of ROS [48-50], as $H_2O_2$ [51]. The important role played by $H_2O_2$ in the activation of the apoptotic cell death described herein is concordant with previous works showing that increments is the generation of this molecule are early events in the Aβ-induced toxicity [52, 53]. In the present model, these increments and the mitochondrial membrane depolarization, which is also a key process in AD pathogenesis (reviewed in [12]), are the primary inductors of the apoptotic cell death. Both membrane depolarization and apoptotic activation were clearly reverted by the inhibition of carbonic anhydrase by the CAIs ATZ and MTZ. These effects implicate carbonic anhydrase in the pathogenesis of AD.

In light of the protective effects on membrane potential and $H_2O_2$ production, the possible effects of CAIs on ATP levels were examined. Interestingly, neither MTZ nor AZT treatments exerted a significant effect on steady state ATP as measured using a luciferin-luciferase luminescence assay. These results suggest that the protective effects of CAIs against amyloid peptides were not due to an increase in mitochondrial respiration.

It has been demonstrated that $Ca^{2+}$ homeostasis is dysregulated in different models of AD, as well as in human brains [62-65]. Mutations in presenelin in sporadic AD are involved in the dysregulation of the levels of $Ca^{2+}$ found in the ER [66-68]. Moreover, some studies have suggested an important role for the ER-mitochondria contacts, also in the sporadic forms of the disease [69, 70]. The present data show a decrease in the levels of free calcium, both in mitochondria and cytoplasm, after the addition of the Aβ peptides. The observed effect on mitochondrial and cytoplasmic calcium concentration was partially rescued by the highest concentrations of the CAIs in the case of the endovascular cells, reaching values similar to those found under control conditions, while no reversion of the effect was observed in the case of the dopaminergic neurons. This result suggests that mitochondrial carbonic anhydrase effects on Aβ-induced toxicity are independent of calcium uptake in both mitochondria and cytoplasm.

Because of the implication of carbonic anhydrase in the generation of pH-affecting molecules, studies were conducted to determine whether the Aβ-induced toxicity was due to changes in the intracellular pH and, thus, if the protective effects of CAIs were secondary to the restoration of the initial pH values. No changes in the pH were found.

Apoptotic cell death in response to Aβ-induced toxicity was activated in different cell lines. In fact, increasing caspase 3 and 9 activation and CytC release, were induced subsequently to the Aβ addition to dopaminergic neurons, microvascular endothelial cells and glial cells. In the data herein, it is shown that MTZ and AZT, were able to reverse the observed effects on apoptotic cell death induction.

The search of any pharmacological strategy to prevent or to cure AD is now a priority within the scientific community and the pharmaceutical companies. For that, it is important to elucidate the molecular and biochemical pathways involved in the Aβ-induced toxicity. The data herein suggest a new and key role for the mitochondrial carbonic anhydrase enzyme in the Aβ-induced neuronal and microvascular endothelial toxicity, both key processes in AD etiopathology. The protective effect exerted by MTZ and AZT, on preventing mitochondrial dysfunction paves the way to the use of such drugs for neurodegenerative diseases.

Both MTZ and AZT consistently prevented specific pathways of mitochondrial dysfunction induced by Aβ in cerebral microvascular endothelial, neuronal and glial cells, without affecting ATP production, pH, and Calcium flux. Increase of hydrogen peroxide, loss of mitochondrial membrane potential, release of Cytochrome C, caspase activation, and apoptotic cell death were inhibited by CAIs. ATZ was effective at concentrations significantly lower than MTZ (10 μM vs 100 μM). Both drugs, given with diet, were able to ameliorate behavioral paradigms in relatively young TgSwDI mice. Mitochondrial dysfunction and CytC release, as well as caspase activation and apoptosis caused by Aβ in neuronal, endothelial and glial cells in culture are prevented by CAIs. MTZ, given systemically before peptide intrahippocampal injection, inhibits caspase 3 activation in neuronal and glial cells in the mouse brain and prevents hippocampal neuronal loss. MTZ and ATZ ameliorate behavioral phenotypes (Radial arm maze) in TgSwDI mice presenting vascular and parenchymal amyloid deposits, without showing signs of toxicity, weight loss or increased death of the animals. Importantly, the CAIs also reduced amyloid deposition in the hippocampus, cortex and thalamic areas of the transgenic mice, and both the amount of GFAP stained glial cells and the amount of colocalization of Aβ with GFAP-positive glia was reduced in Tg mice in the presence of both CAI. Therefore, MTZ, ATZ, and analog CAIs represent a new and exciting pharmacological strategy against mitochondrial dysfunction, caspase activation and neurodegeneration in mouse models of vascular and parenchymal amyloidosis and Alzheimer's disease. Based on the targeting of a mitochondrial dysfunction component present in multiple neurodegenerative disorders, these CAIs are a potential therapeutic strategy for Alzheimer's disease (AD), Mild Cognitive Impairment (MCI), Parkinson's disease (PD), Huntington's disease (HD), prion-caused diseases, frontotemporal dementia (FTD), Lewy body dementia, vascular dementias, white matter disease, traumatic brain injury, post-traumatic stress, stroke, tauopaties, Down Syndrome, Amyotrophic Later Sclerosis (ALS), chronic traumatic encephalopathy (CTE), progressive supranuclear palsy (PSP), multiple system atrophy (MSA), corticobasal degeneration (CBGD), Pick's disease, olivopontocerebellar atrophy (OPCA), senile dementia of the Alzheimer type, progressive supranuclear palsy (Steel-Richardson-Olszewski), corticodentatonigral degeneration, Hallervorden-Spatz disease, striatonigral degeneration, torsion dystonia (e.g., torsion spasm; dystonia musculorum deformans), spasmodic torticollis and other dyskinesis, familial tremor, Gilles de la Tourette syndrome, cerebellar cortical degeneration, spinocerebellar degeneration (e.g., Friedreich's ataxia and related disorders), Shy-Drager syndrome, spinal muscular atrophy, primary lateral sclerosis, hereditary spastic paraplegia, peroneal muscular atrophy (Charcot-Marie-Tooth), hypertrophic interstitial polyneuropathy (Dejerine-Sottas), chronic progressive neuropathy, pigmentary degeneration of the retina (retinitis pigmentosa), and hereditary optic atrophy (Leber's disease).

REFERENCES

Aamand, R., et al., 2011. Enhancing effects of acetazolamide on neuronal activity correlate with enhanced visual processing ability in humans. Neuropharmacology. 61, 900-8.

Almasalmeh, A., et al., 2014. Structural determinants of the hydrogen peroxide permeability of aquaporins. FEBS J. 281, 647-56.

Atamna, H., Frey, W. H., 2nd, 2007. Mechanisms of mitochondrial dysfunction and energy deficiency in Alzheimer's disease. Mitochondrion. 7, 297-310.

Balietti, M., et al., 2013. Early selective vulnerability of synapses and synaptic mitochondria in the hippocampal CA1 region of the Tg2576 mouse model of Alzheimer's disease. J Alzheimers Dis. 34, 887-96.

Bashir, M., et al., 2014. beta-Amyloid-evoked apoptotic cell death is mediated through MKK6-p66shc pathway. Neuromolecular Med. 16, 137-49.

Beal, M. F., 2005. Oxidative damage as an early marker of Alzheimer's disease and mild cognitive impairment. Neurobiol Aging. 26, 585-6.

Bickler, P. E., et al., 1988. Effects of acetazolamide on cerebral acid-base balance. J Appl Physiol (1985). 65, 422-7.

Block, M. L., et al., 2007. Microglia-mediated neurotoxicity: uncovering the molecular mechanisms. Nat Rev Neurosci. 8, 57-69.

Braun, J. S., et al., 1999. Neuroprotection by a caspase inhibitor in acute bacterial meningitis. Nat Med. 5, 298-302.

Burguillos, M. A., et al., 2011. Caspase signalling controls microglia activation and neurotoxicity. Nature. 472, 319-24.

Calkins, M. J., et al., 2011. Impaired mitochondrial biogenesis, defective axonal transport of mitochondria, abnormal mitochondrial dynamics and synaptic degeneration in a mouse model of Alzheimer's disease. Hum Mol Genet. 20, 4515-29.

Chang, Y. J., Chen, Y. R., 2014. The coexistence of an equal amount of Alzheimer's amyloid-beta 40 and 42 forms structurally stable and toxic oligomers through a distinct pathway. FEBS J. 281, 2674-87.

Choi, S. H., et al., 2005. Inhibition of thrombin-induced microglial activation and NADPH oxidase by minocycline protects dopaminergic neurons in the substantia nigra in vivo. J Neurochem. 95, 1755-65.

Cruz, L., et al., 2005. Solvent and mutation effects on the nucleation of amyloid beta-protein folding. Proc Natl Acad Sci USA. 102, 18258-63.

Cutillas, B., et al., 1999. Caspase inhibition protects nigral neurons against 6-OHDA-induced retrograde degeneration. Neuroreport. 10, 2605-8.

D'Amelio, M., et al., 2011. Caspase-3 triggers early synaptic dysfunction in a mouse model of Alzheimer's disease. Nat Neurosci. 14, 69-76.

de Calignon, A., et al., 2010. Caspase activation precedes and leads to tangles. Nature. 464, 1201-4.

Ding, Y., et al., 2008. Endogenous hydrogen peroxide regulates glutathione redox via nuclear factor erythroid 2-related factor 2 downstream of phosphatidylinositol 3-kinase during muscle differentiation. Am J Pathol. 172, 1529-41.

Du, H., et al., 2010. Early deficits in synaptic mitochondria in an Alzheimer's disease mouse model. Proc Natl Acad Sci USA. 107, 18670-5.

Duffy, A. M., et al., 2011. A selective role for ARMS/Kidins220 scaffold protein in spatial memory and trophic support of entorhinal and frontal cortical neurons. Exp Neurol. 229, 409-20.

Eckert, A., et al., 2003a. Mitochondrial dysfunction, apoptotic cell death, and Alzheimer's disease. Biochem Pharmacol. 66, 1627-34.

Eckert, A., et al., 2003b. Increased apoptotic cell death in sporadic and genetic Alzheimer's disease. Ann N Y Acad Sci. 1010, 604-9.

Forman, H. J., et al., 2004. Redox signaling: thiol chemistry defines which reactive oxygen and nitrogen species can act as second messengers. Am J Physiol Cell Physiol. 287, C246-56.

Fossati, S., et al., 2010. Differential activation of mitochondrial apoptotic pathways by vasculotropic amyloid-beta variants in cells composing the cerebral vessel walls. FASEB J. 24, 229-41.

Fossati, S., et al., 2012a. Insights into Caspase-Mediated Apoptotic Pathways Induced by Amyloid-beta in Cerebral Microvascular Endothelial Cells. Neurodegenerative Diseases. 10, 324-328.

Fossati, S., et al., 2012b. TRAIL death receptors DR4 and DR5 mediate cerebral microvascular endothelial cell apoptosis induced by oligomeric Alzheimer's Abeta. Cell Death Dis. 3, e321.

Fossati, S., et al., 2013. Differential contribution of isoaspartate post-translational modifications to the fibrillization and toxic properties of amyloid-beta and the asparagine 23 Iowa mutation. Biochem J.

Friedlander, R. M., 2003. Apoptosis and caspases in neurodegenerative diseases. N Engl J Med. 348, 1365-75.

Giacomotto, J., et al., 2009. Evaluation of the therapeutic potential of carbonic anhydrase inhibitors in two animal models of dystrophin deficient muscular dystrophy. Hum Mol Genet. 18, 4089-101.

Gill, T., Levine, A. D., 2013. Mitochondria-derived hydrogen peroxide selectively enhances T cell receptor-initiated signal transduction. J Biol Chem. 288, 26246-55.

Grossmann, W. M., Koeberle, B., 2000. The dose-response relationship of acetazolamide on the cerebral blood flow in normal subjects. Cerebrovasc Dis. 10, 65-9.

Jiang, X., Wang, X., 2000. Cytochrome c promotes caspase-9 activation by inducing nucleotide binding to Apaf-1. J Biol Chem. 275, 31199-203.

Kim, H. E., et al., 2005. Formation of apoptosome is initiated by cytochrome c-induced dATP hydrolysis and subsequent nucleotide exchange on Apaf-1. Proc Natl Acad Sci USA. 102, 17545-50.

Kim, J., et al., 2014. Beta-amyloid oligomers activate apoptotic BAK pore for cytochrome c release. Biophys J. 107, 1601-8.

Lee, S., et al., 2011. Mitochondrial $H_2O_2$ generated from electron transport chain complex I stimulates muscle differentiation. Cell Res. 21, 817-34.

Luo, P., et al., 2012. Protective effect of Homer 1a against hydrogen peroxide-induced oxidative stress in PC12 cells. Free Radic Res. 46, 766-76.

Marques, C. A., et al., 2003. Neurotoxic mechanisms caused by the Alzheimer's disease-linked Swedish amyloid precursor protein mutation: oxidative stress, caspases, and the JNK pathway. J Biol Chem. 278, 28294-302.

Modi, K. K., et al., 2014. A physically-modified saline suppresses neuronal apoptosis, attenuates tau phosphorylation and protects memory in an animal model of Alzheimer's disease. PLoS One. 9, e103606.

Moreira, P. I., et al., 2010a. Mitochondrial dysfunction is a trigger of Alzheimer's disease pathophysiology. Biochim Biophys Acta. 1802, 2-10.

Moreira, P. I., et al., 2010b. Mitochondria: a therapeutic target in neurodegeneration. Biochim Biophys Acta. 1802, 212-20.

Parajuli, B., et al., 2013. Oligomeric amyloid beta induces IL-1beta processing via production of ROS: implication in Alzheimer's disease. Cell Death Dis. 4, e975.

Price, K. A., et al., 2014. Altered synaptic structure in the hippocampus in a mouse model of Alzheimer's disease with soluble amyloid-beta oligomers and no plaque pathology. Mol Neurodegener. 9, 41.

Ryu, J. K., et al., 2003. Microglial activation and cell death induced by the mitochondrial toxin 3-nitropropionic acid: in vitro and in vivo studies. Neurobiol Dis. 12, 121-32.

Saito, Y., et al., 2007. Molecular mechanisms of 6-hydroxydopamine-induced cytotoxicity in PC12 cells: involvement of hydrogen peroxide-dependent and -independent action. Free Radic Biol Med. 42, 675-85.

Santos, R. X., et al., 2013. Mitochondrial DNA oxidative damage and repair in aging and Alzheimer's disease. Antioxid Redox Signal. 18, 2444-57.

Schulz, J. B., et al., 1998. Extended therapeutic window for caspase inhibition and synergy with MK-801 in the treatment of cerebral histotoxic hypoxia. Cell Death Differ. 5, 847-57.

Shah, G. N., et al., 2013a. High glucose-induced mitochondrial respiration and reactive oxygen species in mouse cerebral pericytes is reversed by pharmacological inhibition of mitochondrial carbonic anhydrases: Implications for cerebral microvascular disease in diabetes. Biochem Biophys Res Commun. 440, 354-8.

Shah, G. N., et al., 2013b. Pharmacological inhibition of mitochondrial carbonic anhydrases protects mouse cerebral pericytes from high glucose-induced oxidative stress and apoptosis. J Pharmacol Exp Ther. 344, 637-45.

Smale, G., et al., 1995. Evidence for apoptotic cell death in Alzheimer's disease. Exp Neurol. 133, 225-30.

Solesio, M. E., et al., 2013a. The mitochondria-targeted anti-oxidant MitoQ reduces aspects of mitochondrial fission in the 6-OHDA cell model of Parkinson's disease. Biochim Biophys Acta. 1832, 174-82.

Solesio, M. E., et al., 2013b. 3-Nitropropionic acid induces autophagy by forming mitochondrial permeability transition pores rather than activating the mitochondrial fission pathway. Br J Pharmacol. 168, 63-75.

Solito, R., et al., 2009. Dutch and Arctic mutant peptides of beta amyloid(1-40) differentially affect the FGF-2 pathway in brain endothelium. Exp Cell Res. 315, 385-95.

Stadelmann, C., et al., 1999. Activation of caspase-3 in single neurons and autophagic granules of granulovacuolar degeneration in Alzheimer's disease. Evidence for apoptotic cell death. Am J Pathol. 155, 1459-66.

Swerdlow, R. H., et al., 2010. The Alzheimer's disease mitochondrial cascade hypothesis. J Alzheimers Dis. 20 Suppl 2, S265-79.

Tada-Oikawa, S., et al., 1999. Generation of hydrogen peroxide precedes loss of mitochondrial membrane potential during DNA alkylation-induced apoptosis. FEBS Lett. 442, 65-9.

Viana, R. J., et al., 2009. Tauroursodeoxycholic acid prevents E22Q Alzheimer's Abeta toxicity in human cerebral endothelial cells. Cell Mol Life Sci. 66, 1094-104.

Walsh, D. M., et al., 1999. Amyloid beta-protein fibrillogenesis. Structure and biological activity of protofibrillar intermediates. J Biol Chem. 274, 25945-52.

Wang, X., et al., 2009. Methazolamide and melatonin inhibit mitochondrial cytochrome C release and are neuroprotective in experimental models of ischemic injury. Stroke. 40, 1877-85.

Wang, X., et al., 2003. Minocycline inhibits caspase-independent and -dependent mitochondrial cell death pathways in models of Huntington's disease. Proc Natl Acad Sci USA. 100, 10483-7.

Wang, X., et al., 2008. Inhibitors of cytochrome c release with therapeutic potential for Huntington's disease. J Neurosci. 28, 9473-85.

Wright, A., et al., 2008. High hopes at high altitudes: pharmacotherapy for acute mountain sickness and high-altitude cerebral and pulmonary oedema. Expert Opin Pharmacother. 9, 119-27.

Wu, K. L., et al., 2010. Loss of neuronal protein expression in mouse hippocampus after irradiation. J Neuropathol Exp Neurol. 69, 272-80.

Xie, H., et al., 2013. Mitochondrial alterations near amyloid plaques in an Alzheimer's disease mouse model. J Neurosci. 33, 17042-51.

Zhou, Q., et al., 2014. Rotenone Induction of Hydrogen Peroxide Inhibits mTOR-mediated S6K1 and 4E-BP1/eIF4E Pathways, Leading to Neuronal Apoptosis. Toxicol Sci.

Zhu, C. L., et al., 2004. [Cytochrome C release and apoptosis in neonatal rat cerebral hypoxia-ischemia]. Zhonghua Er Ke Za Zhi. 42, 437-40.

Zhu, S., et al., 2002. Minocycline inhibits cytochrome c release and delays progression of amyotrophic lateral sclerosis in mice. Nature. 417, 74-8.

Zussy, C., et al., 2013. Alzheimer's disease related markers, cellular toxicity and behavioral deficits induced six weeks after oligomeric amyloid-beta peptide injection in rats. PLoS One. 8, e53117.

1. Atamna, H. and W. H. Frey, 2nd, *Mechanisms of mitochondrial dysfunction and energy deficiency in Alzheimer's disease.* Mitochondrion, 2007. 7(5): p. 297-310.

2. Beal, M. F., *Oxidative damage as an early marker of Alzheimer's disease and mild cognitive impairment.* Neurobiol Aging, 2005. 26(5): p. 585-6.

3. Moreira, P. I., et al., *Mitochondrial dysfunction is a trigger of Alzheimer's disease pathophysiology.* Biochim Biophys Acta, 2010. 1802(1): p. 2-10.

4. Santos, R. X., et al., *Mitochondrial DNA oxidative damage and repair in aging and Alzheimer's disease.* Antioxid Redox Signal, 2013. 18(18): p. 2444-57.

5. Moreira, P. I., et al., *Mitochondria: a therapeutic target in neurodegeneration.* Biochim Biophys Acta, 2010. 1802(1): p. 212-20.

6. Miller, G., *Pharmacology. The puzzling rise and fall of a dark-horse Alzheimer's drug.* Science, 2010. 327(5971): p. 1309.

7. Doody, R. S., et al., *Effect of dimebon on cognition, activities of daily living, behaviour, and global function in patients with mild-to-moderate Alzheimer's disease: a randomised, double-blind, placebo-controlled study.* Lancet, 2008. 372(9634): p. 207-15.

8. Dumont, M. and M. F. Beal, *Neuroprotective strategies involving ROS in Alzheimer disease.* Free Radic Biol Med, 2011. 51(5): p. 1014-26.

9. Xie, H., et al., *Mitochondrial alterations near amyloid plaques in an Alzheimer's disease mouse model.* J Neurosci, 2013. 33(43): p. 17042-51.

10. Fossati, S., et al., *Differential activation of mitochondrial apoptotic pathways by vasculotropic amyloid-beta variants in cells composing the cerebral vessel walls.* FASEB J, 2010. 24(1): p. 229-41.

11. Fossati, S., et al., *Differential contribution of isoaspartate post-translational modifications to the fibrillization and toxic properties of amyloid-beta and the asparagine 23 Iowa mutation.* Biochem J, 2013.

12. Wang, X., et al., *Methazolamide and melatonin inhibit mitochondrial cytochrome C release and are neuroprotective in experimental models of ischemic injury.* Stroke, 2009. 40(5): p. 1877-85.

13. Wang, X., et al., *Inhibitors of cytochrome c release with therapeutic potential for Huntington's disease.* J Neurosci, 2008. 28(38): p. 9473-85.

14. Wright, A., S. Brearey, and C. Imray, *High hopes at high altitudes: pharmacotherapy for acute mountain sickness and high-altitude cerebral and pulmonary oedema.* Expert Opin Pharmacother, 2008. 9(1): p. 119-27.

15. Grossmann, W. M. and B. Koeberle, *The dose-response relationship of acetazolamide on the cerebral blood flow in normal subjects.* Cerebrovasc Dis, 2000. 10(1): p. 65-9.

16. Supuran, C. T., *Carbonic anhydrases: novel therapeutic applications for inhibitors and activators.* Nat Rev Drug Discov, 2008. 7(2): p. 168-81.

17. Altieri, M., et al., *Delayed poststroke dementia: a 4-year follow-up study.* Neurology, 2004. 62(12): p. 2193-7.

18. Schneider, J. A., et al., *Relation of cerebral infarctions to dementia and cognitive function in older persons.* Neurology, 2003. 60(7): p. 1082-8.

19. Lee, D. H., T. R. O'Connor, and G. P. Pfeifer, *Oxidative DNA damage induced by copper and hydrogen peroxide promotes CG→TT tandem mutations at methylated CpG dinucleotides in nucleotide excision repair-deficient cells.* Nucleic Acids Res, 2002. 30(16): p. 3566-73.

20. Adams, S., et al., *Reactive carbonyl formation by oxidative and non-oxidative pathways.* Front Biosci, 2001. 6: p. A17-24.

21. Yamamoto, T., et al., *Selective nitration of mitochondrial complex I by peroxynitrite: involvement in mitochondria dysfunction and cell death of dopaminergic SH-SY5Y cells.* J Neural Transm, 2002. 109(1): p. 1-13.

1. Swerdlow, R. H., J. M. Burns, and S. M. Khan, *The Alzheimer's disease mitochondrial cascade hypothesis: progress and perspectives.* Biochim Biophys Acta, 2014. 1842(8): p. 1219-31.

2. Swerdlow, R. H., J. M. Burns, and S. M. Khan, *The Alzheimer's disease mitochondrial cascade hypothesis.* J Alzheimers Dis, 2010. 20 Suppl 2: p. S265-79.

3. Swerdlow, R. H. and S. M. Khan, *The Alzheimer's disease mitochondrial cascade hypothesis: an update.* Exp Neurol, 2009. 218(2): p. 308-15.

4. Mancuso, M., et al., *Mitochondrial cascade hypothesis of Alzheimer's disease: myth or reality?* Antioxid Redox Signal, 2007. 9(10): p. 1631-46.

5. Swerdlow, R. H. and S. M. Khan, *A "mitochondrial cascade hypothesis" for sporadic Alzheimer's disease.* Med Hypotheses, 2004. 63(1): p. 8-20.

6. Moreira, P. I., et al., *Mitochondria: a therapeutic target in neurodegeneration.* Biochim Biophys Acta, 2010. 1802(1): p. 212-20.

7. Volgyi, K., et al., *Dysfunction of Endoplasmic Reticulum (ER) and Mitochondria (MT) in Alzheimer's Disease: The Role of the ER-MT Cross-Talk.* Curr Alzheimer Res, 2015. 12(7): p. 655-72.

8. Benek, O., et al., *A Direct interaction between mitochondrial proteins and amyloid-beta peptide and its significance for the progression and treatment of Alzheimer's disease.* Curr Med Chem, 2015.

9. Fossati, S., et al., *Differential activation of mitochondrial apoptotic pathways by vasculotropic amyloid-beta variants in cells composing the cerebral vessel walls.* FASEB J, 2010. 24(1): p. 229-41.

10. Atamna, H. and W. H. Frey, 2nd, *Mechanisms of mitochondrial dysfunction and energy deficiency in Alzheimer's disease.* Mitochondrion, 2007. 7(5): p. 297-310.

11. Beal, M. F., *Oxidative damage as an early marker of Alzheimer's disease and mild cognitive impairment.* Neurobiol Aging, 2005. 26(5): p. 585-6.

12. Moreira, P. I., et al., *Mitochondrial dysfunction is a trigger of Alzheimer's disease pathophysiology.* Biochim Biophys Acta, 2010. 1802(1): p. 2-10.

13. Santos, R. X., et al., *Mitochondrial DNA oxidative damage and repair in aging and Alzheimer's disease.* Antioxid Redox Signal, 2013. 18(18): p. 2444-57.

14. Solesio, M. E., et al., *The mitochondria-targeted antioxidant MitoQ reduces aspects of mitochondrial fission in the 6-OHDA cell model of Parkinson's disease.* Biochim Biophys Acta, 2013. 1832(1): p. 174-82.

15. Ghosh, A., et al., *Neuroprotection by a mitochondria-targeted drug in a Parkinson's disease model.* Free Radic Biol Med, 2010. 49(11): p. 1674-84.

16. Solesio, M. E., et al., *Characterization of mitophagy in the 6-hydroxydopamine Parkinson's disease model.* Toxicol Sci, 2012. 129(2): p. 411-20.

17. Solesio, M. E., et al., *3-Nitropropionic acid induces autophagy by forming mitochondrial permeability transition pores rather than activating the mitochondrial fission pathway.* Br J Pharmacol, 2013. 168(1): p. 63-75.

18. Fossati, S., J. Ghiso, and A. Rostagno, *Insights into caspase-mediated apoptotic pathways induced by amyloid-beta in cerebral microvascular endothelial cells.* Neurodegener Dis, 2012. 10(1-4): p. 324-8.

19. Fossati, S., J. Ghiso, and A. Rostagno, *TRAIL death receptors DR4 and DR5 mediate cerebral microvascular endothelial cell apoptosis induced by oligomeric Alzheimer's Abeta.* Cell Death Dis, 2012. 3: p. e321.

20. Revesz, T., et al., *Genetics and molecular pathogenesis of sporadic and hereditary cerebral amyloid angiopathies.* Acta Neuropathol, 2009. 118(1): p. 115-30.

21. Zlokovic, B. V., *The blood-brain barrier in health and chronic neurodegenerative disorders*. Neuron, 2008. 57(2): p. 178-201.
22. Levy, E., et al., *Mutation of the Alzheimer's disease amyloid gene in hereditary cerebral hemorrhage*, Dutch type. Science, 1990. 248(4959): p. 1124-6.
23. Fossati, S., et al., *The carbonic anhydrase inhibitor methazolamide prevents amyloid beta-induced mitochondrial dysfunction and caspase activation protecting neuronal and glial cells in vitro and in the mouse brain*. Neurobiol Dis, 2015.
24. Wang, X., et al., *Inhibitors of cytochrome c release with therapeutic potential for Huntington's disease*. J Neurosci, 2008. 28(38): p. 9473-85.
25. Wang, X., et al., *Methazolamide and melatonin inhibit mitochondrial cytochrome C release and are neuroprotective in experimental models of ischemic injury*. Stroke, 2009. 40(5): p. 1877-85.
26. Fossati, S., et al., *The carbonic anhydrase inhibitor methazolamide prevents amyloid beta-induced mitochondrial dysfunction and caspase activation protecting neuronal and glial cells in vitro and in the mouse brain*. Neurobiol Dis, 2015. 86: p. 29-40.
27. Wright, A., S. Brearey, and C. Imray, *High hopes at high altitudes: pharmacotherapy for acute mountain sickness and high-altitude cerebral and pulmonary oedema*. Expert Opin Pharmacother, 2008. 9(1): p. 119-27.
28. Aronson, J. K., *Old drugs—new uses*. Br J Clin Pharmacol, 2007. 64(5): p. 563-5.
29. Olden, K. W., *The use of antidepressants in functional gastrointestinal disorders: new uses for old drugs*. CNS Spectr, 2005. 10(11): p. 891-6.
30. Chong, C. R. and D. J. Sullivan, Jr., *New uses for old drugs*. Nature, 2007. 448(7154): p. 645-6.
31. Mutsaers, A. J., *Chemotherapy: new uses for old drugs*. Vet Clin North Am Small Anim Pract, 2007. 37(6): p. 1079-90; vi.
32. Sannella, A. R., et al., *New uses for old drugs. Auranofin, a clinically established antiarthritic metallodrug, exhibits potent antimalarial effects in vitro: Mechanistic and pharmacological implications*. FEBS Lett, 2008. 582(6): p. 844-7.
33. da Fonseca, M. A. and P. Casamassimo, *Old drugs, new uses*. Pediatr Dent, 2011. 33(1): p. 67-74.
34. Ekins, S. and A. J. Williams, *Finding promiscuous old drugs for new uses*. Pharm Res, 2011. 28(8): p. 1785-91.
35. Kljun, J., et al., *New uses for old drugs: attempts to convert quinolone antibacterials into potential anticancer agents containing ruthenium*. Inorg Chem, 2013. 52(15): p. 9039-52.
36. Shimohama, S., *Apoptosis in Alzheimer's disease—an update*. Apoptosis, 2000. 5(1): p. 9-16.
37. LeBlanc, A. C., *The role of apoptotic pathways in Alzheimer's disease neurodegeneration and cell death*. Curr Alzheimer Res, 2005. 2(4): p. 389-402.
38. Gottlieb, E., et al., *Mitochondrial membrane potential regulates matrix configuration and cytochrome c release during apoptosis*. Cell Death Differ, 2003. 10(6): p. 709-17.
39. Fossati, S., et al., *Differential contribution of isoaspartate post-translational modifications to the fibrillization and toxic properties of amyloid-beta and the asparagine 23 Iowa mutation*. Biochem J, 2013.
40. Singh, M., H. Sharma, and N. Singh, *Hydrogen peroxide induces apoptosis in HeLa cells through mitochondrial pathway*. Mitochondrion, 2007. 7(6): p. 367-73.
41. Turrens, J. F., *Mitochondrial formation of reactive oxygen species*. J Physiol, 2003. 552(Pt 2): p. 335-44.
42. Giorgi, C., et al., *Mitochondrial Ca(2+) and apoptosis*. Cell Calcium, 2012. 52(1): p. 36-
43. Meldrum, N. U. and F. J. Roughton, *Carbonic anhydrase. Its preparation and properties*. J Physiol, 1933. 80(2): p. 113-42.
44. Jiang, S., et al., *Preformulation study of methazolamide for topical ophthalmic delivery: physicochemical properties and degradation kinetics in aqueous solutions*. Int J Pharm, 2013. 448(2): p. 390-3.
45. Alzheimer's, A., 2015 *Alzheimer's disease facts and figures*. Alzheimers Dement, 2015. 11(3): p. 332-84.
46. Hirai, K., et al., *Mitochondrial abnormalities in Alzheimer's disease*. J Neurosci, 2001. 21(9): p. 3017-23.
47. Santos, R. X., et al., *Alzheimer's disease: diverse aspects of mitochondrial malfunctioning*. Int J Clin Exp Pathol, 2010. 3(6): p. 570-81.
48. Manton, K. G., S. Volovik, and A. Kulminski, *ROS effects on neurodegeneration in Alzheimer's disease and related disorders: on environmental stresses of ionizing radiation*. Curr Alzheimer Res, 2004. 1(4): p. 277-93.
49. Dumont, M. and M. F. Beal, *Neuroprotective strategies involving ROS in Alzheimer disease*. Free Radic Biol Med, 2011. 51(5): p. 1014-26.
50. Multhaup, G., et al., *Reactive oxygen species and Alzheimer's disease*. Biochem Pharmacol, 1997. 54(5): p. 533-9.
51. Kaminsky, Y. G. and E. A. Kosenko, *Effects of amyloid-beta peptides on hydrogen peroxide-metabolizing enzymes in rat brain in vivo*. Free Radic Res, 2008. 42(6): p. 564-73.
52. Milton, N. G., *Role of hydrogen peroxide in the aetiology of Alzheimer's disease: implications for treatment*. Drugs Aging, 2004. 21(2): p. 81-100.
53. Tabner, B. J., et al., *Hydrogen peroxide is generated during the very early stages of aggregation of the amyloid peptides implicated in Alzheimer disease and familial British dementia*. J Biol Chem, 2005. 280(43): p. 35789-92.
54. Ferreiro, E., C. R. Oliveira, and C. M. Pereira, *The release of calcium from the endoplasmic reticulum induced by amyloid-beta and prion peptides activates the mitochondrial apoptotic pathway*. Neurobiol Dis, 2008. 30(3): p. 331-42.
55. Bienert, G. P., J. K. Schjoerring, and T. P. Jahn, *Membrane transport of hydrogen peroxide*. Biochim Biophys Acta, 2006. 1758(8): p. 994-1003.
56. Newington, J. T., et al., *Amyloid beta resistance in nerve cell lines is mediated by the Warburg effect*. PLoS One, 2011. 6(4): p. e19191.
57. Chalmers, S. and D. G. Nicholls, *The relationship between free and total calcium concentrations in the matrix of liver and brain mitochondria*. J Biol Chem, 2003. 278(21): p. 19062-70.
58. Syntichaki, P. and N. Tavernarakis, *The biochemistry of neuronal necrosis: rogue biology?* Nat Rev Neurosci, 2003. 4(8): p. 672-84.
59. MacLennan, D. H. and P. T. Wong, *Isolation of a calcium-sequestering protein from sarcoplasmic reticulum*. Proc Natl Acad Sci USA, 1971. 68(6): p. 1231-5.
60. Solesio, M. E., et al., *Contribution of inorganic polyphosphate towards regulation of mitochondrial free calcium*. Biochim Biophys Acta, 2016. 1860(6): p. 1317-1325.

61. Solesio, M. E., et al., *Inorganic polyphosphate (polyP) as an activator and structural component of the mitochondrial permeability transition pore.* Biochem Soc Trans, 2016. 44(1): p. 7-12.
62. Celsi, F., et al., *Mitochondria, calcium and cell death: a deadly triad in neurodegeneration.* Biochim Biophys Acta, 2009. 1787(5): p. 335-44.
63. Berridge, M. J., *Dysregulation of neural calcium signaling in Alzheimer disease, bipolar disorder and schizophrenia.* Prion, 2013. 7(1): p. 2-13.
64. Garwood, C., et al., *Calcium dysregulation in relation to Alzheimer-type pathology in the ageing brain.* Neuropathol Appl Neurobiol, 2013. 39(7): p. 788-99.
65. Riera, J., et al., *Quantifying the uncertainty of spontaneous Ca2+ oscillations in astrocytes: particulars of Alzheimer's disease.* Biophys J, 2011. 101(3): p. 554-64.
66. Katayama, T., et al., *Induction of neuronal death by ER stress in Alzheimer's disease.* J Chem Neuroanat, 2004. 28(1-2): p. 67-78.
67. Yukioka, F., et al., *Presenilin-1 mutation activates the signaling pathway of caspase-4 in endoplasmic reticulum stress-induced apoptosis.* Neurochem Int, 2008. 52(4-5): p. 683-7.
68. Supnet, C. and I. Bezprozvanny, *Presenilins function in ER calcium leak and Alzheimer's disease pathogenesis.* Cell Calcium, 2011. 50(3): p. 303-9.
69. Hedskog, L., et al., *Modulation of the endoplasmic reticulum-mitochondria interface in Alzheimer's disease and related models.* Proc Natl Acad Sci USA, 2013. 110(19): p. 7916-21.
70. Schon, E. A. and E. Area-Gomez, *Mitochondria-associated ER membranes in Alzheimer disease.* Mol Cell Neurosci, 2013. 55: p. 26-36.
71. Granatiero, V., et al., *Reduced mitochondrial Ca transients stimulate autophagy in human fibroblasts carrying the 13514A>G mutation of the ND5 subunit of NADH dehydrogenase.* Cell Death Differ, 2015.
72. Abramov, A. Y., L. Canevari, and M. R. Duchen, *Calcium signals induced by amyloid beta peptide and their consequences in neurons and astrocytes in culture.* Biochim Biophys Acta, 2004. 1742(1-3): p. 81-7.
73. Shah, G. N., et al., *Pharmacological inhibition of mitochondrial carbonic anhydrases protects mouse cerebral pericytes from high glucose-induced oxidative stress and apoptosis.* J Pharmacol Exp Ther, 2013. 344(3): p. 637-45.
74. Perez-Alvarez, S., et al., *Methadone induces CAD degradation and AIF-mediated necrotic-like cell death in neuroblastoma cells.* Pharmacol Res, 2011. 63(4): p. 352-60.
75. Weksler, B. B., et al., *Blood-brain barrier-specific properties of a human adult brain endothelial cell line.* FASEB J, 2005. 19(13): p. 1872-4.
76. Miravalle, L., et al., *Substitutions at codon 22 of Alzheimer's abeta peptide induce diverse conformational changes and apoptotic effects in human cerebral endothelial cells.* J Biol Chem, 2000. 275(35): p. 27110-6.
77. Dahlgren, K. N., et al., *Oligomeric and fibrillar species of amyloid-beta peptides differentially affect neuronal viability.* J Biol Chem, 2002. 277(35): p. 32046-53.
78. Chazotte, B., *Labeling mitochondria with TMRM or TMRE.* Cold Spring Harb Protoc, 2011. 2011(7): p. 895-7.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

What is claimed is:

1. A method for treating cerebral amyloid angiopathy (CAA) in a subject in need thereof, said method comprising administering to the subject 0.1-1 mg/kg/day of acetazolamide (ATZ) or methazolamide (MTZ).

2. A method for treating Alzheimer's disease (AD) in a subject in need thereof, said method comprising adminsitering to the subject 0.1-1 mg/kg/day of acetazolamide (ATZ) or methazolamide (MTZ).

3. A method for treating hereditary cerebral hemorrhage with amyloidosis in a subject in need thereof, said method comprising administering to the subject 0.1-1 mg/kg/day of acetazolamide (ATZ) or methazolamide (MTZ).

4. The method of claim 1, wherein acetazolamide (ATZ) or methzaolamide (MTZ) is administered to the subject over a period of more than 6 months.

5. The method of claim 2, wherein acetazolamide (ATZ) or methzaolamide (MTZ) is administered to the subject over a period of more than 6 months.

6. The method of claim 3, wherein acetazolamide (ATZ) or methzaolamide (MTZ) is administered to the subject over a period of more than 6 months.

* * * * *